United States Patent
Peeper et al.

(10) Patent No.: US 11,629,179 B2
(45) Date of Patent: Apr. 18, 2023

(54) TWEAK-RECEPTOR AGONISTS FOR USE IN COMBINATION WITH IMMUNOTHERAPY OF A CANCER

(71) Applicant: Stichting Het Nederlands Kanker Instituut - Antoni van Leeuwenhoek Ziekenhuis, Amsterdam (NL)

(72) Inventors: Daniel Simon Peeper, Amsterdam (NL); Thomas Kuilman, Amsterdam (NL); David Willem Vredevoogd, Amsterdam (NL)

(73) Assignee: Stichting Het Nederlands Kanker Instituut—Antoni van Leeuwenhoek Ziekenhuis, Amsterdam (NL)

( * ) Notice: Subject to any disclaimer, the term of this patent is extended or adjusted under 35 U.S.C. 154(b) by 0 days.

(21) Appl. No.: 17/254,307

(22) PCT Filed: Jun. 28, 2019

(86) PCT No.: PCT/EP2019/067300
§ 371 (c)(1),
(2) Date: Dec. 21, 2020

(87) PCT Pub. No.: WO2020/002579
PCT Pub. Date: Jan. 2, 2020

(65) Prior Publication Data
US 2021/0269505 A1    Sep. 2, 2021

(30) Foreign Application Priority Data

Jun. 29, 2018 (EP) .................................. 18180732
Apr. 26, 2019 (EP) .................................. 19171309

(51) Int. Cl.
| | | |
|---|---|---|
| C07K 14/00 | (2006.01) | |
| C07K 14/705 | (2006.01) | |
| A61P 35/00 | (2006.01) | |
| A61K 45/06 | (2006.01) | |
| C07K 14/47 | (2006.01) | |
| A61K 38/00 | (2006.01) | |

(52) U.S. Cl.
CPC ........ C07K 14/70575 (2013.01); A61K 45/06 (2013.01); A61P 35/00 (2018.01); C07K 14/4747 (2013.01); C07K 14/70521 (2013.01); C07K 14/70532 (2013.01); C07K 14/70596 (2013.01); A61K 38/00 (2013.01)

(58) Field of Classification Search
CPC .... C07K 14/70575; A61P 35/00; A61K 45/06
See application file for complete search history.

(56) References Cited

FOREIGN PATENT DOCUMENTS

WO    WO2015189143 A1    12/2015

OTHER PUBLICATIONS

Ma et al. Cancer Discov. Apr. 2013 ; 3(4): 418-429. doi:10.1158/2159-8290.CD-12-0383).*
James E. Vince et al:TWEAK-FN14 signaling induces lysosomal degradation of a CIAP1-TRAF2 complex to sensitize tumor cells to TNF[alpha], The Journal of Cell Biology : JCB, vol. 182, No. 1, Jul. 14, 2008 , pp. 171-184.
C. A. Benetatos et al: "Birinapant (TL32711), a Bivalent SMAC Mimetic, Targets TRAF2-Associated cIAPs, Abrogates TNF-Induced NF-B Activation, and Is Active in Patient-Derived Xenograft Models", Molecular Cancer Therapeutics, vol. 13, No. 4, Apr. 1, 2014, pp. 867-879, XP055623551.
Conor J Kearney et al: "PD-LI and IAPs co-operate to protect tumors from cytotoxic lymphocyte-derived TNF", Cell Death and Differentiation vol. 24, No. 10, Jun. 30, 2017, pp. 1705-1716.
Mark S. Chapman et al: "TWEAK signals through JAK-STAT to induce tumor cell apoptosis", Cytokine, vol. 61, No. 1, Jan. 1, 2013, pp. 210-217.
Vredevoogd David W et al:Augmenting Inmunotherapy Impact by Lowering Tumor TNF Cytotoxicity Threshold, Cell, Elsevier, Amsterdam, NL, vol. 178, No. 3, Jul. 11, 2019, p. 585, XP085747885, ISSN: 0092-8674, DOI: 10.1016/J.CELL.2019.06.)14.

* cited by examiner

Primary Examiner — Jeanette M Lieb
(74) Attorney, Agent, or Firm — N.V. Nederlandsch Octrooibureau

(57) ABSTRACT

The present invention relates to TWEAK-receptor agonists for use in the treatment of a cancer, wherein the TWEAK-receptor agonist is combined with immunotherapy of the cancer. The TWEAK-receptor agonist preferably is a multivalent ligand that causes clustering of TWEAK-receptors at the cell surface. A suitable TWEAK-receptor agonist is an agonistic anti-Fn14 antibody. The TWEAK-receptor agonist and immunotherapy be can further be combined with a SMAC mimetic in the treatment of cancer. The TWEAK-receptor agonist is useful, optionally in combination with a SMAC mimetic, to prevent resistance of a cancer to immunotherapy and/or to treat a cancer comprising tumor cells that are resistant to immunotherapy.

20 Claims, 30 Drawing Sheets
Specification includes a Sequence Listing.

SEQUENCE LISTING

```
<160> NUMBER OF SEQ ID NOS: 73

<210> SEQ ID NO 1
<211> LENGTH: 98
<212> TYPE: DNA
<213> ORGANISM: Artificial sequence
<220> FEATURE:
<223> OTHER INFORMATION: Sequencing Primer Gecko Forward
<220> FEATURE:
<221> NAME/KEY: misc_feature
<222> LOCATION: (59)..(64)
<223> OTHER INFORMATION: n is a, c, g, or t

<400> SEQUENCE: 1
aatgatacgg cgaccaccga gatctacact ctttccctac acgacgctct tccgatctnn      60
nnnnggcttt atatatcttg tggaaaggac gaaacacc                              98

<210> SEQ ID NO 2
<211> LENGTH: 46
<212> TYPE: DNA
<213> ORGANISM: Artificial sequence
<220> FEATURE:
<223> OTHER INFORMATION: Sequencing Primer Gecko Reverse

<400> SEQUENCE: 2
caagcagaag acggcatacg agatccgact cggtgccatt tttcaa                     46
```

```
<210> SEQ ID NO 3
<211> LENGTH: 20
<212> TYPE: DNA
<213> ORGANISM: Artificial sequence
<220> FEATURE:
<223> OTHER INFORMATION: B2M sgRNA 1

<400> SEQUENCE: 3
cgtgagtaaa cctgaatctt                                              20

<210> SEQ ID NO 4
<211> LENGTH: 20
<212> TYPE: DNA
<213> ORGANISM: Artificial sequence
<220> FEATURE:
<223> OTHER INFORMATION: B2M sgRNA 1

<400> SEQUENCE: 4
cgtgagtaaa cctgaatctt                                              20

<210> SEQ ID NO 5
<211> LENGTH: 20
<212> TYPE: DNA
<213> ORGANISM: Artificial sequence
<220> FEATURE:
<223> OTHER INFORMATION: B2M sgRNA 2

<400> SEQUENCE: 5
cagtaagtca acttcaatgt                                              20

<210> SEQ ID NO 6
<211> LENGTH: 20
<212> TYPE: DNA
<213> ORGANISM: Artificial sequence
<220> FEATURE:
<223> OTHER INFORMATION: BIRC2 sgRNA 1

<400> SEQUENCE: 6
atatcctcat cttcttgaac                                              20

<210> SEQ ID NO 7
<211> LENGTH: 20
<212> TYPE: DNA
<213> ORGANISM: Artificial sequence
<220> FEATURE:
<223> OTHER INFORMATION: BIRC2 sgRNA 1

<400> SEQUENCE: 7
atatcctcat cttcttgaac                                              20

<210> SEQ ID NO 8
<211> LENGTH: 20
<212> TYPE: DNA
<213> ORGANISM: Artificial sequence
<220> FEATURE:
<223> OTHER INFORMATION: BIRC2 sgRNA 2

<400> SEQUENCE: 8
ggcttgaggt gttgggaatc                                              20

<210> SEQ ID NO 9
<211> LENGTH: 20
<212> TYPE: DNA
<213> ORGANISM: Artificial sequence
<220> FEATURE:
<223> OTHER INFORMATION: BIRC2 sgRNA 3
```

<400> SEQUENCE: 9
acatcatcat tgcgaccttc                                               20

<210> SEQ ID NO 10
<211> LENGTH: 20
<212> TYPE: DNA
<213> ORGANISM: Artificial sequence
<220> FEATURE:
<223> OTHER INFORMATION: BIRC2 sgRNA 4

<400> SEQUENCE: 10
tgtttgctgc gcccgcactg                                               20

<210> SEQ ID NO 11
<211> LENGTH: 20
<212> TYPE: DNA
<213> ORGANISM: Artificial sequence
<220> FEATURE:
<223> OTHER INFORMATION: BIRC2 sgRNA 5

<400> SEQUENCE: 11
atgatgctat gtcagaacac                                               20

<210> SEQ ID NO 12
<211> LENGTH: 20
<212> TYPE: DNA
<213> ORGANISM: Artificial sequence
<220> FEATURE:
<223> OTHER INFORMATION: BIRC3 sgRNA 1

<400> SEQUENCE: 12
tctactaaag cccatttcca                                               20

<210> SEQ ID NO 13
<211> LENGTH: 20
<212> TYPE: DNA
<213> ORGANISM: Artificial sequence
<220> FEATURE:
<223> OTHER INFORMATION: BIRC3 sgRNA 2

<400> SEQUENCE: 13
ggtaactggc ttgaacttga                                               20

<210> SEQ ID NO 14
<211> LENGTH: 20
<212> TYPE: DNA
<213> ORGANISM: Artificial sequence
<220> FEATURE:
<223> OTHER INFORMATION: BIRC3 sgRNA 3

<400> SEQUENCE: 14
gagagtttga ataagagcca                                               20

<210> SEQ ID NO 15
<211> LENGTH: 20
<212> TYPE: DNA
<213> ORGANISM: Artificial sequence
<220> FEATURE:
<223> OTHER INFORMATION: CFLAR sgRNA 1

<400> SEQUENCE: 15
gtttctccaa ctcaaccaca                                               20

-continued

```
<210> SEQ ID NO 16
<211> LENGTH: 20
<212> TYPE: DNA
<213> ORGANISM: Artificial sequence
<220> FEATURE:
<223> OTHER INFORMATION: CFLAR sgRNA 1

<400> SEQUENCE: 16
gtttctccaa ctcaaccaca                                              20

<210> SEQ ID NO 17
<211> LENGTH: 20
<212> TYPE: DNA
<213> ORGANISM: Artificial sequence
<220> FEATURE:
<223> OTHER INFORMATION: CFLAR sgRNA 2

<400> SEQUENCE: 17
gggccgaggc aagataagca                                              20

<210> SEQ ID NO 18
<211> LENGTH: 20
<212> TYPE: DNA
<213> ORGANISM: Artificial sequence
<220> FEATURE:
<223> OTHER INFORMATION: Human non-targeting control sgRNA 1

<400> SEQUENCE: 18
ggttgctgtg acgaacgggg                                              20

<210> SEQ ID NO 19
<211> LENGTH: 20
<212> TYPE: DNA
<213> ORGANISM: Artificial sequence
<220> FEATURE:
<223> OTHER INFORMATION: Human non-targeting control sgRNA 2

<400> SEQUENCE: 19
ggttgctgtg acgaacgggg                                              20

<210> SEQ ID NO 20
<211> LENGTH: 20
<212> TYPE: DNA
<213> ORGANISM: Artificial sequence
<220> FEATURE:
<223> OTHER INFORMATION: Human non-targeting control sgRNA 3

<400> SEQUENCE: 20
gcacgaggtg aacagccgct                                              20

<210> SEQ ID NO 21
<211> LENGTH: 20
<212> TYPE: DNA
<213> ORGANISM: Artificial sequence
<220> FEATURE:
<223> OTHER INFORMATION: IFNGR1 sgRNA 1

<400> SEQUENCE: 21
cgaacgacgg tacctgagga                                              20

<210> SEQ ID NO 22
<211> LENGTH: 20
<212> TYPE: DNA
<213> ORGANISM: Artificial sequence
<220> FEATURE:
<223> OTHER INFORMATION: IKBKG sgRNA 1
```

```
<400> SEQUENCE: 22
tcaggagcgc cctgttctga                                              20

<210> SEQ ID NO 23
<211> LENGTH: 20
<212> TYPE: DNA
<213> ORGANISM: Artificial sequence
<220> FEATURE:
<223> OTHER INFORMATION: IKBKG sgRNA 2

<400> SEQUENCE: 23
ctcaccgacc ctccagagcc                                              20

<210> SEQ ID NO 24
<211> LENGTH: 20
<212> TYPE: DNA
<213> ORGANISM: Artificial sequence
<220> FEATURE:
<223> OTHER INFORMATION: KBKG sgRNA 1

<400> SEQUENCE: 24
tcaggagcgc cctgttctga                                              20

<210> SEQ ID NO 25
<211> LENGTH: 20
<212> TYPE: DNA
<213> ORGANISM: Artificial sequence
<220> FEATURE:
<223> OTHER INFORMATION: MAP3K7 sgRNA 1

<400> SEQUENCE: 25
agagcctgat gactcgttgt                                              20

<210> SEQ ID NO 26
<211> LENGTH: 20
<212> TYPE: DNA
<213> ORGANISM: Artificial sequence
<220> FEATURE:
<223> OTHER INFORMATION: MAP3K7 sgRNA 1

<400> SEQUENCE: 26
agagcctgat gactcgttgt                                              20

<210> SEQ ID NO 27
<211> LENGTH: 20
<212> TYPE: DNA
<213> ORGANISM: Artificial sequence
<220> FEATURE:
<223> OTHER INFORMATION: MAP3K7 sgRNA 2

<400> SEQUENCE: 27
gatggagtta tctgatccat                                              20

<210> SEQ ID NO 28
<211> LENGTH: 20
<212> TYPE: DNA
<213> ORGANISM: Artificial sequence
<220> FEATURE:
<223> OTHER INFORMATION: Mouse B2m sgRNA 1

<400> SEQUENCE: 28
actctggata gcatacaggc                                              20
```

```
<210> SEQ ID NO 29
<211> LENGTH: 20
<212> TYPE: DNA
<213> ORGANISM: Artificial sequence
<220> FEATURE:
<223> OTHER INFORMATION: Mouse non-targeting control sgRNA 1

<400> SEQUENCE: 29
gtattactga tattggtggg                                              20

<210> SEQ ID NO 30
<211> LENGTH: 20
<212> TYPE: DNA
<213> ORGANISM: Artificial sequence
<220> FEATURE:
<223> OTHER INFORMATION: Mouse Traf2 sgRNA 1

<400> SEQUENCE: 30
taacgctgcc cgcagagagg                                              20

<210> SEQ ID NO 31
<211> LENGTH: 20
<212> TYPE: DNA
<213> ORGANISM: Artificial sequence
<220> FEATURE:
<223> OTHER INFORMATION: RIPK1 sgRNA 1

<400> SEQUENCE: 31
gagagtgcag aactggacag                                              20

<210> SEQ ID NO 32
<211> LENGTH: 20
<212> TYPE: DNA
<213> ORGANISM: Artificial sequence
<220> FEATURE:
<223> OTHER INFORMATION: RIPK1 sgRNA 2

<400> SEQUENCE: 32
agcgcgacac ggagactagg                                              20

<210> SEQ ID NO 33
<211> LENGTH: 20
<212> TYPE: DNA
<213> ORGANISM: Artificial sequence
<220> FEATURE:
<223> OTHER INFORMATION: RIPK1 sgRNA 3

<400> SEQUENCE: 33
cttcctctat gatgacgccc                                              20

<210> SEQ ID NO 34
<211> LENGTH: 20
<212> TYPE: DNA
<213> ORGANISM: Artificial sequence
<220> FEATURE:
<223> OTHER INFORMATION: TBK1 sgRNA 1

<400> SEQUENCE: 34
atcacttctt tattcctacg                                              20

<210> SEQ ID NO 35
<211> LENGTH: 20
<212> TYPE: DNA
<213> ORGANISM: Artificial sequence
<220> FEATURE:
<223> OTHER INFORMATION: TBK1 sgRNA 1
```

<400> SEQUENCE: 35
atcacttctt tattcctacg                                         20

<210> SEQ ID NO 36
<211> LENGTH: 20
<212> TYPE: DNA
<213> ORGANISM: Artificial sequence
<220> FEATURE:
<223> OTHER INFORMATION: TBK1 sgRNA 2

<400> SEQUENCE: 36
gaagaacctt ctaatgccta                                         20

<210> SEQ ID NO 37
<211> LENGTH: 20
<212> TYPE: DNA
<213> ORGANISM: Artificial sequence
<220> FEATURE:
<223> OTHER INFORMATION: TRADD sgRNA 1

<400> SEQUENCE: 37
tccctcgcgc tcgtactcgt                                         20

<210> SEQ ID NO 38
<211> LENGTH: 20
<212> TYPE: DNA
<213> ORGANISM: Artificial sequence
<220> FEATURE:
<223> OTHER INFORMATION: TRADD sgRNA 1

<400> SEQUENCE: 38
tccctcgcgc tcgtactcgt                                         20

<210> SEQ ID NO 39
<211> LENGTH: 20
<212> TYPE: DNA
<213> ORGANISM: Artificial sequence
<220> FEATURE:
<223> OTHER INFORMATION: TRADD sgRNA 2

<400> SEQUENCE: 39
caccgagtgc tgggcgagcg                                         20

<210> SEQ ID NO 40
<211> LENGTH: 20
<212> TYPE: DNA
<213> ORGANISM: Artificial sequence
<220> FEATURE:
<223> OTHER INFORMATION: TRAF1 sgRNA 1

<400> SEQUENCE: 40
atggctacaa gttgtgcctg                                         20

<210> SEQ ID NO 41
<211> LENGTH: 20
<212> TYPE: DNA
<213> ORGANISM: Artificial sequence
<220> FEATURE:
<223> OTHER INFORMATION: TRAF1 sgRNA 2

<400> SEQUENCE: 41
aggaagccgt cttcgaactc                                         20

```
<210> SEQ ID NO 42
<211> LENGTH: 20
<212> TYPE: DNA
<213> ORGANISM: Artificial sequence
<220> FEATURE:
<223> OTHER INFORMATION: TRAF1 sgRNA 3

<400> SEQUENCE: 42
caccgtctgc caggacccaa                                              20

<210> SEQ ID NO 43
<211> LENGTH: 20
<212> TYPE: DNA
<213> ORGANISM: Artificial sequence
<220> FEATURE:
<223> OTHER INFORMATION: TRAF2 sgRNA 1

<400> SEQUENCE: 43
cctgcagaaa cgtcctccgc                                              20

<210> SEQ ID NO 44
<211> LENGTH: 20
<212> TYPE: DNA
<213> ORGANISM: Artificial sequence
<220> FEATURE:
<223> OTHER INFORMATION: TRAF2 sgRNA 1

<400> SEQUENCE: 44
cctgcagaaa cgtcctccgc                                              20

<210> SEQ ID NO 45
<211> LENGTH: 20
<212> TYPE: DNA
<213> ORGANISM: Artificial sequence
<220> FEATURE:
<223> OTHER INFORMATION: TRAF2 sgRNA 2

<400> SEQUENCE: 45
atatatgccc tcgtgaacac                                              20

<210> SEQ ID NO 46
<211> LENGTH: 20
<212> TYPE: DNA
<213> ORGANISM: Artificial sequence
<220> FEATURE:
<223> OTHER INFORMATION: TRAF2 sgRNA 2

<400> SEQUENCE: 46
cctgcggagg acgtttctgc                                              20

<210> SEQ ID NO 47
<211> LENGTH: 20
<212> TYPE: DNA
<213> ORGANISM: Artificial sequence
<220> FEATURE:
<223> OTHER INFORMATION: TRAF2 sgRNA 3

<400> SEQUENCE: 47
accgaatgtc ccgcgtgcaa                                              20

<210> SEQ ID NO 48
<211> LENGTH: 20
<212> TYPE: DNA
<213> ORGANISM: Artificial sequence
<220> FEATURE:
<223> OTHER INFORMATION: TRAF2 sgRNA 3
```

<400> SEQUENCE: 48
gcggaggacg tttctgcagg                                           20

<210> SEQ ID NO 49
<211> LENGTH: 20
<212> TYPE: DNA
<213> ORGANISM: Artificial sequence
<220> FEATURE:
<223> OTHER INFORMATION: TRAF2 sgRNA 4

<400> SEQUENCE: 49
gcctttgcac gcgggacatt                                           20

<210> SEQ ID NO 50
<211> LENGTH: 20
<212> TYPE: DNA
<213> ORGANISM: Artificial sequence
<220> FEATURE:
<223> OTHER INFORMATION: TRAF2 sgRNA 4

<400> SEQUENCE: 50
ggggaccctg aaagaatacg                                           20

<210> SEQ ID NO 51
<211> LENGTH: 20
<212> TYPE: DNA
<213> ORGANISM: Artificial sequence
<220> FEATURE:
<223> OTHER INFORMATION: TRAF2 sgRNA 5

<400> SEQUENCE: 51
ggggaccctg aaagaatacg                                           20

<210> SEQ ID NO 52
<211> LENGTH: 20
<212> TYPE: DNA
<213> ORGANISM: Artificial sequence
<220> FEATURE:
<223> OTHER INFORMATION: TRAF2 sgRNA 6

<400> SEQUENCE: 52
atatatgccc tcgtgaacac                                           20

<210> SEQ ID NO 53
<211> LENGTH: 20
<212> TYPE: DNA
<213> ORGANISM: Artificial sequence
<220> FEATURE:
<223> OTHER INFORMATION: TRAF2 sgRNA 7

<400> SEQUENCE: 53
cctgcggagg acgtttctgc                                           20

<210> SEQ ID NO 54
<211> LENGTH: 20
<212> TYPE: DNA
<213> ORGANISM: Artificial sequence
<220> FEATURE:
<223> OTHER INFORMATION: TRAF2 sgRNA 8

<400> SEQUENCE: 54
cctgcagaaa cgtcctccgc                                           20

```
<210> SEQ ID NO 55
<211> LENGTH: 20
<212> TYPE: DNA
<213> ORGANISM: Artificial sequence
<220> FEATURE:
<223> OTHER INFORMATION: TRAF3 sgRNA 1

<400> SEQUENCE: 55
agacaccgac tgtccctgcg                                               20

<210> SEQ ID NO 56
<211> LENGTH: 20
<212> TYPE: DNA
<213> ORGANISM: Artificial sequence
<220> FEATURE:
<223> OTHER INFORMATION: TRAF3 sgRNA 2

<400> SEQUENCE: 56
ggagaaggcg tgtaaatacc                                               20

<210> SEQ ID NO 57
<211> LENGTH: 20
<212> TYPE: DNA
<213> ORGANISM: Artificial sequence
<220> FEATURE:
<223> OTHER INFORMATION: TRAF3 sgRNA 3

<400> SEQUENCE: 57
acacttgtac ttgtcctcca                                               20

<210> SEQ ID NO 58
<211> LENGTH: 20
<212> TYPE: DNA
<213> ORGANISM: Artificial sequence
<220> FEATURE:
<223> OTHER INFORMATION: TRAF4 sgRNA 1

<400> SEQUENCE: 58
tcctggagaa gcccaagcga                                               20

<210> SEQ ID NO 59
<211> LENGTH: 20
<212> TYPE: DNA
<213> ORGANISM: Artificial sequence
<220> FEATURE:
<223> OTHER INFORMATION: TRAF4 sgRNA 2

<400> SEQUENCE: 59
cccccagatc tacccagacc                                               20

<210> SEQ ID NO 60
<211> LENGTH: 20
<212> TYPE: DNA
<213> ORGANISM: Artificial sequence
<220> FEATURE:
<223> OTHER INFORMATION: TRAF4 sgRNA 3

<400> SEQUENCE: 60
agtgtgcagg tagatcacgg                                               20

<210> SEQ ID NO 61
<211> LENGTH: 20
<212> TYPE: DNA
<213> ORGANISM: Artificial sequence
<220> FEATURE:
<223> OTHER INFORMATION: TRAF5 sgRNA 1
```

```
<400> SEQUENCE: 61
attctgggcc ggtaccaggt                                              20

<210> SEQ ID NO 62
<211> LENGTH: 20
<212> TYPE: DNA
<213> ORGANISM: Artificial sequence
<220> FEATURE:
<223> OTHER INFORMATION: TRAF5 sgRNA 2

<400> SEQUENCE: 62
agtgccggga gccagtccta                                              20

<210> SEQ ID NO 63
<211> LENGTH: 20
<212> TYPE: DNA
<213> ORGANISM: Artificial sequence
<220> FEATURE:
<223> OTHER INFORMATION: TRAF5 sgRNA 3

<400> SEQUENCE: 63
tagagtacca gtttgtggag                                              20

<210> SEQ ID NO 64
<211> LENGTH: 20
<212> TYPE: DNA
<213> ORGANISM: Artificial sequence
<220> FEATURE:
<223> OTHER INFORMATION: TRAF6 sgRNA 1

<400> SEQUENCE: 64
acattctgaa ggattgtcca                                              20

<210> SEQ ID NO 65
<211> LENGTH: 20
<212> TYPE: DNA
<213> ORGANISM: Artificial sequence
<220> FEATURE:
<223> OTHER INFORMATION: TRAF6 sgRNA 2

<400> SEQUENCE: 65
gattctacac tggcaaaccc                                              20

<210> SEQ ID NO 66
<211> LENGTH: 20
<212> TYPE: DNA
<213> ORGANISM: Artificial sequence
<220> FEATURE:
<223> OTHER INFORMATION: TRAF6 sgRNA 3

<400> SEQUENCE: 66
gaagcagtgc aaacgccatg                                              20

<210> SEQ ID NO 67
<211> LENGTH: 20
<212> TYPE: DNA
<213> ORGANISM: Artificial sequence
<220> FEATURE:
<223> OTHER INFORMATION: TRAF7 sgRNA 1

<400> SEQUENCE: 67
actccttcag gccctcgaag                                              20
```

```
<210> SEQ ID NO 68
<211> LENGTH: 20
<212> TYPE: DNA
<213> ORGANISM: Artificial sequence
<220> FEATURE:
<223> OTHER INFORMATION: TRAF7 sgRNA 2

<400> SEQUENCE: 68
cagagatggc ggagtcggag                                               20

<210> SEQ ID NO 69
<211> LENGTH: 20
<212> TYPE: DNA
<213> ORGANISM: Artificial sequence
<220> FEATURE:
<223> OTHER INFORMATION: TRAF7 sgRNA 3

<400> SEQUENCE: 69
cgtggtggtg aacaacatcg                                               20

<210> SEQ ID NO 70
<211> LENGTH: 20
<212> TYPE: DNA
<213> ORGANISM: Artificial sequence
<220> FEATURE:
<223> OTHER INFORMATION: TSC1 sgRNA 1

<400> SEQUENCE: 70
cgagatagac ttccgccacg                                               20

<210> SEQ ID NO 71
<211> LENGTH: 20
<212> TYPE: DNA
<213> ORGANISM: Artificial sequence
<220> FEATURE:
<223> OTHER INFORMATION: TSC1 sgRNA 2

<400> SEQUENCE: 71
attcgttaat cctgtccaag                                               20

<210> SEQ ID NO 72
<211> LENGTH: 20
<212> TYPE: DNA
<213> ORGANISM: Artificial sequence
<220> FEATURE:
<223> OTHER INFORMATION: TSC2 sgRNA 1

<400> SEQUENCE: 72
agcacgcagt ggaagcactc                                               20

<210> SEQ ID NO 73
<211> LENGTH: 20
<212> TYPE: DNA
<213> ORGANISM: Artificial sequence
<220> FEATURE:
<223> OTHER INFORMATION: TSC2 sgRNA 2

<400> SEQUENCE: 73
gtggcctcaa caatcgcatc                                               20
```

TWEAK-RECEPTOR AGONISTS FOR USE IN COMBINATION WITH IMMUNOTHERAPY OF A CANCER

FIELD OF THE INVENTION

The present invention relates to the field of medicine, in particular to molecular oncology. More specifically, the invention relates to TWEAK-receptor agonists for use in the treatment of a cancer, in which treatment, the TWEAK-receptor agonist is combined with an immunotherapy of the cancer.

BACKGROUND ART

Clinical strategies that unleash T cell cytotoxicity have significantly improved the perspective of cancer patients (Borghaei et al., 2015; Hodi et al., 2010; Larkin et al., 2015; Motzer et al., 2015; Robert et al., 2011; Rosenberg et al., 2016; Wolchok et al., 2017). By blocking inhibitory checkpoints, particularly PD-1, PD-L1/2 or CTLA-4, T cells can be functionally reinvigorated and productively respond to their cognate antigens (Ahmadzadeh et al., 2009; Barber et al., 2006; Freeman et al., 2000; Leach et al., 1996; Nishimura et al., 1996, Int. Immunol. 8:773; (Latchman et al. (2001) Nat. Immunol. 2:261). Renewed activity of CD8 T cells has been shown to be accompanied by increased proliferation, cytokine production and cytolytic activity (Barber et al., 2006; Freeman et al., 2000; Jacquelot et al., 2017). This inflammatory tumor microenvironment is thought to allow for efficient immune clearance (Chen and Mellman, 2017; Ji et al., 2012). However, for various reasons, including intrinsic and adaptive tumor resistance, most patients do not benefit durably (Borghaei et al., 2015; Hodi et al., 2010; Larkin et al., 2015; Motzer et al., 2015; Robert et al., 2011; Rosenberg et al., 2016; Sharma et al., 2017; Wolchok et al., 2017), emphasizing the need for additional, novel therapeutic targets.

Most immunotherapeutic approaches that are currently in the clinic aim to improve T cell function and leverage their activity (Ahmadzadeh et al., 2009; Barber et al., 2006; Freeman et al., 2000; Leach et al., 1996). While active cytotoxic T cells are a prerequisite for the success of an immune response, modulating the susceptibility to T cell-derived death signals of the target tumor may be an equally effective immunotherapeutic strategy. Cytokines such as IFNγ, TNF and TRAIL contribute to the antitumor activity of cytotoxic T cells by inducing growth arrest and apoptosis (Barber et al., 2006; Barth et al., 1991; Benci et al., 2016; Brincks et al., 2008; Gao et al., 2016; Kearney et al., 2017, 2018). Defects in the IFNγ pathway in tumors render patients resistant to immune checkpoint therapy (Gao et al., 2016; Zaretsky et al., 2016). These observations highlight the importance of a thorough understanding of tumor-intrinsic signaling pathways, as this may open new avenues for therapeutic intervention.

Recently, candidate therapeutic targets have been identified that control IFNγ-induced signaling and as such, their modulation assists in driving an antitumor immune response (Manguso et al., 2017; Pan et al., 2018; Patel et al., 2017). It is well established that also additional cytokines contribute to T cell cytotoxicity (Barber et al., 2006; Barth et al., 1991; Benci et al., 2016; Brincks et al., 2008; Gao et al., 2016; Ji et al., 2012; Kakaradov et al., 2017; Kearney et al., 2017; Zhang et al., 2015). However, it has not been systematically catalogued how tumors respond to cytotoxic T cell cytokines other than IFNγ. Similarly, IFNγ-independent tumor signal pathways have not yet been explored in an unbiased fashion for new therapeutic targets.

Vince et al. (2008, J. Cell Biol. Vol. 182 No. 1 171-184) describe that TWEAK-FN14 signaling induces lysosomal degradation of a cIAP1-TRAF2 complex to sensitize tumor cells to TNFα.

Michaelson et al. (2011, mAbs 3:4, 362-375) describe the development of an Fn14 agonistic antibody, which when tested on a panel of 38 human tumor cell lines induced growth inhibition in approximately 50% of the cell lines.

There is however still a need for novel therapeutic approaches and synergistic combinations to address the tumors ability to escape from T cell-mediated killing and which contribute to the impact and durability of immunotherapy of tumors.

DESCRIPTION OF EMBODIMENTS

Definitions

Unless defined otherwise, technical and scientific terms used herein have the same meaning as commonly understood by one of ordinary skill in the art to which this disclosure belongs. One skilled in the art will recognize many methods and materials similar or equivalent to those described herein, which could be used in the practice of the present invention. Indeed, the present invention is in no way limited to the methods and materials described.

For purposes of the present invention, the following terms are defined below.

As used herein, the singular forms "a," "an" and "the" include plural referents unless the context clearly dictates otherwise. For example, a method for administrating a drug or an agent includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases.

As used herein, with "At least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

As used herein "cancer" and "cancerous", refer to or describe the physiological condition in mammals that is typically characterized by unregulated cell growth. Cancer is also referred to as malignant neoplasm.

As used herein, "in combination with" is intended to refer to all forms of administration that provide a first drug together with a further (second, third) drug. The drugs may be administered simultaneous, separate or sequential and in any order. Drugs administered in combination have biological activity in the subject to which the drugs are delivered.

As used herein "simultaneous" administration refers to administration of more than one drug at the same time, but not necessarily via the same route of administration or in the form of one combined formulation. For example, one drug may be provided orally whereas the other drug may be provided intravenously during a patient's visit to a hospital. Separate includes the administration of the drugs in separate form and/or at separate moments in time, but again, not necessarily via the same route of administration. Sequentially indicates that the administration of a first drug is followed, immediately or in time, by the administration of the second drug.

A used herein "compositions", "products" or "combinations" useful in the methods of the present disclosure include those suitable for various routes of administration, including, but not limited to, intravenous, subcutaneous, intradermal, subdermal, intranodal, intratumoral, intramuscular, intraperitoneal, oral, nasal, topical (including buccal and sublingual), rectal, vaginal, aerosol and/or parenteral or mucosal application. The compositions, formulations, and products according to the disclosure invention normally comprise the drugs (alone or in combination) and one or more suitable pharmaceutically acceptable excipients.

As used herein, "an effective amount" is meant the amount of an agent required to ameliorate the symptoms of a disease relative to an untreated patient. The effective amount of active agent(s) used to practice the present invention for therapeutic treatment of a cancer varies depending upon the manner of administration, the age, body weight, and general health of the subject. Ultimately, the attending physician or veterinarian will decide the appropriate amount and dosage regimen. Such amount is referred to as an "effective" amount. Thus, in connection with the administration of a drug which, in the context of the current disclosure, is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

"Sequence identity" is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention is ClustalW (1.83) using a blosum matrix and default settings (Gap opening penalty:10; Gap extension penalty: 0.05). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Nucleotide sequences of the invention may also be defined by their capability to hybridize with the specific nucleotide sequences disclosed herein or parts thereof, under moderate, or preferably under stringent hybridization conditions. Stringent hybridization conditions are herein defined as conditions that allow a nucleic acid sequence of at least about 25, preferably about 50 nucleotides, 75 or 100 and most preferably of about 200 or more nucleotides, to hybridize at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridization is performed overnight, i.e. at least for 10 hours and preferably washing is performed for at least one hour with at least two changes of the washing solution. These conditions will usually allow the specific hybridization of sequences having about 90% or more sequence identity.

Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

The term "complementarity" is herein defined as the sequence identity of a sequence to a fully complementary strand. For example, a sequence that is 100% complementary (or fully complementary) is herein understood as having 100% sequence identity with the complementary strand and e.g. a sequence that is 80% complementary is herein understood as having 80% sequence identity to the (fully) complementary strand.

As used herein, the term "about" is used to describe and account for small variations. For example, the term can refer to less than or equal to ±(+ or −) 10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The term "agent" refers generally to any entity which is normally not present or not present at the levels being administered to a cell, tissue or subject. An agent can be a compound or a composition. An agent can e.g. be selected from the group consisting of: polynucleotides, polypeptides, small molecules, antibodies and functional fragments thereof.

As used herein, the term "small molecule" can refer to compounds that are "natural product-like," but mostly will refer synthetic compounds. A small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular mass equal to or less than 700 Daltons.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG). See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, tetrabodies and hexameric antibodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, N.Y. (1981), pp. 563 681 (both of which are incorporated herein by reference in their entireties).

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen. Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well-known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Any of the anti-TweakR antibodies described herein can be chimeric.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85%, at least 90%, and at least 95% identical. Hence, all parts of a humanized immunoglobulin, except possibly the CDRs, are substantially identical to corresponding parts of one or more native human immunoglobulin sequences. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585, 089), veneering or resurfacing (EP 592,106; EP 519,596; Padlan, Mol. Immunol., 28:489 498 (1991); Studnicka et al., Prot. Eng. 7:805 814 (1994); Roguska et al., Proc. Natl. Acad. Sci. 91:969 973 (1994), and chain shuffling (U.S. Pat. No. 5,565,332), all of which are hereby incorporated by reference in their entireties. The anti-TweakR antibodies described herein include humanized antibodies, such as mouse humanized antibodies, fully human antibodies, and mouse antibodies.

As an alternative to humanization, human antibodies can be generated. By "human antibody" is meant an antibody containing entirely human light and heavy chains as well as constant regions, produced by any of the known standard methods. For example, transgenic animals (e.g., mice) are available that are capable, upon immunization, of producing a full repertoire of human antibodies in the absence of endogenous immunoglobulin production. For example, it has been described that the homozygous deletion of the antibody heavy-chain joining region PH gene in chimeric and germ-line mutant mice results in the complete inhibition of endogenous antibody production. Transfer of the human germ-line immunoglobulin gene array in such germ line mutant mice will result in the production of human antibodies after immunization. See, e.g., Jakobovits et al., Proc. Nat. Acad. Sci. USA, 90:255 1 (1993); Jakobovits et al., Nature, 362:255-258 (1993). Alternatively, phage display technology (McCafferty et al., Nature 348:552-553 (1990)) can be used to produce human antibodies and antibody fragments in vitro, from immunoglobulin variable (V) domain gene repertoires from donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., Current Opinion in Structural Biology 3:564-57 1 (1993). Human antibodies may also be generated by in vitro activated B cells or SCID mice with its immune system reconstituted with human cells. Once a human antibody is obtained, its coding DNA sequences can be isolated, cloned and introduced into an appropriate expression system i.e. a cell line, preferably from a mammal, which subsequently express and liberate it into a culture media from which the antibody can be isolated.

DETAILED DESCRIPTION OF THE INVENTION

By performing a genetic screen, the inventors identified the E3 ubiquitin ligase TRAF2 as a crucial determinant of sensitivity to T cell attack. Specifically, the inventors found that by genetically inactivating TRAF2, they can sensitize multiple tumor cell lines in vitro and in vivo to T cell attack (co-pending application EP 18180732.2).

To exploit this phenomenon therapeutically, the inventors took advantage of previously published observations, which showed that upon ligation of TNFRSF12A, also known as Fn14 and TWEAK-receptor, by its ligand, TWEAK, TRAF2 was lysosomally degraded (Vince et al., 2008) and of the fact that other groups have developed agonistic antibodies that could mimic the effect of TWEAK (Michaelson et al., 2011). The inventors have surprisingly found that such TWEAK-receptor agonists can be used therapeutically to reduce TRAF2 levels, thereby sensitizing tumor cells to T cell attack, which treatment modality is thus capable of radically improving the efficacy of classical immunotherapies.

In a first aspect the invention therefore relates to a TWEAK-receptor agonist. Preferably, the agonist is for use in the treatment of a cancer. Preferably, in the treatment of the cancer, the TWEAK-receptor agonist is combined with an immunotherapy of the cancer. The invention thus pertains to a TWEAK-receptor agonist for use in combination with an immunotherapy of a cancer.

A TWEAK-receptor agonist is herein defined as any agent that triggers degradation, preferably proteasomal degradation, of TRAF2 in a (tumor) cell. TRAF2 is Tnf receptor-associated factor 2 protein (NP_066961) that in humans is encoded by the TRAF2 gene (NM_021138, NM_009422 or NM_001290413). As has been described by Vince et al. (2008, supra), upon binding of its ligand TWEAK (TNF-like weak inducer of apoptosis) the TNF superfamily receptor Fn14 (also known as the TWEAK-receptor (TWEAKR), a protein that in humans is encoded by the TNFRSF12A gene) recruits a cIAP1-TRAF2 complex. Unlike IAP antagonists that cause rapid proteasomal degradation of cIAP1, signaling by Fn14 promotes the lysosomal degradation of cIAP1-TRAF2 in a cIAP1-dependent manner. Moreover, Cabal-Hierro et al. (Oncotarget. 2014 Jan. 15; 5(1):224-36) show that also activation of other TNFR-family members, such as e.g. TNFR2, results in TRAF2 degradation. TNFR2 preferably has an amino acid sequence of one of NP_001057 and NP_035740.

A TWEAK-receptor agonist that triggers degradation of TRAF2 for use in the invention is therefore preferably an agonistic ligand of a TNFR-family member, which ligands are generally known in the art. More preferably, the TWEAK-receptor agonist that triggers degradation of TRAF2 is an agonistic ligand of at least one of TNFR2 and Fn14/TWEAKR/TNFRSF12A (with e.g. the amino acid sequence NP_057723). Most preferably, the TWEAK-receptor agonist that triggers degradation of TRAF2 is an agonistic ligand of Fn14/TWEAKR/TNFRSF12A. A preferred agonistic ligand of Fn14 is TWEAK itself (e.g. a protein having the amino acid sequence of any one of NP_003800, NP_742086 and NP_035744), or a protein comprising an agonistic fragment of TWEAK. For example, recombinant human TWEAK as is obtainable from a variety of sources, or an agonistic fragment thereof can be used as agonistic ligand of Fn14.

Another preferred agonistic ligand of Fn14/TWEAKR/TNFRSF12A for use in the invention is an agonistic TWEAK mimetic that acts as an agonistic ligand of Fn14. The agonistic TWEAK mimetic can be a peptide, a peptidomimetic, an aptamer or a small molecule that acts as an agonistic ligand of Fn14. Preferably, however, the agonistic TWEAK mimetic is an agonistic anti-Fn14 antibody or an agonistic fragment thereof. The agonistic anti-Fn14 antibody or fragment thereof preferably is a humanized or human antibody. Agonistic anti-Fn14 antibodies that can be applied as TWEAK-receptor agonist of the invention include e.g. the humanized anti-Fn14 agonistic antibody B11B036 as described by Michaelson et al. (2011, supra) and as obtainable from Creative Biolabs (www.creativebiolabs.net—Cat. No: TAB-627CL), enavatuzumab (PDL192, as described in U.S. Pat. No. 9,056,908, incorporated by reference herein), BAY-356, TPP-2656 or other agonistic anti-Fn14 antibodies described in WO2015/189143 (incorporated by reference herein), 18D1 and ITEM4 (for review see: Cheng et al., Front Immunol. 2013; 4: 473).

The examples herein show that the efficacy of an agonistic ligand of Fn14/TWEAKR/TNFRSF12A is significantly increased if the ligand causes clustering of the Fn14/TWEAKR/TNFRSF12A receptor on the cell's surface. Receptor clustering is herein understood to refer to a process that results in grouping of a set of receptors at a cellular location, which usually amplifies the sensitivity of the receptors' signaling response. Preferably therefore, the agonistic ligand of Fn14 is a multivalent ligand of Fn14, wherein preferably the multivalent ligand causes clustering of Fn14 receptor molecules at the cell surface. A multivalent ligand of Fn14 is a ligand capable of binding at least two or more Fn14 receptor molecules and whereby the at least two or more Fn14 binding sites are physically, preferably covalently, linked. The multivalent ligand of Fn14 can thus be a multimer ora cluster of individual agonistic Fn14 ligands. In a preferred embodiment therefore, the agonistic anti-Fn14 antibody or agonistic fragment thereof preferably are in multimeric and/or clustered form, as can be achieved by methods known in the art, such as e.g. by using a clustering agent (e.g. Protein G) or by antibody engineering to increase the formation of antibody hexamers as e.g. described in WO2013/004842.

An agonistic TWEAK mimetic for use in accordance with the invention, such as an agonistic anti-Fn14 antibody or agonistic fragment thereof, preferably has a strong agonistic activity. The agonistic activity of an agonistic TWEAK mimetic can be determined by measuring the release of cytokines and/or chemokines in an in vitro cell growth assay. For example, as set forth in U.S. Pat. No. 9,056,908 incorporated by reference herein. For example in a typical assay the cells are incubated in vitro with an agonistic TWEAK mimetic+/−TWEAK ligand. Twenty four hours later, the cell supernatant is assessed for the presence of cytokines and/or chemokines using an ELISA assay or a commercial fluorescent bead-based multiplex assay (e.g., Luminex®, Upstate). Preferably, an IL-8 release assay as used in U.S. Pat. No. 9,056,908 is used to characterize the agonistic activity of the various agonistic TWEAK mimetic described herein. Using the data generated from an IL-8 assay, the percent agonist activity can be calculated using the formula: % agonist activity=(a-c)/(b-c); in which a=quantity of IL8 released from cells treated with agonistic TWEAK mimetic (e.g. antibody) at 10 µ/ml, b=quantity of IL8 released from cells treated with TWEAK at 300 ng/ml, c=quantity of IL8 released from untreated cells, and d=quantity of IL8 released from cells treated with TWEAK at 300 ng/ml and agonistic TWEAK mimetic (antibody) at 10 µ/ml. Alternatively, the agonistic activity of an agonistic TWEAK mimetic can be determined by measuring the NFkB2 p100 cleavage to p52 as described by Salzmann et al. (2013). For example, the cells are pretreated with increasing concentrations of an agonistic TWEAK mimetic (e.g. 0-3 µg/ml antibody+/−protein G) and then challenged overnight with a TWEAK ligand (e.g. 100 ng/ml Flag-TWEAK) to sensitize cells for TNF-induced apoptosis. On the next day, cells are challenged with TNF and cycloheximide, and after an additional overnight incubation, Triton X-100 lysates are prepared and analyzed by Western blotting with respect to cleavage of NFkB2 p100 to p52. Using the data generated from an NFkB2 p100 cleavage assay, the percent agonist activity can be calculated using the formula: % agonist activity=(a-c)/(b-c); in which a=quantity of p52 detected in cells treated with agonistic TWEAK mimetic (e.g. antibody) at 10 µ/ml, b=quantity of p52 detected in cells treated with TWEAK at 300 ng/ml, c=quantity of p52 detected in untreated cells, and d=quantity of p52 detected in cells treated with TWEAK at 300 ng/ml and agonistic TWEAK mimetic (antibody) at 10 µ/ml.

An agonistic TWEAK mimetic for use in accordance with the invention, such as an agonistic anti-Fn14 antibody or agonistic fragment thereof, preferably exhibits at least 25%, 30% 40%, 50% 60%, 70%, 80%, 90% or 100% agonist activity. In some embodiments, the agonistic TWEAK mimetic described herein can exhibit greater than 100% agonistic activity. Preferably, an agonistic TWEAK mimetic for use in accordance with the invention, has an agonistic activity that is at least equal to enavatuzumab. More preferably, the agonistic activity of the TWEAK mimetic is a factor 1.1, 1.2, 1.5, 2.0, 4.0, 8.0, 16, 32 or 64 higher than the agonistic activity of enavatuzumab as reference antibody.

In addition to the above-described use of the agonistic anti-Fn14 antibody as TWEAK-receptor agonist, in view of its broad and high tumor-associated expression and its multiple protumoral functions, Fn14 is an attractive antitumor target on two counts. First, stimulation (agonization) of Fn14 or TWEAK deprives tumor cells from beneficial Fn14-mediated activities and secondly, Fn14 might serve as a tumor-associated target for delivering of antibodies or antibody drug conjugates, irrespective of its tumor-related functions. In line with the latter, recent reports demonstrated antitumor effects of Fn14 antibodies that based on the activation of antibody effector functions, such as antibody-dependent cellular cytotoxicity (ADCC), or on the activity of antibody conjugated drugs (Culp et al. 2010 Clin Cancer Res 16(2):497-508; Michaelson et al., 2011, supra; Zhou et al., 2011 Mol Cancer Ther. 10(7):1276-88; Zhou et al, 2013 J Invest Dermatol 133(4):1052-62).

Antibody-associated ADCC activity of an agonistic anti-Fn14 antibody can be monitored and quantified through measurement of lactate dehydrogenase (LDH) release in the supernatant, which is rapidly released upon damage to the plasma membrane as e.g. described in U.S. Pat. No. 9,056,908 incorporated by reference herein. To determine the percentage of cell-mediated cytotoxicity, the average absorbance of a sample is calculated and background controls subtracted using the following equation:

$$Cytotoxicity\,(\%) = \frac{LDHrelease_{sample} - SR_{effector} - SR_{target}}{MR_{target} - SR_{target}} \times 100$$

SR refers to spontaneous release and MR refers to maximum release. See also, the methods disclosed in US Patent Application Pub. No. 2005/0025763; the disclosure of which is incorporated herein in its entirety. In some embodiments, the agonistic anti-Fn14 antibody induce at least 10%, 20%, 30%, 40%, 50%, 60%, or 80% cytotoxicity of the target cells. Suitable target cells can e.g. be SN12C renal cells as well as TweakR transfectant cell lines using either human peripheral blood mononuclear cells or mouse splenocytes as effector cells.

In some cases, the apoptotic TWEAK-TNF crosstalk might also be exploited for tumor therapy by triggering tumor cell death using recombinant TWEAK or agonistic Fn14-antibodies. In view of the poor serum half-life of recombinant TNF ligands and the additional Fc effector functions delivered by agonistic antibodies, the latter represents in this respect presumably the more practicable approach (Culp et al., 2010, supra; Michaelson et al., 2011, supra). See also Wajant (Cell Death Differ. 2015 November; 22(11): 1727-1741).

The immunotherapy of the cancer that is combined with the use of the TWEAK-receptor agonist in the treatment of the cancer in accordance to the invention preferably, comprises at least one of adoptive cell transfer (ACT) and immune checkpoint therapy. The ACT preferably comprises adoptive T-cell transfer, which preferably comprises at least one of: i) in vitro cultured T cells; and, ii) T cells that have been genetically modified to express a T cell receptor (TCR) or a chimeric antigen receptor (CAR) that recognizes a tumor specific antigen. Preferably, the transferred T cells are autologous T cells. Methods for genetically modifying T cells to express a TCR of desired specificity, using e.g. a retrovirus that contains a copy of a TCR gene to infect the T cells, are known in the art (see e.g. Morgan et al. 2006 Science. 314 (5796): 126-9; Hunder et al., 2008 N. Engl. J. Med. 358 (25): 2698-703). Methods for engineering CAR T cells are also known in the art (see e.g. Sadelain et al., 2013 Cancer Discovery. 3 (4): 388-98; Srivastava et al., 2015 Trends in Immunology. 36 (8): 494-502; Hartmann et al., EMBO Molecular Medicine. 9 (9): 1183-1197; and Zhang C et al., 2017 Biomarker Research. 5: 22). The in vitro cultured T cells can e.g. be tumor-infiltrating lymphocytes (TIL), preferably autologous TIL, that have been expanded in vitro in the presence of (a high dose of) IL-2 as has e.g. been described by Lizée et al. (2013 Annual Review of Medicine. 64 (1): 71-90) Besser et al. (2010 Clinical Cancer Research. 16 (9): 2646-55) Ellebaek et al. (2012 Journal of Translational Medicine. 10: 169) and Donia et al. (2013 J of Investigative Dermatology. 133 (2): 545-52). Well-known adoptive cell-based immunotherapeutic modalities, further include, without limitation, irradiated autologous or allogeneic tumor cells, tumor lysates or apoptotic tumor cells, antigen-presenting cell-based immunotherapy, dendritic cell-based immunotherapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

Thus in one embodiment, the immunotherapy of the cancer that is combined with the use of the TWEAK-receptor agonist in the treatment of the cancer in accordance to the invention is an immune checkpoint therapy. The term "immune checkpoint" refers to a group of molecules on the cell surface of $CD4^+$ and/or $CD8^+$ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4 (CD244), B7.1, B7.2, ILT-2, ILT-4, TIGIT, HHLA2, butyrophilins, IDO, CD39, CD73 and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM 005018.2 and NP_005009.2 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8).

PD-1 polypeptides are inhibitory receptors capable of transmitting an inhibitory signal to an immune cell to thereby inhibit immune cell effector function, or are capable of promoting costimulation {e.g., by competitive inhibition)

of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J Exp. Med. 192:1027-1034) and PD-L2 (Latchman et al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) Immunity 27: 111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) Immunity 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the CI-set within the Ig superfamily. Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1 S (SEQ ID NO: 4 in WO2018/14837, incorporated herein by reference). The second form is a cell-associated polypeptide, i.e., having a transmembrane and cytoplasmic domain, referred to herein as PD-L1 M (SEQ ID NO: 6 in WO2018/14837, incorporated herein by reference). The nucleic acid and amino acid sequences of representative human PD-L1 biomarkers regarding PD-L1 M are also available to the public at the GenBank database under NM_014143.3 and NP 054862.1.

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201: 1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain.

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

An "immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

In a preferred embodiment, the immune checkpoint therapy that is combined with the use of the TWEAK-receptor agonist in the treatment of the cancer in accordance to the invention, preferably, comprises the use (or administration) of at least one of an immune checkpoint blocking agent that blocks at least one of PD-1, PD-L1, PD-L2 and CTLA-4. Preferably, the immune checkpoint blocking agent is at least one of ipilimumab (anti-CTLA-4), nivolumab, pembrolizumab, antibody BGB-A31 (anti-PD-1) and atezolizumab (anti-PD-L1).

The inventors have found a synergistic effect between inhibition of TRAF2 and the use of a SMAC mimetic in the treatment of the cancer in accordance to the invention. In a further preferred embodiment, the use of the TWEAK-receptor agonist in the treatment of the cancer in accordance to the invention is therefore combined with the use of a SMAC mimetic. A SMAC (second mitochondrial-derived activator of caspases) mimetic is herein defined as an agent that triggers proteasomal degradation of cIAP1 and cIAP2 and are a novel group of anticancer drugs currently under investigation in clinical trials (for review see Fulda and Vucic, 2012, supra). Moreover, cell death induction by the non-death receptor TNFR2 and SMAC mimetics has also been traced back to the cooperative activity of endogenous TNF and depletion of cIAP1/2 and TRAF2 (Grell et al., 1999, EMBO J. June 1; 18(11):3034-43; Fulda and Vucic, 2012, supra). Thus, the TRAF2- cIAP1/2 based mechanisms underlying the Fn14-TNFR1 crosstalk are of general nature and are also of relevance for other TRAF2 interacting TNF receptors and SMAC mimetics. A preferred SMAC mimetic for use in the invention is the synthetic peptidomimetic birinapant (IUPAC name: (2S)—N-[(2S)-1-[(2R,4S)-2-[[6-fluoro-2-[6-fluoro-3-[[(2R,4S)-4-hydroxy-1-[(2S)-2-[[(2S) (methylamino)propanoyl]amino]butanoyl]pyrrolidin-2-yl] methyl]-1H-indol-2-yl]-1H-indol yl]methyl]-4-hydroxypyrrolidin-1-yl]-1-oxobutan-2-yl]-2-(methylamino)propanamide).

The Examples herein show that loss of TRAF2 is effective in the treatment of IFNγ receptor (IFNGR1)-deficient tumor systems, and thus provides an IFNγ-independent treatment. Therefore, in one embodiment of the use of the TWEAK-receptor agonist in the treatment of a cancer in accordance with the invention, the cancer comprises tumor cells with a defect in their IFNγ pathway. The invention, however, explicitly includes the use of the TWEAK-receptor agonist in the treatment of a cancer comprising IFNγ-proficient and IFNGR-proficient tumor cells.

TWEAK has been described in the art as a single agent against breast cancer cell lines, which themselves can make TNF. However most tumor cells, such as the melanoma and lung cancer cell lines used in the Examples herein, do not produce TNF by themselves. That is why, in order to see an effect of TWEAK on tumor cells that do not produce their own TNF, T cells (e.g. in a form of immunotherapy) are needed as a source of TNF. Hence, in one embodiment of the use of the TWEAK-receptor agonist in the treatment of a cancer in accordance with the invention, the cancer comprises tumor cells that do not produce TNF by themselves.

The investigators have found that no significant selective tumor pressure is observed for TNF pathway mutations in patients at baseline. However, they also found that both response duration and overall survival were lower for tumors that accumulated TNF pathway non-synonymous mutations after onset of immunotherapy, indicating a strong immune-editing selection against an intact TNF signaling pathway upon immunotherapy. These conclusions regarding the role of TNF in driving antitumor immunity derive from three clinical observations. First, we analyzed several patient cohorts before and on immune checkpoint blockade therapy (ICB). We observed that under baseline conditions, TNF is unlikely to have a strong cytotoxic effect on tumors, as neither TNF expression nor mutations in the TNF pathway have any prognostic power in that setting. Secondly, our data suggest that in patients responding to immunotherapy, TNF has an important role, as evidenced by the higher expression of TNF and TNF response signatures. Thirdly, we find clear evidence of immune editing in the TNF pathway in ICB-treated patients, highlighting the crucial role of TNF alongside IFNγ in T cell cytotoxicity in ICB-responsive patient tumors.

Therefore, in a preferred embodiment, the TWEAK-receptor agonist is used in accordance with the invention in the treatment of a tumor having at least one of: a low IFNγ response signature, a defect in the IFNγ pathway, a low IFNγ expression level, a low TNF expression level and a low TNF response signature.

A tumor with a low IFNγ-signature is herein defined as a tumor comprising cells with a mutation in and/or with reduced expression of at least one gene selected from the IFNγ gene-signature described by Ayers et al. (2017; see also Table S1), which gene-signature consists of the genes: IDO1, CXCL10, CXCL9, HLA-DRA, STAT1 and IFNG. Preferably, a low IFNγ response signature is defined as the expression of the (Ayers) IFNγ gene-signature observed in the lowest 50%, 60%, 70%, 73%, 75%, 80%, 85%, 89%, 90% or 95% of patients. More preferably, a low IFNγ response signature is defined as the expression of the (Ayers) IFNγ gene-signature observed in the lowest 81%, or the 81st percentile, of patients.

A tumor with a low IFNγ expression level is herein defined as a tumor having an IFNγ expression level as observed in the lowest 50%, 60%, 70%, 73%, 75%, 80%, 85%, 89%, 90% or 95% of patients. Preferably, a low IFNγ expression level is herein defined as a tumor having an IFNγ expression level as observed in the lowest 81%, or the 81st percentile, of patients A tumor with a defect in the IFNγ pathway is herein defined as a tumor having a mutation in at least one gene selected from the group consisting of MTOR, CAMK2D, IFNG, SOCS1, IFNGR1, CRKL, IL1B, SMAD7, MAP3K11, IRF9, PIAS4, STAT1, CREBBP, RAP1A, PIK3CA, PTPN2, JAK2, JAK1, PTPN11, MAPK1, IRF1, STAT3, MAP3K1, DAPK1, RAPGEF1, PTGES2, EP300, MAP2K1, PIK3R1, PIAS1, MAPK3, RAP1B, PRKCD, CAMK2B, CBL, CAMK2A, CAMK2G, CEBPB, AKT1, CASP1, wherein the mutation causes a defect in the IFNγ pathway.

A tumor with a low TNF expression level is herein defined as a tumor having a TNF expression level as observed in the lowest 50%, 60%, 70%, 75%, 78%, 81.5%, 85%, 90% or 95% of patients. Preferably, tumor with a low TNF expression level is herein defined as a tumor having a TNF expression level as observed in the lowest 81.5%, or the 81.5th percentile, of patients A tumor with a low TNF-signature is herein defined as a tumor comprising cells with a mutation in and/or with reduced expression of at least one gene selected from the TNF gene-signature PID_TNF_PATHWAY as given in Table S1, which gene-signature consists of the genes: TNF, MAP4K5, SMPD1, BAG4, TRAF1, RFFL, GNB2L1, NFKB1, STAT1, NSMAF, MAP3K5, TRADD, TAB2, IKBKB, PRKCZ, TNFAIP3, MAP4K4, TRAF2, RIPK1, CAV1, MAP3K3, PRKCI, BIRC3, IKBKG, CASP8, CHUK, FADD, MAP3K7, TXN, SQSTM1, MAP3K1, MAP4K3, MAP4K2, SMPD2, TAB1, MAP2K3, TNIK, NRK, MADD, MAP2K7, RELA, ADAM17, TNFRSF1B, CYLD, TNFRSF1A and BIRC2. Preferably, a low TNF response signature is defined as the expression of the TNF gene-signature observed in the lowest 50%, 60%, 70%, 75%, 78%, 81.5%, 85%, 90% or 95% of patients. More preferably, a low TNF response signature is defined as the expression of the TNF gene-signature observed in the lowest 81.5%, or the 81.5th percentile, of patients. Examples of patient tumors harboring TNF pathway mutations are provide in Table S2.

The expression levels of the signature genes can be determined using methods known in the art per se such as RT-qPCR, RNA sequencing or Nanostring analysis (NanoString Technologies, Inc.). Preferably, the expression level signature genes is determined in vitro in a sample of the tumor, e.g. obtained in a biopsy from the patient.

In a preferred embodiment of the invention, a TWEAK-receptor agonist as herein defined above is used in a treatment of cancer, wherein prior to the treatment the tumor is determined as having at least one of a low IFNγ response signature and a low TNF response signature.

In some embodiment, the TWEAK-receptor agonist is used in accordance with the invention in the treatment of a cancer, wherein the cancer comprises tumor cells with a mutation in a TNF pathway component.

In a further embodiment of the invention, a TWEAK-receptor agonist as herein defined above is used in a treatment of cancer to prevent or overcome resistance to an immunotherapy as herein defined above. The resistance to immunotherapy can be a primary resistance, an adaptive immune resistance or an acquired resistance as defined by Sharma et al. (2017). The TWEAK-receptor agonist can thus be used to prevent escape from immunotherapy, as may occur by downregulation of members of the IFN signalling pathway and/or TNF signalling pathway. Preferably, the TWEAK-receptor agonist is used in combination with a SMAC mimetic in the treatment for preventing resistance to or escape from the immunotherapy. In such treatments, the administration of the TWEAK-receptor agonist or its combination with the SMAC mimetic can precede and/or be simultaneous with the administration of the immunotherapy. The immunotherapy preferably is an immune checkpoint therapy as herein defined above.

In yet a further embodiment of the invention, a TWEAK-receptor agonist as herein defined above is used to treat a cancer comprising tumor cells that are or have become resistant to an immunotherapy as herein defined above. Preferably, the TWEAK-receptor agonist is used in combination with a SMAC mimetic in the treatment of a cancer that is or has become resistant to the immunotherapy. In such a treatment the TWEAK-receptor agonist or its combination with the SMAC mimetic can thus be applied to overcome the resistance of the cancer to the immunotherapy. In such treatments, the administration of the TWEAK-receptor agonist or its combination with the SMAC mimetic can be subsequent to a failed immunotherapy and can precede and/or be simultaneous with the administration of an immunotherapy subsequent to the failed therapy. The immunotherapy preferably is an immune checkpoint therapy as herein defined above.

In the cancer treatments of the invention, a TWEAK-receptor agonist as defined herein above, can be administered simultaneously, separately or sequentially with at least one of: a) the immunotherapy of the cancer; and, b) the SMAC mimetic.

For example, in one embodiment of the invention the TWEAK-receptor agonist may be used simultaneously, separately or sequentially with the immunotherapy, and simultaneously, separately or sequentially with the SMAC mimetic. When given separately or sequentially, the order of administration of the drugs can be for example that the immunotherapy is administered first, the SMAC mimetic is administered second, and the TWEAK-receptor agonist may be administered last. Any other order of administration of the drugs is also possible. In a preferred embodiment, the TWEAK-receptor agonist or its combination with the SMAC mimetic are administered first and the immunotherapy is administered last.

As explained above, the new use of the TWEAK-receptor agonist, the immunotherapy and the SMAC mimetic is not limited to combinations administered separately, but also includes the compositions obtained by physical association of the drugs and in either case a synergistic effect may be obtained. The skilled person will understand that any one of TWEAK-receptor agonists, the immunotherapy, and the SMAC mimetic may be administrated to the patient simultaneously, separately or sequentially from the other drugs. The treatment of the patient includes treatment in the first line or second line, or third line.

In yet another example, the TWEAK-receptor agonist, the immunotherapy and the SMAC mimetic are administered simultaneously. As used herein "simultaneous" administration refers to administration of more than one drug at the same time, but not necessarily via the same route of administration or in the form of one combined formulation. For example, one drug may be provided orally whereas the other drug may be provided intravenously during a patient's visit to a hospital.

In yet another example, the TWEAK-receptor agonist, the immunotherapy and the SMAC mimetic are administered separately. Separate administration includes the administration of the drugs in separate form and/or at separate moments in time, but again, not necessarily via the same route of administration.

In yet another example, the TWEAK-receptor agonist, the immunotherapy and the SMAC mimetic are administered sequentially. Sequentially indicates that the administration of a first drug is followed, immediately or in time, by the administration of the second drug, and so on.

Thus, in one embodiment of the invention, the TWEAK-receptor agonist is administered as a pretreatment of the immunotherapy of the cancer. Preferably, the TWEAK-receptor agonist and the SMAC mimetic are administered as a pretreatment of the immunotherapy of the cancer.

In some embodiment of the invention, a TWEAK-receptor agonist as herein defined above is used in a treatment of cancer, wherein the cancer is a solid tumor. Solid tumors that may be treated with the TWEAK-receptor agonist include, but are not limited to, adrenal cancers, bladder cancers, bone cancers, brain cancers, breast cancers (e.g., triple negative breast cancer), cervical cancers, colorectal cancers, endometrial cancers, esophageal cancers, eye cancers, gastric cancers, head and neck cancers, kidney cancers (e.g., advanced renal cell carcinoma), liver cancers (e.g., hepatocellular carcinoma, cholangiocarcinoma), lung cancers (e.g., non-small cell lung cancer, mesothelioma, small cell lung cancer), head and neck cancers, melanomas (e.g., unresectable or metastatic melanoma, advanced malignant melanoma), oral cancers, ovarian cancers, penile cancers, prostate cancers, pancreatic cancers, skin cancers (e.g., Merkel cell carcinoma), testicular cancers, thyroid cancers, uterine cancers, vaginal cancers, and tumors with evidence of DNA mismatch repair deficiency. The cancer may be newly diagnosed and naive to treatment, or may be relapsed, refractory, or relapsed and refractory, or a metastatic form of a solid tumor. In some embodiments, the solid tumor is selected from bladder cancer, breast cancer, head and neck cancer, kidney cancer, lung cancer, lymphoma, melanoma, and gastric cancer. In some embodiments, the solid tumor is selected from: melanoma (e.g., unresectable or metastatic melanoma), lung cancer (e.g., non-small cell lung cancer), and renal cell carcinoma (e.g., advanced renal cell carcinoma). In some embodiments, the solid tumor is selected from triple negative breast cancer, ovarian cancer, hepatocellular carcinoma, gastric cancer, small cell lung cancer, mesothelioma, cholangiocarcinoma, Merkel cell carcinoma and tumors with evidence of DNA mismatch repair deficiency.

In some embodiments of the invention, a TWEAK-receptor agonist as herein defined above is used in a treatment of cancer, wherein the cancer is a blood malignancy. The blood malignancy may be newly diagnosed and naive to treatment, or may be relapsed, refractory, or relapsed and refractory, or a metastatic form of a blood malignancy. Blood-borne malignancies that may be treated with a TWEAK-receptor agonist in accordance with the invention antibody include, but are not limited to, myelomas (e.g., multiple myeloma), lymphomas (e.g., Hodgkin's lymphoma, non-Hodgkin's lymphoma, Waldenstrom's macroglobulinemia, mantle cell lymphoma), leukemias (e.g., chronic lymphocytic leukemia, acute myeloid leukemia, acute lymphocytic leukemia), and myelodysplastic syndromes. In an alternative embodiment, a TWEAK-receptor agonist as herein defined above is used in a treatment of cancer, wherein the cancer is a cancer other than a myelodysplastic syndrome.

In one aspect, the invention thus pertains to a combination comprising a TWEAK-receptor agonist as defined herein and at least one of a) an immunotherapy of the cancer as defined herein; and, b) a SMAC mimetic as defined herein for use in the treatment of a cancer.

In a further aspect the invention pertains to a TWEAK-receptor agonist as defined herein above.

In another aspect, the invention relates to a pharmaceutical composition comprising one or more of a TWEAK-receptor agonist as defined herein above, a SMAC mimetic as herein defined above and an immunotherapeutic as herein defined above. The pharmaceutical composition further preferably comprises at least one pharmaceutically acceptable carrier. The pharmaceutically acceptable carrier such as an adjuvant, or vehicle, is for administration of the antibody or antibody fragment to a subject. Said pharmaceutical composition can be used in the methods of treatment described herein above by administration of an effective amount of the composition to a subject in need thereof. The term "subject", as used herein, refers to all animals classified as mammals and includes, but is not restricted to, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration (see e.g. "Handbook of Pharmaceutical Excipients", Rowe et al eds. 7th edition, 2012, www.pharmpress.com). The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter ions such as sodium; metal complexes (e.g. $Zn^{2+}$-protein complexes); and/or non-ionic surfactants such as TWEEN™, PLURONICS™ or polyethylene glycol (PEG).

The administration route of the TWEAK-receptor agonist, SMAC mimetic and/or immunotherapeutic according to the invention can be oral or parenteral. The term "parenteral" as used herein includes intravenous, intra-arterial, intralymphatic, intraperitoneal, intramuscular, subcutaneous, rectal or vaginal administration. The intravenous forms of parenteral administration are preferred. By "systemic administration" is meant oral, intravenous, intraperitoneal and intramuscular administration. The amount of the TWEAK-receptor agonist, SMAC mimetic and/or immunotherapeutic required for therapeutic effect will, of course, vary with the TWEAK-receptor agonist, SMAC mimetic and/or immunotherapeutic chosen, the nature and severity of the condition being treated and the patient. In addition, the TWEAK-receptor agonist, SMAC mimetic and/or immunotherapeutic may suitably be administered by pulse infusion, e.g., with declining doses of the TWEAK-receptor agonist, SMAC mimetic and/or immunotherapeutic. Preferably the dosing is given by injections, most preferably intravenous or subcutaneous injections, depending in part on whether the administration is brief or chronic.

Thus, in a particular embodiment, the pharmaceutical composition of the invention may be in a form suitable for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol or sodium chloride in the composition.

Prolonged absorption of the injectable compositions can be brought about by including in the composition an agent which delays absorption, for example, aluminium monostearate and gelatin.

Sterile injectable solutions can be prepared by incorporating the active compound (e.g. a TWEAK-receptor agonist, SMAC mimetic and/or immunotherapeutic) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC). Adequate excipients can be used, such as bulking agents, buffering agents or surfactants. The mentioned formulations will be prepared using standard methods for preparing parenterally administrable compositions as are well known in the art and described in more detail in various sources, including, for example, "Remington: The Science and Practice of Pharmacy" (Ed. Allen, L. V. 22nd edition, 2012, www.pharmpess.com).

It is especially advantageous to formulate the pharmaceutical compositions, namely parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, for the prevention and/or treatment of the diseases and disorders mentioned herein and depending on the specific disease or condition to be treated and its severity, the potency of the specific TWEAK-receptor agonist, SMAC mimetic and/or immunotherapeutic of the invention to be used, the specific route of administration and the specific pharmaceutical formulation or composition used, the TWEAK-receptor agonist, SMAC mimetic and/or immunotherapeutics of the invention will generally be administered in the range of from 0.001 to 1,000 mg/kg body weight/day, preferably about 0.01 to about 100 mg/kg body weight/day, most preferably from about 0.05 to 10 mg/kg body weight/day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

Aside from administration of a TWEAK-receptor agonist, SMAC mimetic and/or immunotherapeutic according to the invention to the patient, the present application contemplates administration of a TWEAK-receptor agonist, SMAC mimetic and/or immunotherapeutics by gene therapy.

The pharmaceutical compositions can be included in a container, pack, or dispenser together with instructions for administration.

The TWEAK-receptor agonist, SMAC mimetic and/or immunotherapeutics and pharmaceutical compositions of this invention may be used with other drugs to provide a combination therapy. The other drugs may form part of the same composition, or be provided as a separate composition for administration at the same time or at different time.

In yet another aspect, the invention pertains to a method for identifying a TWEAK-receptor agonist. The method preferably comprises the steps of: a) providing tumor cells presenting an antigen-MHC class I complex and lacking functional IFNγ signaling; b) contacting the tumor cells of step a) with at least one candidate agonist of interest; c) co-incubating the tumor cells obtained from step b) with CD8 T cells expressing a T cell receptor that recognizes the antigen-MHC class I complex presented by the tumor cells of step a); d) determining whether the tumor cells in step c) undergo programmed cell death, preferably as indicated by an induction of Caspase-3/7 activity over time; e) identifying a candidate agonist as a TWEAK-receptor agonist if in step d) the tumor cells are determined to undergo programmed cell death at a greater rate than: i) corresponding tumor cells contacted with the candidate agonist and co-incubated with CD8 T cells that do express the T cell receptor that recognizes the antigen-MHC class I complex presented by the tumor cells of step a); and/or, ii) corresponding tumor cells not contacted with the candidate agonist and co-incubated with CD8 T cells expressing the T cell receptor that recognizes the antigen-MHC class I complex presented by the tumor cells of step a).

Preferably, in the method, the tumor cells in step b) are further contacted with a SMAC mimetic, and in step e) the candidate agonist is further identified as a TWEAK-receptor agonist if in step d) the tumor cells are determined to undergo programmed cell death at a greater rate than: iii) corresponding tumor cells contacted with the candidate agonist without the SMAC mimetic and co-incubated with CD8 T cells expressing the T cell receptor that recognizes the antigen-MHC class I complex presented by the tumor cells of step a). More preferably, in the method the SMAC mimetic is birinapant.

In a preferred embodiment of the method, the tumor cells comprise cells of at least one HLA-A*02:01+/MART1+ melanoma cell line, and the CD8 T cells are CD8 T cells that are retrovirally transduced with a MART-1 specific T cell receptor. More preferably, the CD8 T cells are healthy donor CD8 T cells that are retrovirally transduced with a MART-1 specific T cell receptor.

Preferably, in the method for identifying a TWEAK-receptor agonist, a candidate agonist of interest is selected from the group consisting of a peptide, a peptidomimetic, an aptamer, a small molecule and an antibody. More preferably, in the method, libraries containing a plurality of such candidate agonists are tested for their ability to inhibit TRAF2.

Preferably, in the method for identifying a TWEAK-receptor agonist, the use of tumor cells that are IFNγ-proficient and IFNGR-proficient is not excluded.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

Figure 1A:
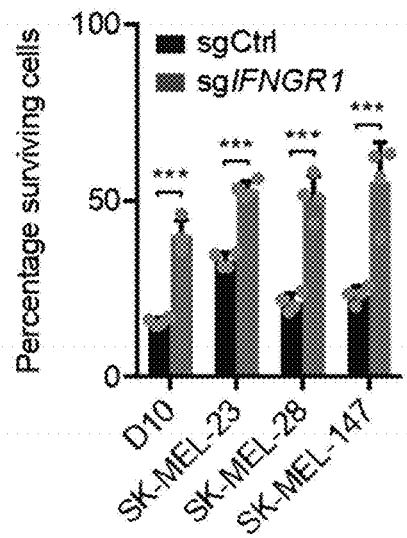
FIG. 1: TNF signaling dominates the IFNγ-independent CD8 T cell-associated tumor vulnerability landscape.
(A) Quantification of T cell cytotoxicity assays of the indicated IFNGR1-proficient and IFNGR1-deficient human melanoma cell lines after exposure to MART-1 T cells at a 1:2 ratio for all cell lines. Error bars indicate SD. Significance was determined using a Student's t test for each cell line. Representative of 3 experiments, each n=4.
(B) In vivo growth of IFNGR1-proficient and IFNGR1-deficient D10 human melanoma clones after adoptive cell transfer (ACT) of untransduced (control) CD8 T cells or MART-1 CD8 T cells in an NSG murine xenograft model. Error bars indicate SEM; n=4 mice per group.
(C) In vivo growth in C57BL/6 mice of D4M.3A-OVA murine melanoma cell lines harboring either sgIfngr1, sgB2m or a non-targeting control sgRNA. Error bars indicate SEM; n=10 mice per group. Significance was determined at day 24 using an ANOVA test with Tukey post hoc testing.
(D) Schematic overview of CRISPR-Cas9 knockout screen in IFNGR1-deficient D10 human melanoma cells.
(E) Logo-transformed MAGeCK robust ranking aggregation (RRA)-scores for either depletion (left) or enrichment (right) of sgRNAs in tumor cells challenged with MART-1 T cells versus control T cells.
(F) Loge-fold change of the individual sgRNAs counts (MART-1 T cells versus control T cells) targeting the genes identified in (E). sgRNAs targeting enriched and depleted genes are demarcated in red and blue, respectively.
(G) Competition assays of melanoma cells expressing sgRNAs as indicated upon control or MART-1 T cell challenge. Representative flow cytometry plots are shown (n=3).

(H) Quantification of the data in (G) and all other targeted genes. The change in ratio of a sgRNA targeting a hit versus sgCtrl is represented relative to melanoma cells challenged with control T cells ($\log_2$). Grey dots represent individual measurements (n=3), and error bars indicate SD. Significance was determined using a one-way ANOVA, followed by a Dunnett's multiple comparisons test.

$*p<0.05$; $p<0.01$; $*p<0.001$, $****p<0.0001$; see also FIG. 7.

FIG. 2: Important role for TNF in ICB-responding tumors but not in untreated tumors.
(A) Correlation between TNF expression and survival in TCGA. The y-axis represents the direction *-log 10 (p-value) of the correlation between TNF expression (1st versus 4th quartile) and survival (log-rank test; see Methods).
(B) Correlation between TNF pathway mutational status and survival in TCGA. The y-axis represents the direction *-$\log_{10}$ (p-value) of the correlation between TNF pathway mutational status and survival (log-rank test; see Methods).
(C) Quantification of surviving sgCtrl or sgTRAF2 melanoma cells after TNF treatment at indicated concentrations (representative of three individual experiments, each n=3). Results were significant at all tested concentrations, as determined by multiple Student's t tests and Bonferroni multiple testing correction.
(D) Normalized TNF expression for indicated patient populations in a cohort treated with anti-PD-1 (Roh et al., 2017). Significance was determined using a Student's t test to compare NR to R at each timepoint. Whiskers of the boxplots indicate 1.5× the interquartile ranges.
(E) Normalized TNF signature expression (PID_TNF_PATHWAY, see Methods) for indicated patient populations in a cohort treated with anti-PD-1 (Roh et al., 2017). Significance was determined using a Student's t test to compare NR to R at each timepoint. Whiskers of the boxplots indicate 1.5× the interquartile ranges.
(F) Analysis of the response duration in an ipilimumab-treated cohort (Snyder et al., 2014) as a function of the mutational status of the TNF pathway in samples that were obtained before (Pre) or after (Post) onset of anti-CTLA-4 treatment. A one-tailed t-test was applied to calculate significance (p=ns, 0.002662).
(G) Using cohort from (E) but representing overall survival in a Kaplan-Meier plot. A logrank test was performed to calculate the p-value (p=8.9×10-3, ns).
$p<0.05$; $p<0.01$; $*p<0.001$, $****p<0.0001$; see also FIG. 8 and Table S1 and S2.

FIG. 3: TRAF2 targeting poises cells to undergo RIPK1-dependent cell death in response to T cell-derived TNF.
(A) Induction of tumor cell apoptosis as measured by a Caspase-3/7 dye in polyclonal pools of sgCtrl or sg TRAF2-transduced D10 cells after MART-1 T cell challenge in the presence or absence of a neutralizing TNF antibody (representative of 3 replicates; each n=4). Statistical significance was determined using a Student's t test.
(B) As in (A), but for indicated cell lines the percentage of reduction of T cell-mediated killing (relative to ISO control) is represented. Data for each cell line is pooled for three independent replicates. Melanoma cell line names are highlighted in black text, a lung cancer cell line is highlighted in green text. Statistical significance was determined using a Student's t test.
(C) Quantification of crystal violet staining of D10 cells harboring sgRNAs targeting indicated TRAF family members after challenge with MART-1 T cells at a 1:16 T cell:tumor cell ratio (n=4). Error bars indicate SD. Statistical significance was determined using a one-way ANOVA with Dunnett post hoc testing.
(D) Western blot analysis of D10 cell lines carrying either a non-targeting control guide (sgCtrl) or a guide targeting TRAF2 (sgTRAF2) after exposure to MART-1 T cells for 0, 2 or 6 hours.
(E) Representative T cell cytotoxicity assay of D10 melanoma cell lines carrying combinations of non-targeting control guides (sgCtrl), a guide targeting TRAF2 (sgTRAF2) and a guide targeting RIPK1 (sgRIPK1) after exposure to MART-1 T cells in indicated T cell:tumor cell ratios (n=3).
(F) Quantification of crystal violet staining in (E), Error bars indicate SD. Statistical significance was determined using a one-way ANOVA with Sidak post hoc testing.
(G) Western blot analysis of D10 melanoma cells treated for 8 hours with indicated amounts of recombinant human TWEAK.
(H) Representative T cell cytotoxicity assay of D10 melanoma cells treated with 250 ng/mL TWEAK during exposure to MART-1 T cells in indicated T cell:tumor cell ratios (n=2).
(I) Western blot analysis of D10 melanoma cells treated for 8 hours with indicated amounts of enavatuzumab in the presence or absence of protein G.
(J) CellTiter-Blue quantification of a T cell cytotoxicity assay in TRAF2-proficient (left panel) and TRAF2-deficient (right panel) D10 cells treated with indicated reagents at a 1:8 T cell:tumor cell ratio (n=4). Error bars indicate SD. Statistical significance was determined using a one-way ANOVA with Dunnett post hoc testing.
$p<0.05$; $p<0.01$; $*p<0.001$, $****p<0.0001$.

FIG. 4: TRAF2 loss sensitizes to CD8 T cell-derived TNF in immune-proficient and ACT animal models
(A) In vivo growth of clonal wild-type and TRAF2-KO D10 cells after ACT with control or MART-1 T cells in an NSG murine xenograft model. Error bars indicate SEM; n=8 mice per group. Significance was determined using a Student's t test with Holm-Sidak correction for multiple comparisons.
(B) Kaplan-Meier survival curves of mice from (A). Mice were sacrificed after tumors reached 500 mm$^3$. Significance was determined using a Mantel-Cox test, using Holm-Sidak correction for multiple comparisons.
(C) In vivo growth of clonal wild-type and TRAF2-KO D10 cells after ACT with control or MART-1 T cells, in the presence or absence of an anti-TNF antibody in an NSG murine xenograft model. Error bars indicate SEM; n=8 mice per group.
(D) Fold change of tumor volumes from (C). Specifically, isotype-treated mice were compared to anti-TNF-treated mice harboring clonal wild-type or TRAF2-KO D10 cells after ACT with control or MART-1 T cells in an NSG murine xenograft model mice. All data was normalized to the average tumor volume of isotype-treated mice in each genotype. Statistical significance was determined using a Mann-Whitney U test.
(E) In vivo growth of polyclonal pools of sgCtrl or sg Traf2-transduced D4M.3A-OVA murine melanoma cells in NSG mice. Error bars indicate SEM; n=10 mice per group.
(F) In vivo growth of polyclonal pools of sgCtrl or sg Traf2-transduced D4M.3A-OVA murine melanoma cells in C57BL/6 mice. Error bars indicate SEM; n=10 mice per group. Significance was determined using a Mann-Whitney U test.

(G) Kaplan-Meier survival curves of mice from (E). Mice were sacrificed after tumors reached 500 mm$^3$. Significance was determined using a Mantel-Cox test, using Holm-Sidak correction for multiple comparisons.

FIG. 5: TRAF2 mutations in patients' tumors conferring T cell resistance (A) Expression of TRAF2 in tumor (red) and related normal tissue (white). Data are represented as $\log_2$ (RSEM) and were derived from TCGA. Significance was determined using a Student's t test per tissue type.

(B) Competition assays of melanoma cells overexpressing TRAF2 or controls cells upon control or MART-1 T cell challenge. The change in ratio of cells overexpressing TRAF2 versus an empty vector control upon MART-1 T cell challenge is represented relative to melanoma cells challenged with control T cells ($\log_2$-scale). Grey dots represent individual measurements (n=3), and error bars indicate SD. Statistical significance was determined using a Student's t test.

(C) Schematic representation of the location of patient-derived mutants and functional domains in the TRAF2 protein. The length of the bar for each mutation indicates its frequency. RING, Ring finger domain; T1, TRAF type 1 domain; T2, TRAF2 type 2 domain; MATH, meprin and TRAF homology domain (D) Competition assays of melanoma cells expressing TRAF2 variants as indicated upon control or MART-1 T cell challenge. The change in ratio of a TRAF2 mutant versus wild-type TRAF2 upon MART-1 T cell challenge is represented relative to melanoma cells challenged with control T cells ($\log_2$-scale). Grey dots represent individual measurements (n=3), and error bars indicate SD. Significance was determined using one-way ANOVA with Dunnett multiple comparisons test.

(E) The relative frequency of HLA-A/B/C or B2M mutations in patients that do or do not harbor inactivating TRAF2 mutations. Significance was determined using Fisher's exact test.

$p<0.05$; $p<0.01$; *$p<0.001$, ****$p<0.0001$; see also FIG. 9.

FIG. 6. TRAF2/cIAP complex inhibition in vivo increases susceptibility of melanoma to CD8 T cells and cooperates with anti-PD-1

(A) Tumor cell survival in MART-1 T cell cytotoxicity assays of polyclonal pools of sgCtrl or sgTRAF2-transduced melanoma (black) or lung cancer (green) cell lines in the absence or presence of birinapant. Data for all cell lines were normalized to their respective no T cell condition, and then normalized to their respective non-targeting sgRNA controls (n=3 independent replicates). Error bars indicate SD. Tumor cell lines are subdivided in groups of single agent efficacy (significant difference in sgCtrl+DMSO vs. sgCtrl+Bir or sgTRAF2+DMSO, p<0.001), TRAF2 KO efficacy (significant difference in sgCtrl+DMSO vs. sgTRAF2+DMSO only, p<0.001) and combinatorial efficacy (significant difference in sgCtrl+DMSO vs. sgTRAF2+Bir only, p<0.001). The difference in sgTRAF2+DMSO vs. sgTRAF2+Bir is significant for all cell lines (p<0.001). Significance was determined using a one-way ANOVA with a Tukey post-hoc analysis for multiple comparisons.

(B) Induction of tumor cell apoptosis as measured by a Caspase-3/7 dye after control or MART-1 T cell attack on polyclonal pools of sgCtrl or sg TRAF2-transduced SK-MEL-23 cells in the presence or absence of a neutralizing TNF antibody and with or without birinapant (representative of 3 replicates; n=4). Error bars indicate SEM. Statistical significance was determined using a Student's t test.

(C) As in (B), but for indicated cell lines the percentage of reduction of T cell-mediated killing (relative to ISO control) is represented. Data for each cell line is pooled for three independent replicates. Melanoma cell line names are highlighted in black text, lung cancer cell line names are highlighted in green text. Statistical significance was determined using a one-way ANOVA with Dunnett's multiple comparisons test.

(D) (Left) In vivo growth of TRAF2-deficient and TRAF2-proficient BLM clones in an NSG murine xenograft model after ACT with MART-1 T cells in the presence of birinapant or vehicle. Error bars indicate SEM; n=10 mice per group. (Middle) Best change in tumor volume after ACT in mice from left panel. If tumors were progressive, the first tumor measurement after ACT was taken as best change in tumor volume. Whiskers of the boxplots indicate 1.5× the interquartile ranges. (Right) Survival curves of mice from left panel. Mice were sacrificed after tumors reached 1000 mm$^3$. Significance was determined using a Mantel-Cox test, using Holm-Sidak correction for multiple comparisons.

(E) (Left) In vivo growth of TRAF2-deficient and TRAF2-proficient BLM clones in an NSG murine xenograft model of the human BLM cell line after ACT with MART-1 T cells in the presence of birinapant or vehicle and in the presence or absence of anti-PD-1 antibodies. Significance of difference in tumor volumes at indicated timepoints was determined using a one-way ANOVA with Tukey post hoc testing and Student's t test. (Right) Survival curves of mice in left panel. Mice were sacrificed after tumors reached 1000 mm$^3$. Significance was determined using a Mantel-Cox test, using Holm-Sidak correction for multiple comparisons.

$p<0.05$; $p<0.01$; *$p<0.001$, ****$p<0.0001$; see also FIG. 10.

FIG. 7: Analysis and extended validation of genome-wide CRISPR-Cas9 KO screen in IFNGR1-deficient melanoma cells, Related to FIG. 1.

(A) An IFNGR1-deficient D10 clone was compared to wild-type melanoma cells for IFNGR1-staining and induction of PD-L1 induction upon IFNγ-treatment (25 ng/mL). Representative FACS plots of 3 independent experiments.

(B) Representative T cell cytotoxicity assays of the indicated IFNGR1-proficient and IFNGR1-deficient human melanoma cell lines after exposure to MART-1 T cells.

(C) Inter-replicate correlation was determined for all samples as measured by the Pearson correlation coefficient.

(D) $\log_{10}$-transformed gene-level MaGeCK RRA scores of a comparison of the control T cell-treated sample relative to the library reference control to identify essential genes. Previously identified essential genes are demarcated in blue.

Figure 1B:
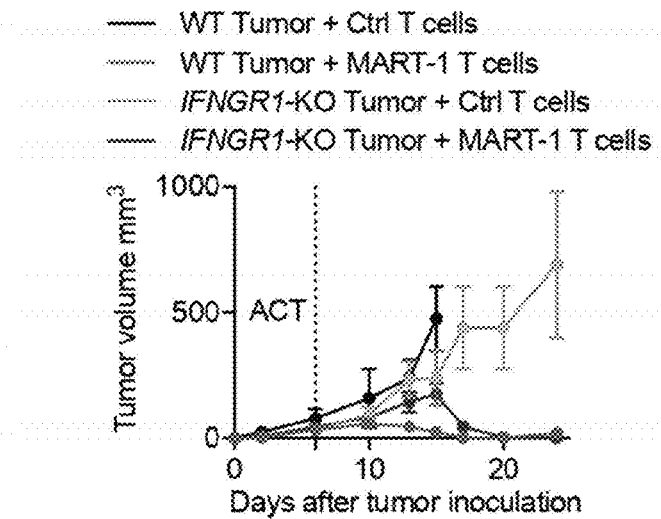
Figure 1C:
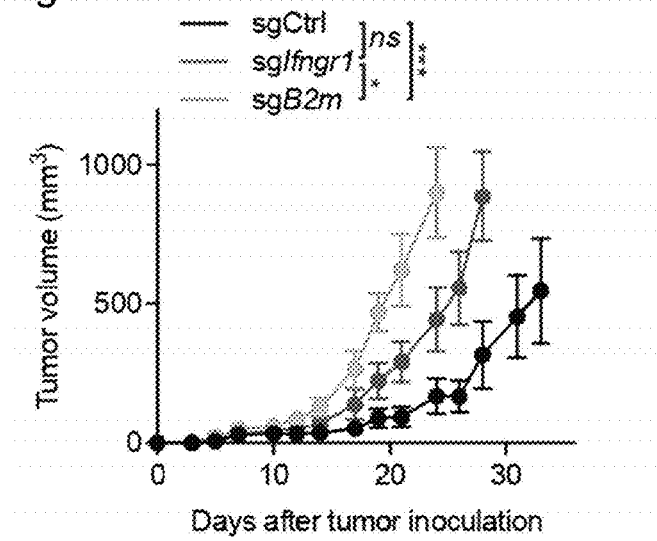
Figure 1D:
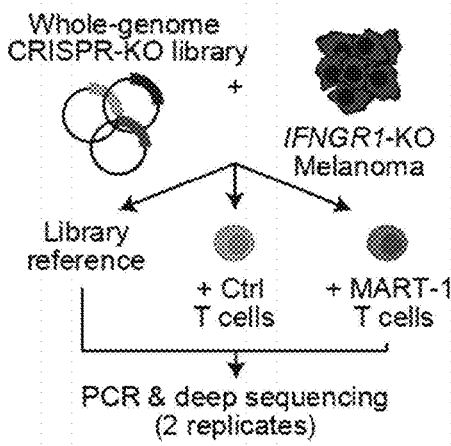
Figure 1E:
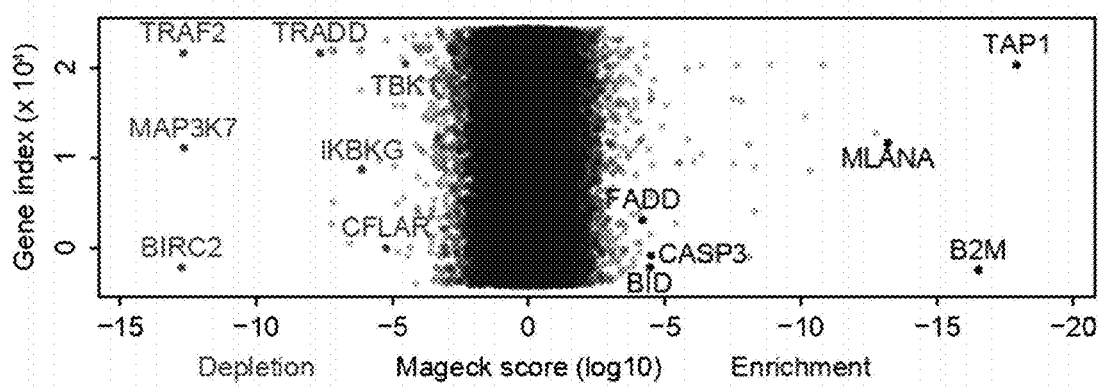
Figure 1F:
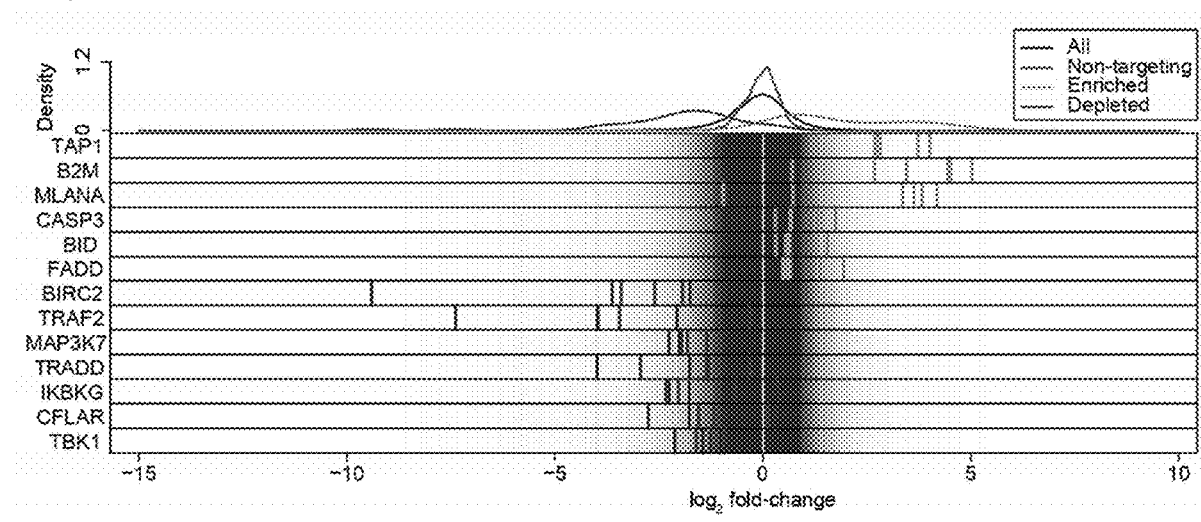

(E) Gene set enrichment analysis for the KEGG_ANTIGEN_PROCESSING_AND_PRESENTATION, SANA_RESPONSE_TO_IFNG_UP, PLASARI_TGFB1_TARGETS_10HR_UP, PID_TNF_PATHWAY and PID_TRAIL_PATHWAY genesets, based on enriched and depleted genes in FIG. 1E.

(F) Quantification of MART-1 T cell cytotoxicity assay of polyclonal pools of IFNGR1-KO D10 melanoma cells expressing sgCtrl or sgRNAs targeting hits. Data is normalized to the amount of killing in a non-targeting guide condition. Dots represent individual sgRNAs, and statistically significant (p<0.05) sgRNAs are demarcated in blue (n=4). Statistical significance was determined using a one-way ANOVA with Dunnett multiple comparisons test.
(G) As in (F) but using an independently derived IFNGR1-KO D10 clone.
(H) Representative images of enrichment and depletion by sgB2M and sgTRAF2 of the experiments in (F).
(I) Representative images of enrichment and depletion by sgB2M and sgTRAF2 of the experiments in (G).
(J) MART-1 T cell cytotoxic assay of polyclonal pools of IFNGR1-proficient D10 melanoma cells expressing sgCtrl or sgTRAF2, and which were or were not reconstituted with TRAF2. sgTRAF2 does not target the overexpression construct.
(K) Western blots of cells used in (J).
$p<0.05$; $p<0.01$; *$p<0.001$, ****$p<0.0001$.

FIG. 8: Extended analyses regarding the role of TNF in immune responses, Related to FIG. 2.
(A) RNA expression of cytokines in CD8 T cells after tumor co-culture. The dotted red line indicates the division between high and low expressed cytokines respectively. Expression is represented as $log_2$-transformed values of normalized read counts (counts per million (cpm)+1)
(B) Bioinformatic flow chart for the identification of T-cell derived cytokines mediating tumor cell signaling.
(C) Expression of gene sets identified in (B) per cell line. Arrow indicates progression over time (0, 4, 14 hours of co-culture from left to right).
(D) Gene set enrichment analysis (GSEA) plots of cytokine gene sets of samples from (B) upon MART-1 T cell challenge.
(E) Expression of a proteome-derived TNF signature after either MART-1 T cell attack or TNF treatment as a function of time (n=3). Whiskers of the boxplots indicate 1.5× the interquartile ranges.
(F) Pearson correlation matrix of the expression of CD8A, cytolytic score and gene sets identified in (F) in the TCGA human skin cutaneous melanoma (SKCM) cohort.
(G) TNF expression in a cohort of patients (Riaz et al., 2017) treated with anti-PD-1 blocking antibodies before (Pre) or after (Post) onset of therapy. Patient cohorts were split up in those responding (R) and not responding (NR) to their therapy. Significance was determined using a Mann-Whitney test to compare NR to R at each timepoint. Whiskers of the boxplots indicate 1.5× the interquartile ranges.
(H) As in (C) but expression of a TNF response signature geneset (PID_TNF_PATHWAY, see Methods).
(I) IFNγ signature expression for indicated patient populations in a cohort treated with anti-PD-1 (Riaz et al., 2017). Significance was determined using a Mann-Whitney test to compare NR to R at each timepoint. Whiskers of the boxplots indicate 1.5× the interquartile ranges.
(J) IFNγ signature expression for indicated patient populations in a cohort treated with anti-PD-1 (Roh et al., 2017). Significance was determined using a Student's t test to compare NR to R at each timepoint. Whiskers of the boxplots indicate 1.5× the interquartile ranges.
(K) As in FIG. 2G, but for a different patient cohort (Roh et al., 2017).
(L) As in FIG. 2F, but for IFNγ pathway mutations.
(M) As in FIG. 2G, but for IFNγ pathway mutations.
$p<0.05$; $p<0.01$; *$p<0.001$, ****$p<0.0001$.

Analysis and extended validation of genome-wide CRISPR-Cas9 KO screen in IFNGR1-deficient melanoma cells, Related to FIG. 2
(A) Logo-transformed gene-level MaGeCK RRA scores of a comparison of the control T cell-treated sample relative to the library reference control to identify essential genes. Previously identified essential genes are demarcated in blue.
(B) Inter-replicate correlation was determined for all samples as measured by the Pearson correlation coefficient.
(C) Gene set enrichment analysis for the KEGG_ANTIGEN_PROCESSING_AND_PRESENTATION gene set, based on enriched genes in FIG. 2B.
(D) Gene set enrichment analysis for the SANA_RESPONSE_TO_IFNG_UP, PLASARI_TGFB1_TARGETS_10HR_UP, PID_TNF_PATHWAY and PID_TRAIL_PATHWAY gene sets, based on depleted genes in FIG. 2B.
(E) Quantification of MART-1 T cell cytotoxicity assay of polyclonal pools of IFNGR1-KO D10 melanoma cells expressing sgCtrl or sgRNAs targeting hits. Data is normalized to the amount of killing in a non-targeting guide condition. Dots represent individual sgRNAs, and statistically significant (p<0.05) sgRNAs are demarcated in blue (n=4).
(F) As in (F) but using an independently derived IFNGR1-KO D10 clone.
(G) Representative images of enrichment and depletion by sgB2M and sgTRAF2 of the experiments in (F).
(H) Representative images of enrichment and depletion by sgB2M and sgTRAF2 of the experiments in (G).
(I) Analysis of the response duration in an ipilimumab-treated cohort as a function of the mutational status of the IFNγ pathway in samples that were obtained post-ipilimumab treatment. A one-tailed t-test was applied to calculate significance (p=0.2449, ns).
(J) As in (I), but representing overall survival in a Kaplan-Meier plot (post-ipilimumab biopsies only). A logrank test was performed to calculate the p-value (p=0.38, ns).
$p<0.05$; $p<0.01$; *$p<0.001$, ****$p<0.0001$.

FIG. 9: Clustering of Fn14-targeted agonistic antibodies sensitize to T cell-derived TNF, Related to FIG. 3.
(A) Expression of TNFRSF12A in tumor (red) and related normal tissue (white). Data are represented as $log_2$ (RSEM) and were derived from TCGA.
(B) Expression of TNFRSF12A in normal skin, primary melanoma and melanoma metastases. Data are represented as $log_2$ (RSEM) and were derived from GTEx and TCGA respectively. Significance was determined using a one-way ANOVA with Dunnet post-hoc testing.
(C) As FIG. 3J, but in SK-MEL-147.
(D) As in FIG. 3J, but in the presence or absence of an anti-TNF antibody and at a T cell:tumor cell ratio of 1:8.
$p<0.05$; $p<0.01$; *$p<0.001$, ****$p<0.0001$.

FIG. 10: Extended analyses regarding responses to TNF of TRAF2 patient variants, Related to FIG. 5.
(A) Western blot analysis of expression of TRAF2 in cells overexpressing TRAF2 or harboring patient mutations from FIG. 5B, D.
(B) Immunoblot of biotin-TNF co-immunoprecipitated proteins. The top panel shows the input for all samples used for the co-immunoprecipitation, the bottom panel shows the precipitated proteins.
(C) Western blot analysis of cell lines used in FIG. 5D after exposure to T cells for 6 hours.

Figure 5A:
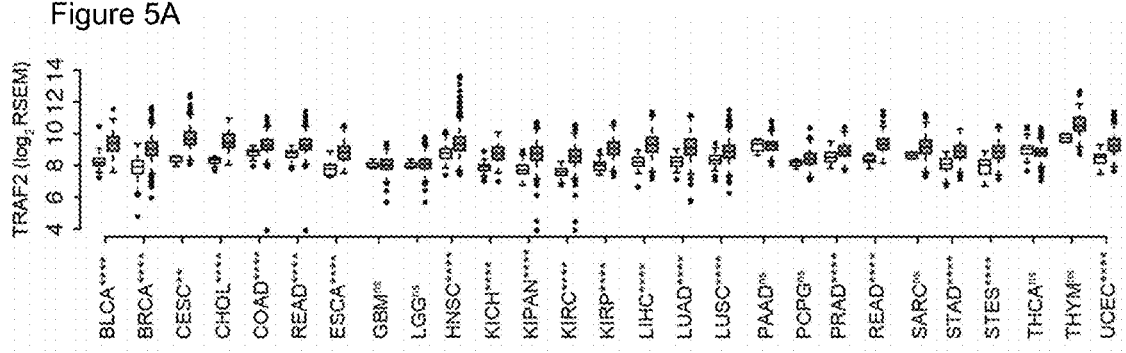
Figure 5B:
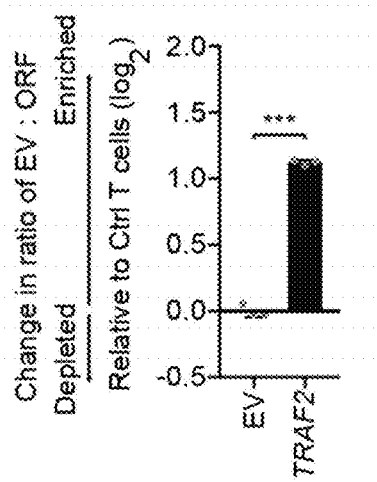
Figure 5C:
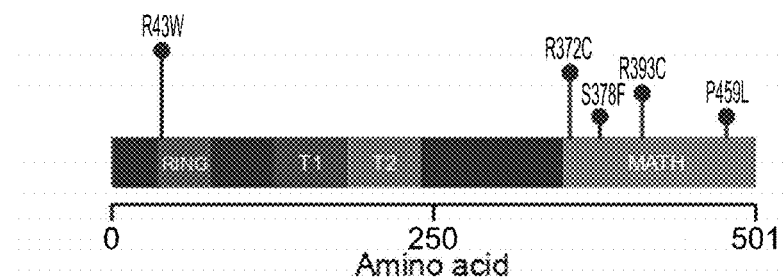
Figure 5D:
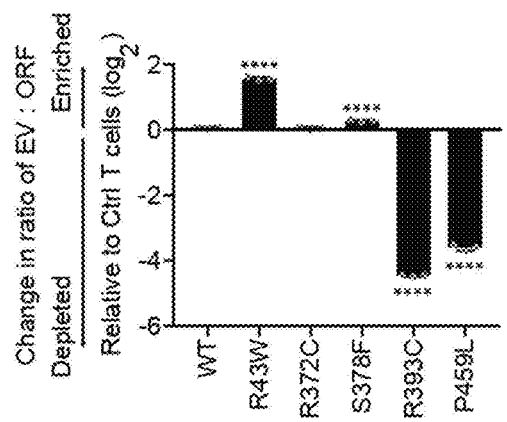
Figure 5E:
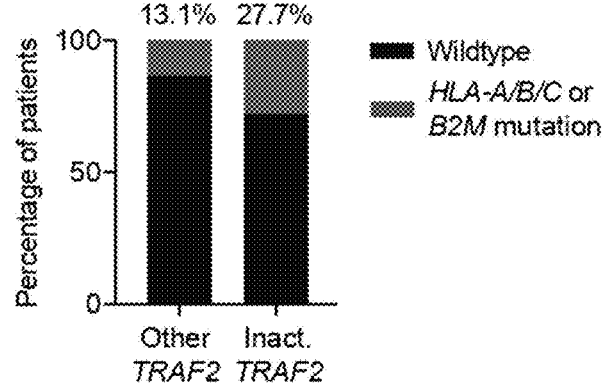

(D) Mutational load of patient tumors discussed in FIG. 5E. Significance was determined using a Mann-Whitney test. p<0.05; p<0.01; *p<0.001, ****p<0.0001.

FIG. 11: Additional data for the synergy between TRAF2 inactivation and Birinapant treatment, Related to FIG. 6.
(A) Western blotting of cell lines in FIG. 6A to confirm successful TRAF2 targeting.
(B) Quantification of MART-1 T cell cytotoxicity assay of polyclonal pools of D10 cells expressing sgRNAs as indicated. Error bars indicate SD (n=4).
(C) Western blot analysis of polyclonal pools of sgCtrl or sgTRAF2-expressing SK-MEL-23 melanoma cells in the presence or absence of birinapant, and upon co-culture with MART-1 T cell for indicated amounts of time.
(D) Quantification of MART-1 T cell cytotoxic assay of polyclonal pools of sgCtrl or sgTRAF2-transduced D10 cells with or without birinapant. All data were normalized to their respective no T cell condition (n=3). Error bars indicate SEM.
(E) Representative T cell cytotoxicity assay of polyclonal pools of sgCtrl or sgTRAF2-transduced SK-MEL-23 after challenge with MART-1 T cells in the presence or absence of birinapant.
(F) Representative T cell cytotoxicity assay of a BLM VVT clone and a BLM TRAF2 KO clone after challenge with MART-1 T cells in the presence or absence of birinapant.
(G) Growth curves of the individual tumors in FIG. 6D. The average is indicated in darker colour, and dotted line indicates the time of ACT.
(H) As in FIG. 6D (right panel), but using control T cells.
(I) TNF protein concentration of tumors from mice in FIG. 6E. Data was normalized to tumor weight of input. Statistical significance was determined using a Kruskal-Wallis test using Tukey multiple comparison correction. p<0.05; p<0.01; *p<0.001, ****p<0.0001.

EXAMPLES

Example 1

Experimental Model and Subject Details
Cell Lines and Primary Cultures

The BLM, SK-MEL-147, D10, SK-MEL-23, SK-MEL-28, A375, Me1888, A875 and HEK293T cell lines were all obtained from the Peeper laboratory cell line stock. The M032.X2.CL and M026.X1.CL cell lines are PDX-derived cell lines that were generated in-house (Boshuizen et al., 2018). The HCC827 and HCC4006 lung cancer cell lines were obtained from ATCC. The LCLC-103H lung cancer cell line was obtained from DSMZ. The D4M.3A murine melanoma cell line was a kind gift from Constance Brinckerhoff. Cell line identities were authenticated by means of STR profiling (Promega) and were regularly confirmed to be mycoplasma-free by PCR(Young et al., 2010). Human cell lines that lacked endogenous HLA-A201 or MART-1 expression were transduced with lentiviral constructs encoding for both missing components. D4M.3A was made to express the ovalbumin antigen by lentiviral introduction of a construct that encodes ovalbumin. All cell lines were maintained in DMEM (Gibco) containing 9% fetal bovine serum (Sigma), 100 units per ml of penicillin and 100 µg per ml of streptomycin (both Gibco). Primary CD8 T cells were isolated from buffycoats, which were taken from healthy donor blood (Sanquin). All donors gave written consent.

In Vivo Animal Studies

All animal studies were approved by the animal ethics committee (AEC) of the Netherlands Cancer Institute (NKI) and performed in concordance with ethical and procedural guidelines established by the NKI and Dutch legislation. Both male and female mice, of either C57BL/6 (Janvier) or NSG-B2m (The Jackson Laboratory) mouse strains were used at an age of 8-12 weeks.

Method Details
Isolation and Generation of MART-1 TCR CD8 T Cells

MART-1 TCR retrovirus was produced in a packaging cell line as described before (Gomez-Eerland et al. 2014). Peripheral blood mononuclear cells (PBMCs) were isolated from fresh, healthy donor buffycoats (Sanquin, Amsterdam, the Netherlands) by means of density gradient centrifugation using Lymphoprep (Stem Cell Technologies). After the PBMC fraction was isolated, CD8 T cells were purified using CD8 Dynabeads (Thermo Fisher Scientific) following manufacturer's instructions. The isolated CD8 cells were activated for 48 hours on a non-tissue culture treated 24-well plate that was pre-coated overnight with αCD3 and αCD28 antibodies (eBioscience, 16-0037-85 and 16-0289-85, 5 µg per well) at $2 \times 10^6$ per well. $2 \times 10^6$ Activated CD8 T cells were harvested and mixed 1:1 with MART-1 TCR retrovirus and spinfected on a Retronectin coated (Takara, 25 µg per well) non-tissue culture treated 24-well plate for 2 hours at 2000g. 24 hours after spinfection, MART-1 T cells were harvested and cultured for 7 days, after which MART-1 TCR expression was confirmed by means of flow cytometry (BD Pharmingen, α-mouse TCR β chain, 553172). CD8 T cells were initially maintained in RPMI (Gibco) containing 10% human serum (One Lamda), 100 units per ml of penicillin, 100 µg per ml of streptomycin, 100 units per ml IL-2 (Proleukin, Novartis), 10 ng per ml IL-7 (ImmunoTools) and 10 ng per ml IL-15 (ImmunoTools). After retroviral transduction, cells were maintained in RPMI containing 10% fetal bovine serum and 100 units per ml IL-2.

Bioinformatic and RNA Sequencing Analysis

Figure 7A:
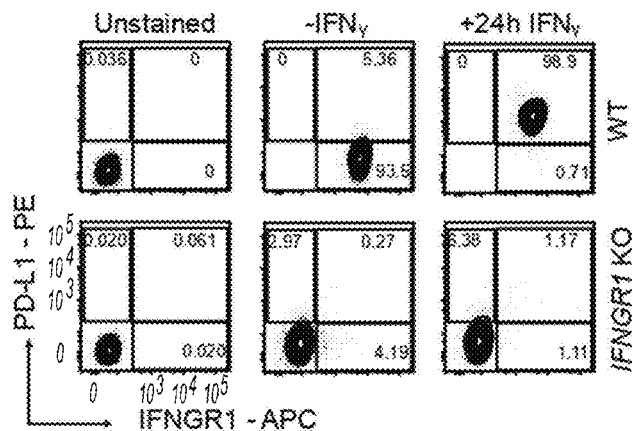
Figure 7B:
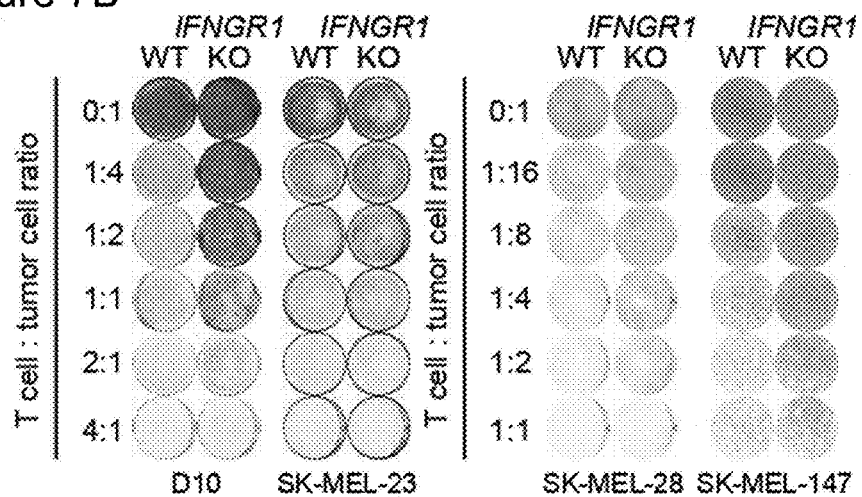
Figure 7C:
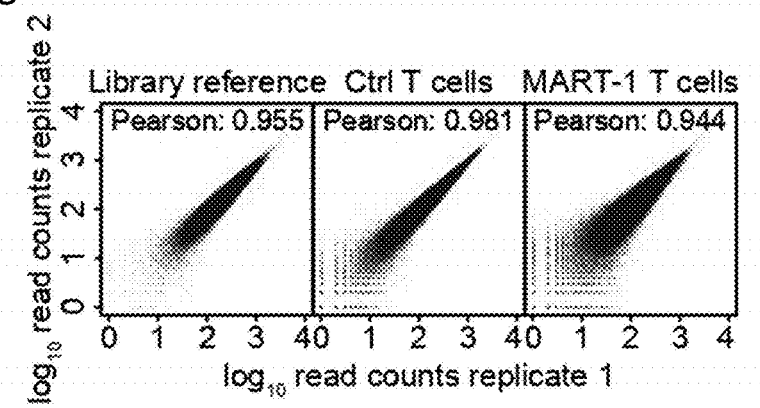
Figure 7D:
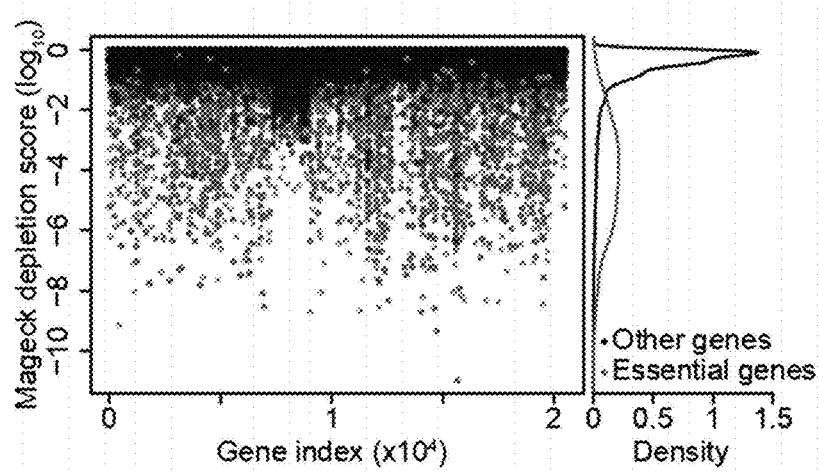

RNA sequencing count data were normalized and $\log_2$-transformed as $\log_2$ ((count+1) per million; referred to as $\log_2$ (cpm)), or using the rlog-transformation as implemented in DESeq2 (version 1.16.1 (Love et al., 2014)). For determining highly expressed cytokines (FIG. 7A), a cutoff of $\log_2$ (cpm)>7 was chosen. Cytokines were filtered based on whether essential cytokine receptors were expressed ($\log_2$ (cpm)>0.1; FIG. 7A-D). Gene set enrichment analysis (GSEA) was performed using the javaGSEA application (version 2.2.3) using the Spearman's rank correlation coefficient with T cell cytotoxicity over time as a metric for preranking, and using the C2-CP sub-collection from MSigDB (Subramanian et al., 2005; FIG. 7D). GSEA plots were redrawn using the replotGSEA function from the Rtoolbox package (https://github.com/PeeperLab/Rtoolbox). For correlation analysis on the TCGA SKCM data (FIG. 7F), and to calculate expression of gene sets upon T cell co-culture (FIG. 7D), $\log_2$ (cpm)-values were summed for all genes in the indicated gene sets to obtain its correlation or relative expression in a given sample. For FIGS. 2D, E and FIGS. 7G-J, raw read counts from RNA sequence data of patients treated with anti-PD-1 therapy were downloaded from the NCBI GEO database (GSE91061; Riaz et al., 2017). The raw read counts were normalized using the rlog-transformation as implemented in DESeq2 (version 1.16.1 (Love et al., 2014)). Normalized Nanostring data of patients with anti-PD-1 therapy were available from the supplementary data of an earlier publication (Roh et al., 2017). Differences in expression between responders (SD/PR/CR) and non-responders (PD) was assessed for TNF and PID_TNF_PATHWAY gene set in both datasets. The average expression levels for the PID_TNF_PATHWAY gene set was calculated using the z-scores for the genes from the gene set that could be matched to the available datasets. For FIGS. 2F, G, mutations in the PID_TNF_PATHWAY gene set were used to determine the mutational status of the TNF pathway. Analysis for FIGS. 7L, M were performed in an analogous manner as for FIGS. 2F, G, but for mutations in the PIF_IFNG_PATHWAY. Analysis for FIG. 7K were performed in an analogous manner as for FIG. 2G, but for a different patient cohort (Roh et al., 2017). For FIGS. 2A and 2B, log-rank p-values were calculated for differences in survival based on TNF expression (1st versus 4th quartile) and on mutational status of the TNF pathway as defined by the gene set PID_TNF_PATHWAY. Correlation of these metrics with survival are expressed as direction (expressed as 1 for correlation or −1 for anticorrelation)*-$\log_{10}$ (p-value). For the gene expression analyses in Figure S3A and FIG. 5A, healthy tissue and tumor data was downloaded from TCGA by using FireBrowse. For gene expression analysis in Figure S3B, healthy tissue and tumor data was downloaded from GTEx and TCGA databases respectively. For the proportion of HLA-A/B/C or B2M mutations in all patients and patients carrying either other or inactivating TRAF2 mutations (FIG. 5E, FIG. 10D), TCGA data was used. Mutations in TRAF2 were considered inactivating when they resulted in a frameshift, or when they were either R393C or P459L. Patients with mutated alleles were compared to all TCGA cases. To determine significance, a Fisher exact test was performed.

Proteomic Analyses

Cell pellets were lysed in a 1% sodium deoxycholate lysis buffer as described previously (Post et al., 2017). Proteins were digested overnight with Lys-C (1:75) and trypsin (1:25) at 37 degrees Celsius. Samples were acidified and desalted using C18 cartridges on the AssayMap BRAVO Platform (Agilent Technologies). Samples were dried and resuspended in 50 mM HEPES buffer and labeled with 10-plex TMT reagent (Thermo Scientific). Labeled samples were mixed equally, desalted using Sep-Pac C18 cartridges (Waters), and fractionated on a high-pH reversed-phase C18 column (Kinetex 5u Evo C18 100A, 150×2.1 mm, Phenomenex) coupled to an Agilent 1100 series HPLC over a 60 min gradient. For each biological replicate, fractions were concatenated to 20 fractions for proteome analysis and further pooled to 6 fractions for phosphoproteome enrichment. Phosphoproteome samples were enriched using Fe(III)-IMAC cartridges on the AssayMap BRAVO platform (Agilent Technologies) following the method described previously (Post et al., 2017). Samples were analyzed by nanoLC-MS/MS on a Q Exactive HF-X mass spectrometer (Thermo Scientific) equipped with an Agilent 1290 LC system with an LC gradient of 65 min (15% to 45% B) for proteome fractions and a 95 min gradient (9% to 35% B) for phosphoproteome fractions (Post et al., 2017). MS settings were as follows: full MS scans (375-1500 m/z) were acquired at 60,000 resolution with an AGC target of $3\times10^6$ charges and max injection time of 20 milliseconds. HCD MS2 spectra were generated for the top 12 precursors using 45,000 resolution, $1\times10^5$ AGC target, a max injection time of 80 milliseconds, a fixed first mass of 120m/z, and a normalized collision energy of 32%. MS2 isolation windows were 0.7 Th for proteome samples and 1.2 Th for phosphoproteome samples. Raw data files were processed with Proteome Discover 2.2 (Thermo Scientific) using a Sequest HT search against the Swissprot human database. Results were filtered using a 1% FDR cut-off at the protein and peptide level. TMT fragment ions were quantified using summed abundances with PSM filters requiring a S/N≥10 and an isolation interference cut off of 35% or 50% (proteome or phosphoproteome). Normalized protein and peptide abundances were extracted from PD2.2 and further scaled and analyzed using Perseus software (ver. 1.5.6.0). To obtain the proteome-derived TNF signatures (FIG. 7E), the limma package (version 3.34.3; Ritchie et al., 2015) was used to determine peptides that are higher expressed in cells treated for 4 hours with TNF relative to untreated cells (adjusted p-value cutoff: 0.001; adjustment method: fdr). Scaled protein and phosphopeptide abundances were median-normalized, and TNF signature expression was calculated by summing all normalized expression values of the proteins and phosphopeptides in the signature.

In Vitro Cytotoxicity Assays $1.2\times10^5$ tumor cells were seeded per well in 12-well culture plates (Greiner). CD8 T cells were admixed in serial dilutions (two-fold, starting at a 1:1 ratio). After 24 hours, T cells were washed away. After a further 4 days, plates were fixed and stained for 1 hour using a crystal violet solution containing 0.1% crystal violet (Sigma) and 50% methanol (Honeywell). For quantification, remaining crystal violet was solubilized in 10% acetic acid (Sigma). Absorbance of this solution was measured on an Infinite 200 Pro spectrophotometer (Tecan) at 595 nm. In select experiments, tumor viability data was assessed with CellTiter-Blue (Promega) following manufacturer's instructions. In indicated experiments, 1 uM of birinapant (Selleck Chemicals) in DMSO (Sigma) was added during co-cultures. For Incucyte (Incucyte Zoom, Essen Bioscience) experiments, $5\times10^3$ tumor cells were seeded per well in 96-well culture plates (Greiner). CD8 T cells were admixed in indicated ratios and a Caspase-3/7 dye (Essen Bioscience) was added. Growth of these co-cultures was followed for 48 hours. In indicated experiments a neutralizing TNF antibody or isotype control (R&D Systems, AF375 and Cell Signaling Technology, 7321 and 3900 respectively) was added at a concentration of 1 µg per ml. In indicated experiments, enavatuzumab (indicated concentrations; Creative Biolabs) in the presence or absence of protein G (50 µg/mL; Thermo Fisher Scientific) was added. To cluster enavatuzumab, cells were pretreated for 1 hour with enavatuzumab, then protein G was added for a further 7 hours. Then, CD8 T cells were added to the tumor cells for a further 16 hours. Instead of CD8 T cells, in indicated experiments 100 ng per ml recombinant TNF (Peprotech) or recombinant TWEAK (Peprotech) at indicated concentrations was added. To perform a dose-response with TNF, 400 ng/mL of TNF was added to melanoma cells as the highest dilution; this was then diluted down in two-fold steps.

Lentiviral Transductions and CRISPR-Mediated Knockouts sgRNAs targeting proteins of interest were cloned into lentiCRISPR-v2 (Addgene). HEK293T cells were transfected with lentiCRISPR-v2 and the packaging plasmids psPAX and pMD2.G (both Addgene) using polyethylenimine. After 24 hours, medium was replaced by OptiMEM (Gibco) containing 2% fetal bovine serum. After a further 24 hours, lentivirus-containing supernatant was harvested, filtered and stored for further use at −80° C. For lentiviral transduction, $5\times10^5$ tumor cells were seeded per well in a 12-well plate (Greiner) and lentivirus was added. After 24 hours, cells were selected with antibiotics for at least 7 days. Double knockouts were generated by using both a puromycin-selectable and blasticidin-selectable variant of lentiCRISPR-v2 for each sgRNA. To establish clonal knockout cell lines, tumor cells were transfected with lentiCRISPR-v2 and clones were generated by limiting dilution or soft-agar colonies were picked. To generate IFNGR1-deficient cell lines, tumor cells were transfected with lentiCRISPR-v2 and FACSorted three times based on lack of expression of CD119 (Miltenyi Biotech, 130-099-921). Clonal cell lines were derived from these IFNGR1-deficient cell lines by means of limiting dilution.

Flow Cytometry

Cells were stained with antibodies targeting surface molecules of interest according to manufacturer's instructions and analyzed on a Fortessa flow cytometer (BD Bioscience). Antibodies against IFNGR1 (130-099-921, Miltenyi Biotech) and PD-L1 (12-5983-42, eBioscience) were used.

Animal Studies

For xenograft studies, $1\times10^6$ D10 or BLM tumor cells were admixed with Matrigel (Corning) and injected subcutaneously into NSG-$\beta2M^{null}$ mice (The Jackson Laboratory). Growth was monitored three times per week with calipers, and tumor size was calculated using the following formula: ½×length (mm)×width (mm). When tumors reached indicated sizes, mice were randomized over different treatment groups in a blinded fashion and were administered $5\times10^6$ human CD8 T cells, intravenously in the tail vein. In vivo persistence of T cells was stimulated by administering 100.000 U IL-2 (Proleukin, Novartis) intraperitoneally daily for three consecutive days. In selected experiments, birinapant (MedChem Express) was administered intraperitoneally once every three days. Birinipant was formulated at 3 mg/ml in 12.5% captisol (CyDex Pharmaceuticals) in water adjusted to pH 4 with hydrochloric acid. In selected experiments the TNF blocking antibody infliximab (Slotervaart Hospital) was given twice weekly (10 mg/kg). In selected experiments, the PD-1-blocking antibody nivolumab (Slotervaart Hospital) was given once weekly (5 mg/kg). For studies in immunocompetent mice, $3\times10^5$ D4M.3A cells were injected subcutaneously into C57Bl/6J mice (Janvier) and tumor growth was monitored three times per week with calipers. All experiments ended for individual mice either when the tumor volume exceeded 1000 mm³, when the tumor showed ulceration, in case of serious clinical illness, when the tumor growth blocked the movement of the mouse, or when tumor growth assessment had been completed.

Immunoblotting

Cells were lysed in RIPA buffer (50 mM TRIS pH 8.0, 150 mM NaCl, 1% Nonidet P40, 0.5% sodium deoxycholate, 0.1% SDS) supplemented with complete protease inhibitor cocktail (Roche Applied Science) and phosphatase inhibitors 10 mM NaF, 1 mM Na3VO4, 1 mM sodium pyrophosphate and 10 mM beta-glycerophosphate. Protein concentration was determined using a Bradford Protein Assay (Biorad). Western blotting was performed by conventional techniques using 4-12% Bis-Tris polyacrylamide-SDS gels (Life Technologies) and nitrocellulose membranes (GE Healthcare). Blots were blocked in 4% milk powder and 0.2% Tween in PBS and then incubated overnight with primary antibodies. Western blots were then incubated in SuperSignal West Dura Extended Duration Substrate (Thermo Scientific) and luminescence was captured on high performance autoradiography films (Amersham). For co-immunoprecipitation experiments, $1\times10^7$ cells per condition were treated with 100 ng/mL biotin-labeled TNF (R&D Systems) or unlabeled TNF (Peprotech) for 10 minutes. Cells were then harvested and lysed in IP lysis buffer (30 mM Tris-HCl pH 7.4, 120 mM NaCl, 2 mM EDTA, 2 mM KCl, 1% Triton X-100 and supplemented with complete protease inhibitor cocktail). Active TNF receptor complexes were then precipitated by means of streptavidin-coated magnetic beads (Thermo Fisher) for 1 hour at 4° C. Precipitate was eluted from the beads by boiling at 95° C. in 1×LDS sample buffer. Immunoblotting was then performed as per above. Primary antibodies against cIAP1 (AF8181, R&D Systems), cIAP2 (3130, Cell Signaling Technology), Caspase 3 (9665, Cell Signaling Technology), TRAF2 (ab126758, Abcam), cleaved Caspase 3 (9664, Cell Signaling Technology), Caspase 8 (4790, Cell Signaling Technology), cleaved Caspase 8 (9748, Cell Signaling Technology), RIPK1 (3493, Cell Signaling Technology), Vinculin (4650, Cell Signaling Technology), α-Tubulin (T9026, Sigma), TNF-R1 (sc-8436, Santa Cruz) and phospho-STAT1 (9177, Cell Signaling Technology) were used. Horseradish peroxidase-conjugated secondary antibodies against mouse IgG (G21040, Thermo Scientific), rabbit IgG (G21234, Invitrogen) and goat IgG (811620, Thermo Fisher) were used.

Whole-Genome Screen

An IFNGR1-deficient clonal melanoma cell line derived from D10 was lentivirally transduced with lentiCas9-Blast (Addgene) and infected in duplicate at a coverage of 2000× with the GeCKO whole-genome knockout library (Addgene) at an infection rate of 30%. Three days after infection, a t=0 library reference sample was taken. After a further 11 days of puromycin (1 μg per ml; Sigma) selection, each replicate was treated with either control T cells or MART-1 T cells. Each replicate was treated with CD8 T cells from an independent donor. After 24 hours of co-culture, plates were washed twice with PBS (Gibco) and medium was replaced. After a further 4 days of culture, the remaining melanoma cells were harvested. 18% and 21% of cells survived the T cell challenge in each respective replicate, indicating a coverage at time of harvesting of >1000×. After harvesting, DNA was isolated from the melanoma cells by use of a Blood and Cell Culture MAXI kit (Qiagen). sgRNA sequences were then amplified by PCR using NEBNext High-Fidelity 2×PCR Master Mix (New England BioLabs) and following manufacturer's instructions. The following primers were used:

```
Gecko Forward,
5'-AATGATACGGCGACCACCGAGATCTACACTCTTTCCCTACACGA

CGCTCTTCCGATCTNNNNNNNGGCTTTATATATCTTGTGGAAAGGACG

AAACACC-3';

Gecko Reverse,
5'-CAAGCAGAAGACGGCATACGAGATCCGACTCGGTGCCATTTTTC

AA-3'.
```

The stretch of N nucleotides indicates a unique 6 nucleotide barcode used to identify each sample in deep sequencing. After PCR, the amplified guide sequences were pooled equimolarly. The pooled guide sequences were then identified by deep sequencing. For this, the generated amplicons were analyzed on an Illumina HiSeq 2500 Sequencing system (Illumina). Obtained sequence reads were aligned to the Gecko A and B libraries and counts per sgRNA were generated, where reads containing mismatches in common and sgRNA sequence were excluded for analysis. Enrichment and depletion at the sgRNA and gene level were determined using the Mageck algorithm (version 0.5.6; Li et al., 2014). To determine depletion of essential genes, the control T cell samples were compared with the t=0 library reference samples, and a core essential gene set derived from the intersect of three essentialome studies (Blomen et al., 2015; Hart et al., 2015; Wang et al., 2015) was used to demarcate essential genes (Figure S1D). Enrichment and depletion of genes in the MART-1 T cell samples was determined relative to control T cell samples (FIG. 1E, F). Gene set enrichment analysis was performed using the javaGSEA application (version 2.2.3, Subramanian et al., 2005) using the $\log_{10}$-transformed negative RRA score minus the $\log_{10}$-transformed positive score as a metric for preranking, and using the C2-CP sub-collection from MSigDB (Subramanian et al., 2005) (Figure S1E). GSEA plots were redrawn using the replotGSEA function from the Rtoolbox package (https://github.com/PeeperLab/Rtoolbox).

Competition Assays

Cells containing guides of interest were labeled with either either the CellTrace CFSE Cell Proliferation Kit (CFSE; Thermo Scientific) or the CellTrace Violet Cell Proliferation Kit (CTV; Thermo Scientific) following manufacturer's instructions. Labeled cells were mixed in a 1:1 ratio and seeded at a density of $4\times10^6$ melanoma cells per 10 cm plate (Greiner). Labeled cells were then challenged once, at a 1:2 ratio, or three times, at a 1:8 ratio, with either MART-1 T cells or control T cells. 24 hours after the last T cell challenge, remaining melanoma cells were analyzed for CFSE and CTV staining by flow cytometry.

Cytokine Measurements

Intratumoral cytokine measurements were performed using the Human TNF Flex set (BD Biosciences), generally following manufacturer's instructions, with the exception of using tumor lysate as input (1 mg per sample). To prepare lysates, snapfrozen tumor piecesd were weighed and lysed in RIPA buffer (50 mM TRIS pH 8.0, 150 mM NaCl, 1% Nonidet P40, 0.5% sodium deoxycholate, 0.1% SDS) supplemented with complete protease inhibitor cocktail (Roche Applied Science) and phosphatase inhibitors 10 mM NaF, 1 mM Na3VO4, 1 mM sodium pyrophosphate and 10 mM beta-glycerophosphate. Protein concentration was determined using a Bradford Protein Assay (Biorad).

Quantification and Statistical Analysis

Statistics

To compare multiple groups of data to one control condition, we performed a one-way ANOVA, followed by a Dunnett's test to correct for multiple comparisons. For Incucyte data, selected comparisons were made by one-way ANOVA followed by Sidak multiple comparisons test. In vivo data was compared by two-tailed unpaired Student t test with Holm-Sidak multiple testing correction when data was normally distributed or by two-tailed Mann-Whitney test with Bonferroni correction for multiple comparisons when data was not normally distributed. Normality was determined by Shapiro-Wilk test. Survival analyses were performed by Log-Rank Mantel-Cox test, followed by Holm-Sidak multiple testing correction. Exceptions to these approaches are listed in the corresponding figure legends. Analyses were performed by Prism (Graphpad Software Inc., version 7.0c) or in R. Unless otherwise indicated, a P value of lower than 0.05 was regarded as being statistically significant.

Data and Software Availability

Data Resources

All data presented in this manuscript can be obtained from the short-read archive (SRA) database using accession number SRP132830. The proteomics data was submitted to ProteomeXchange under the identification number PXD008995.

| KEY RESOURCES TABLE | | |
|---|---|---|
| REAGENT or RESOURCE | SOURCE | IDENTIFIER |
| Antibodies | | |
| CD3 | eBioscience | 16-0037-85 |
| CD8 | eBioscience | 16-0289-85 |
| α-mouse TCR β chain | BD Pharmingen | 553172 |
| Neutralizing TNF antibody | CellSignaling Technology | 7321 |
| Neutralizing TRAIL antibody | R&D Systems | AF375 |
| Isotype for Neutralizing antibodies | CellSignaling Technology | 3900 |
| CD119 | Miltenyi Biotech | 130-099-921 |
| HLA-A2 | BD Bioscience | 551285 |
| PD-L1 | eBioscience | 12-5983-42 |
| cIAP1 | R&D Systems | AF8181 |
| cIAP2 | CellSignaling Technology | 3130 |
| Caspase 3 | CellSignaling Technology | 9665 |
| TRAF2 | Abcam | Ab126758 |
| Cleaved Caspase 3 | CellSignaling Technology | 9664 |
| Caspase 8 | CellSignaling Technology | 4790 |
| Cleaved Caspase 8 | CellSignaling Technology | 9748 |
| RIPK1 | CellSignaling Technology | 3493 |
| Vinculin | CellSignaling Technology | 4650 |
| Tubulin | Sigma | T9026 |
| Phospho-STAT1 | CellSignaling Technology | 9177 |
| Chemicals, Peptides, and Recombinant Proteins | | |
| Caspase-3/7 dye | Essen Bioscience | 4440 |
| TRAIL | ITK Diagnostics | 4354 |

KEY RESOURCES TABLE

| REAGENT or RESOURCE | SOURCE | IDENTIFIER |
| --- | --- | --- |
| TNF | Peprotech | 300-01A |
| Matrigel | Corning | 356230 |
| Captisol | CyDex Pharmaceuticals | RC-0C7-100 |
| CFSE | Thermo Scientific | C34554 |
| CTV | Thermo Scientific | C34557 |
| Retronectin | Takara | T100B |
| IL-2 | Slotervaart Hospital | Proleukin |
| IL-7 | Immunotools | 11340075 |
| IL-15 | Immunotools | 11340155 |
| Lymphoprep | StemCell Technologies | 07861 |
| Crystal Violet | Sigma | V5265 |
| Birinapant | MedChem Express | HY-16591 |
| Critical Commercial Assays | | |
| CD8 Dynabeads | Thermo | 11147D |
| STR profiling kit | Promega | B9510 |
| 10-plex TMT reagent | Thermo | 90406 |
| Bradford Protein Assay | Bio-Rad | 5000006 |
| SuperSignal West Dura Extended Duration Substrate | Thermo Scientific | 34075 |
| NEBNext High Fidelity 2x PCR Master Mix | New England Biolabs | M0541L |
| Deposited Data | | |
| RNA sequencing Data | | SRP132830 |
| Proteomics | | PXD008995 |
| Experimental Models: Cell Lines | | |
| 888-mel | Internal stock | N/A |
| A375 | Internal stock | N/A |
| A875 | Internal stock | N/A |
| BLM | Internal stock | N/A |
| D10 | Internal stock | N/A |
| HCC4006 | ATCC | CRL-2871 |
| HCC827 | ATCC | CRL-2868 |
| LCLC103-H | DSMZ | ACC 284 |
| M026.X1.CL | Internally generated | N/A |
| M032.X2.CL | Internally generated | N/A |
| SK-MEL-147 | Internal stock | N/A |
| SK-MEL-23 | Internal stock | N/A |
| SK-MEL-28 | Internal stock | N/A |
| D4M.3A | Constance Brinckerhoff | N/A |
| HEK293T | Internal stock | N/A |
| Experimental Models: Organisms/Strains | | |
| NSG-β2M$^{null}$ mice | The Jackson Laboratory | 010636 |
| C57Bl/6J mice | Janvier | C57BL/6JRj |
| Oligonucleotides | | |
| Sequencing Primer, Gecko Forward, 5'-AATGATACGGCGACCACCGAGATCTACACTCTTTCCCTACACGACGCTCTTCCGATCTNNNNNNGGCTTTATATATCTTGTGGAAAGGACGAAACACC-3'; | | N/A |
| Sequencing Primer, Gecko Reverse, 5'-CAAGCAGAAGACGGCATACGAGATCCGACTCGGTGCCATTTTTCAA-3' | | N/A |
| B2M sgRNA 1, CGTGAGTAAACCTGAATCTT | | N/A |
| B2M sgRNA 1, CGTGAGTAAACCTGAATCTT | | N/A |
| B2M sgRNA 2, CAGTAAGTCAACTTCAATGT | | N/A |
| BIRC2 sgRNA 1, ATATCCTCATCTTCTTGAAC | | N/A |
| BIRC2 sgRNA 1, ATATCCTCATCTTCTTGAAC | | N/A |
| BIRC2 sgRNA 2, GGCTTGAGGTGTTGGGAATC | | N/A |
| BIRC2 sgRNA 3, ACATCATCATTGCGACCTTC | | N/A |
| BIRC2 sgRNA 4, TGTTTGCTGCGCCCGCACTG | | N/A |
| BIRC2 sgRNA 5, ATGATGCTATGTCAGAACAC | | N/A |
| BIRC3 sgRNA 1, TCTACTAAAGCCCATTTCCA | | N/A |
| BIRC3 sgRNA 2, GGTAACTGGCTTGAACTTGA | | N/A |
| BIRC3 sgRNA 3, GAGAGTTTGAATAAGAGCCA | | N/A |
| CFLAR sgRNA 1, GTTTCTCCAACTCAACCACA | | N/A |
| CFLAR sgRNA 1, GTTTCTCCAACTCAACCACA | | N/A |
| CFLAR sgRNA 2, GGGCCGAGGCAAGATAAGCA | | N/A |
| Human non-targeting control sgRNA 1, GGTTGCTGTGACGAACGGGG | | N/A |

-continued

| KEY RESOURCES TABLE | | |
|---|---|---|
| REAGENT or RESOURCE | SOURCE | IDENTIFIER |
| Human non-targeting control sgRNA 2, GGTTGCTGTGACGAACGGGG | | N/A |
| Human non-targeting control sgRNA 3, GCACGAGGTGAACAGCCGCT | | N/A |
| IFNGR1 sgRNA 1, CGAACGACGGTACCTGAGGA | | N/A |
| IKBKG sgRNA 1, TCAGGAGCGCCCTGTTCTGA | | N/A |
| IKBKG sgRNA 2, CTCACCGACCCTCCAGAGCC | | N/A |
| KBKG sgRNA 1, TCAGGAGCGCCCTGTTCTGA | | N/A |
| MAP3K7 sgRNA 1, AGAGCCTGATGACTCGTTGT | | N/A |
| MAP3K7 sgRNA 1, AGAGCCTGATGACTCGTTGT | | N/A |
| MAP3K7 sgRNA 2, GATGGAGTTATCTGATCCAT | | N/A |
| Mouse B2m sgRNA 1, ACTCTGGATAGCATACAGGC | | N/A |
| Mouse non-targeting control sgRNA 1, GTATTACTGATATTGGTGGG | | N/A |
| Mouse Traf2 sgRNA 1, TAACGCTGCCCGCAGAGAGG | | N/A |
| RIPK1 sgRNA 1, GAGAGTGCAGAACTGGACAG | | N/A |
| RIPK1 sgRNA 2, AGCGCGACACGGAGACTAGG | | N/A |
| RIPK1 sgRNA 3, CTTCCTCTATGATGACGCCC | | N/A |
| TBK1 sgRNA 1, ATCACTTCTTTATTCCTACG | | N/A |
| TBK1 sgRNA 1, ATCACTTCTTTATTCCTACG | | N/A |
| TBK1 sgRNA 2, GAAGAACCTTCTAATGCCTA | | N/A |
| TRADD sgRNA 1, TCCCTCGCGCTCGTACTCGT | | N/A |
| TRADD sgRNA 1, TCCCTCGCGCTCGTACTCGT | | N/A |
| TRADD sgRNA 2, CACCGAGTGCTGGGCGAGCG | | N/A |
| TRAF1 sgRNA 1, ATGGCTACAAGTTGTGCCTG | | N/A |
| TRAF1 sgRNA 2, AGGAAGCCGTCTTCGAACTC | | N/A |
| TRAF1 sgRNA 3, CACCGTCTGCCAGGACCCAA | | N/A |
| TRAF2 sgRNA 1, CCTGCAGAAACGTCCTCCGC | | N/A |
| TRAF2 sgRNA 1, CCTGCAGAAACGTCCTCCGC | | N/A |
| TRAF2 sgRNA 2, ATATATGCCCTCGTGAACAC | | N/A |
| TRAF2 sgRNA 2, CCTGCGGAGGACGTTTCTGC | | N/A |
| TRAF2 sgRNA 3, ACCGAATGTCCCGCGTGCAA | | N/A |
| TRAF2 sgRNA 3, GCGGAGGACGTTTCTGCAGG | | N/A |
| TRAF2 sgRNA 4, GCCTTTGCACGCGGGACATT | | N/A |
| TRAF2 sgRNA 4, GGGGACCCTGAAAGAATACG | | N/A |
| TRAF2 sgRNA 5, GGGGACCCTGAAAGAATACG | | N/A |
| TRAF2 sgRNA 6, ATATATGCCCTCGTGAACAC | | N/A |
| TRAF2 sgRNA 7, CCTGCGGAGGACGTTTCTGC | | N/A |
| TRAF2 sgRNA 8, CCTGCAGAAACGTCCTCCGC | | N/A |
| TRAF3 sgRNA 1, AGACACCGACTGTCCCTGCG | | N/A |
| TRAF3 sgRNA 2, GGAGAAGGCGTGTAAATACC | | N/A |
| TRAF3 sgRNA 3, ACACTTGTACTTGTCCTCCA | | N/A |
| TRAF4 sgRNA 1, TCCTGGAGAAGCCCAAGCGA | | N/A |
| TRAF4 sgRNA 2, CCCCCAGATCTACCCAGACC | | N/A |
| TRAF4 sgRNA 3, AGTGTGCAGGTAGATCACGG | | N/A |
| TRAF5 sgRNA 1, ATTCTGGGCCGGTACCAGGT | | N/A |
| TRAF5 sgRNA 2, AGTGCCGGGAGCCAGTCCTA | | N/A |
| TRAF5 sgRNA 3, TAGAGTACCAGTTTGTGGAG | | N/A |
| TRAF6 sgRNA 1, ACATTCTGAAGGATTGTCCA | | N/A |
| TRAF6 sgRNA 2, GATTCTACACTGGCAAACCC | | N/A |
| TRAF6 sgRNA 3, GAAGCAGTGCAAACGCCATG | | N/A |
| TRAF7 sgRNA 1, ACTCCTTCAGGCCCTCGAAG | | N/A |
| TRAF7 sgRNA 2, CAGAGATGGCGGAGTCGGAG | | N/A |
| TRAF7 sgRNA 3, CGTGGTGGTGAACAACATCG | | N/A |
| TSC1 sgRNA 1, CGAGATAGACTTCCGCCACG | | N/A |
| TSC1 sgRNA 2, ATTCGTTAATCCTGTCCAAG | | N/A |
| TSC2 sgRNA 1, AGCACGCAGTGGAAGCACTC | | N/A |
| TSC2 sgRNA 2, GTGGCCTCAACAATCGCATC | | N/A |
| Recombinant DNA | | |
| lentiCRISPR-v2 | Addgene | 83480/52961 |
| psPAX | Addgene | 12260 |
| pMD2.G | Addgene | 12259 |
| lentiCas9-Blast | Addgene | 52962 |
| GeCKO whole-genome knockout library | Addgene | 1000000049 |
| Software and Algorithms | | |
| Proteome Discoverer 2.2 | Thermo Scientific | OPTON-30795 |
| GraphPad 7.0c | Graphpad Software Inc. | N/A |
| R version 3.4.2 | (R Core Team, 2017) | https://www.R-project.org/ |
| DESeq2 version 1.16.1 | (Love et al., 2014) | https://bioconductor.org/packages/release/bioc/html/DESeq2.html |

-continued

KEY RESOURCES TABLE

| REAGENT or RESOURCE | SOURCE | IDENTIFIER |
|---|---|---|
| javaGSEA version 2.2.3 | (Subramanian et al., 2005) | http://software.broadinstitute.org/gsea/downloads.jsp |
| Rtoolbox version 1.3 | | https://github.com/PeeperLab/Rtoolbox |
| TCGAbiolinks version 2.6.12 | (Colaprico et al., 2016) | https://bioconductor.org/packages/release/bioc/html/TCGAbiolinks.html |
| Prism version 7.0c | Graphpad Software Inc. | https://www.graphpad.com/scientific-software/prism/ |
| Perseus version 1.5.6.0 | (Tyanova and Cox, 2018) | http://www.perseus-framework.org/ |
| Limma version 3.34.3 | (Ritchie et al., 2015) | https://bioconductor.org/packages/release/bioc/html/limma.html |
| Mageck version 0.5.6 | (Li et al., 2014) | https://sourceforge.net/projects/mageck/ |

Results

Cytotoxic Potential of IFNγ-Independent CD8 T Cell Signaling Modalities

Given the established antitumor activity of T cell cytokines other than IFNγ (Kearney et al., 2017; Schulze-Osthoff et al., 1998), we first experimentally queried the relative contribution of IFNγ to T cell-mediated tumor killing. We challenged a matched panel of either IFNGR1 WT or IFNGR1 KO human HLA-A*02:01+/MART1+melanoma cell lines in vitro with healthy donor CD8 T cells, which had been retrovirally transduced with a MART-1-specific T cell receptor (MART-1 T cells; Gomez-Eerland et al. 2007). Even though IFNγ signaling was disabled, these IFNGR1-KO cell lines remained remarkably susceptible to T cell killing when challenged in vitro (FIG. 1A, Figure S1A, B).

This result was corroborated in vivo, in a NOD scid gamma/B2m-deficient (NSG) mouse model, in which either parental or IFNGR1-deficient human melanoma cell lines were grafted, followed by adoptive cell transfer (ACT) with human control T cells or MART-1 T cells. In this model, albeit in a delayed fashion compared to their parental counterparts, also IFNGR1-KO tumors strongly regressed upon adoptive cell transfer (FIG. 1B). To assess the role of IFNγ also in immune-competent, tumor-bearing C57BL/6 mice, we used the murine $Braf^{V600E}$;$Pten^{-/-}$ melanoma cell line D4M.3A (Jenkins et al., 2014) expressing the model antigen ovalbumin (OVA). Compared to control tumors, Ifngr1-knockout tumors partially escaped immune control, but significantly less so than B2m-deficient tumors which, due to their lack of antigen presentation, are fully exempt from CD8 T cell attack (FIG. 1C). The results from these three independent experiments demonstrate a significant contribution of IFNγ-independent signaling to T cell antitumor activity, thereby highlighting the potential of also therapeutically exploiting IFNγ-independent T cell activity.

Genome-Wide CRISPR-Cas9 Screen for IFNγ-Independent Tumor Factors Increasing T Cell Sensitivity To genetically define the IFNγ-independent genetic tumor landscape we set out to identify therapeutic targets that upon inactivation increase tumor susceptibility to T cell elimination. Prompted by the results described above, we performed an unbiased genome-wide CRISPR-Cas9 knockout screen in IFNGR1-deficient melanoma cells to, by design, ensure that the hits would act mechanistically independently from IFNγ signaling (FIG. 1D). Cells were infected in duplicate with the GeCKO library (Shalem et al., 2014) and the two replicates were subsequently challenged with MART-1 T cells; these were derived from independent healthy individuals to circumvent donor-specific effects. Surviving melanoma cells (18% and 21% respectively) were collected, and sgRNAs were amplified from their genomic DNA by PCR and analyzed by deep sequencing (Table S1). We observed a strong correlation between replicates despite using independent T cell batches (Figure S1C). Moreover, essential genes were selectively depleted as expected (Figure S1D). Further illustrating the robustness of the screen, sgRNAs targeting the antigen presentation machinery (B2M, TAP1), or the antigen itself (MLANA), conferred resistance to T cell killing (FIG. 1E, F), which was confirmed by gene set enrichment analysis (GSEA; Figure S1E, Table S2).

More importantly, we identified several sgRNAs that, instead, strongly sensitized tumor cells to elimination by T cells (FIG. 1E, F). The two most significantly depleted genes were TNF Receptor-Associated Factor 2 (TRAF2) and BIRC2 (encoding cellular Inhibitor of apoptosis 1; cIAP1). Interestingly, the former is known to recruit the latter to inhibit death receptor-mediated apoptosis (Hsu et al., 1996; Mahoney et al., 2008; Shu et al., 1996; Wang et al., 1998; Yeh et al., 1997). While TRADD, another hit, is implicated in T-cell and TNF-induced apoptosis, its loss also sensitizes to T cell-derived TRAIL (Cao et al., 2011; Kearney et al., 2018; Kim et al., 2011). Other hits included MAP3K7, IKBKG, CFLAR and TBK1. GSEA showed that a TNF pathway, but not an IFNγ pathway, gene set was enriched amongst sensitizing hits (Figure S1E, Table S2).

Figure 1G:
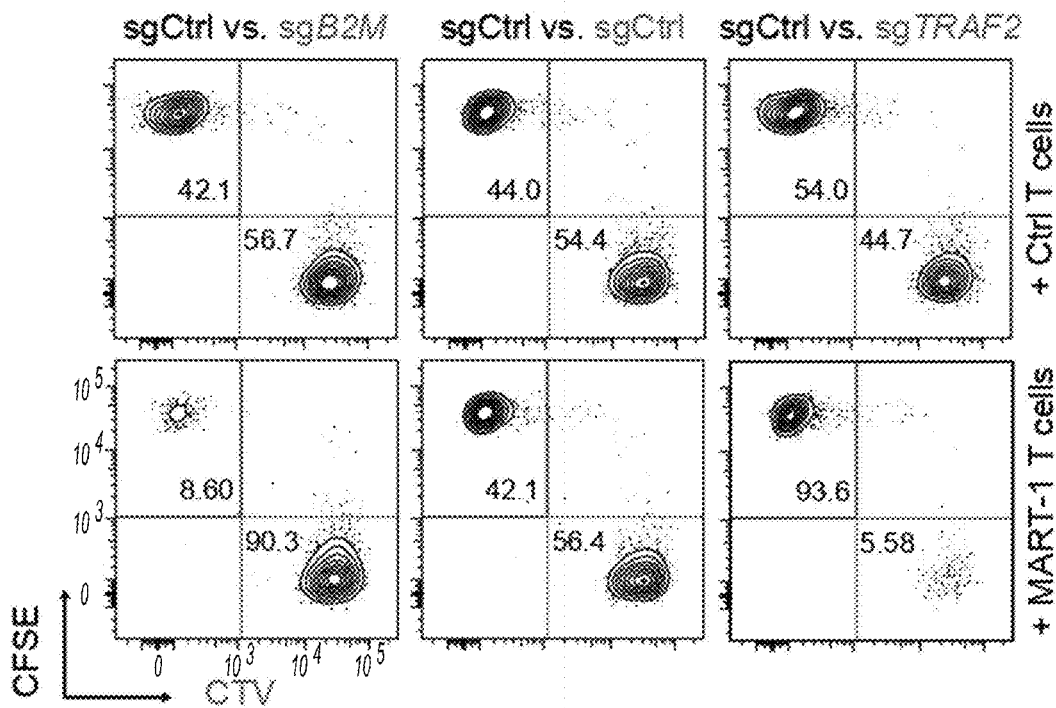

We validated these screen hits in a demultiplexed fashion. IFNGR1-KO D10 melanoma cells transduced with individual sgRNA hits (labeled with a violet fluorescent dye, CTV) were mixed 1:1 with sgCtrl-transduced ones (labeled with a green fluorescent dye, CFSE) and used in a competitive T cell cytotoxicity assay. Flow cytometric analysis revealed that for all screen hits tested, cells harboring sgRNAs targeting sensitizing genes were selectively depleted following T cell exposure, whereas cells containing a B2M sgRNA were more resistant (FIG. 1G, H). We observed similar results in non-competitive cytotoxicity assays and with independent IFNGR1-KO clones (Figure S1F-I).

We also determined whether this sensitizing effect was dependent on the lack of IFNγ signaling. For this, we focused on our top hit, TRAF2. We generated polyclonal TRAF2-deficient cell lines (Figure S1J, K) in an IFNGR1-WT background. These cells displayed a similar increase in sensitivity to T cell-mediated killing upon TRAF2 inactivation as IFNGR1-deficient cell lines, demonstrating the independency of IFNγ signaling. Additionally, this sensitization was fully rescued by TRAF2 reconstitution (Figure S1J, K), excluding off-target effects of the sgRNA used. Thus, as we had intended, this genome-wide screen yielded a series of IFNγ signaling-independent hits, several of which act in the TNF pathway. All of those were validated: their depletion strongly sensitized tumor cells to T cell killing. These results underpin the importance of TNF signaling in tumors in the response to CD8 T cells and demonstrate that this pathway can be functionally mined to yield critical factors determining the susceptibility of tumors to T cell elimination.

Figure 7E:
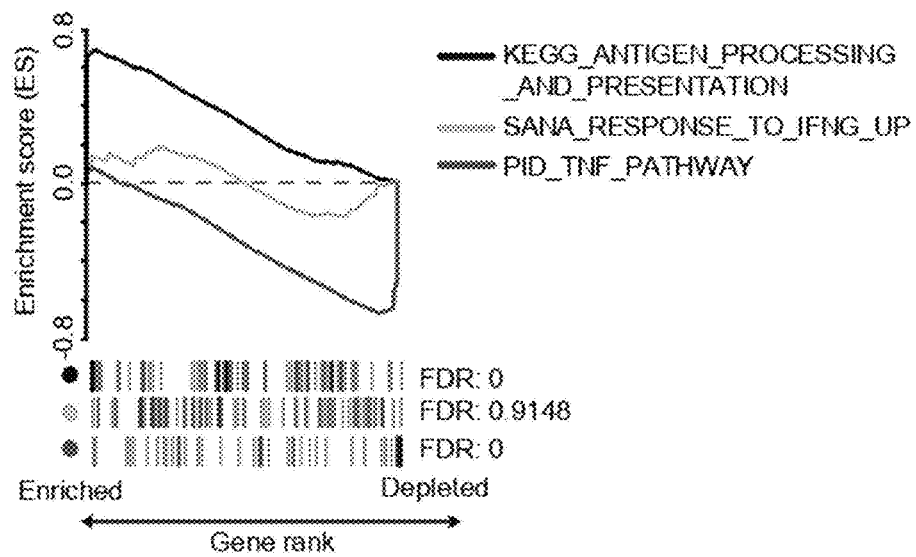
Figure 7F:
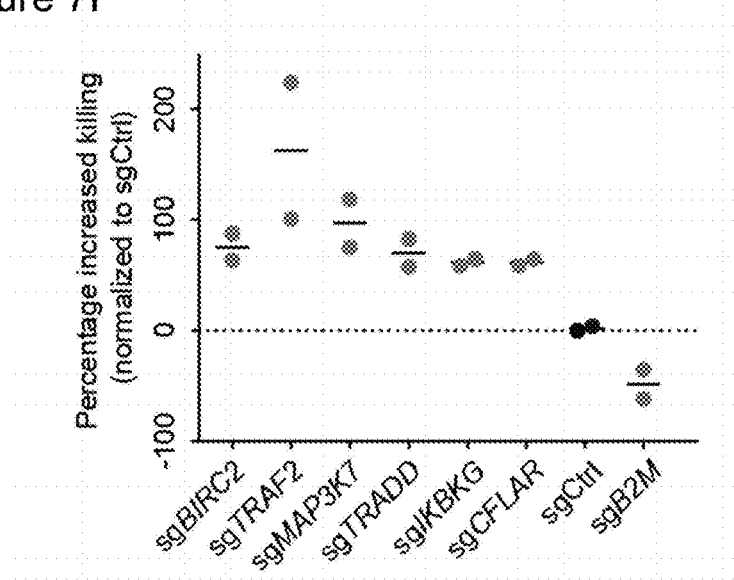

Highly Conserved Engagement of TNF Signaling Pathway Upon Tumor Engagement by T Cells Having found several factors in the TNF signaling pathway which, when ablated, significantly increase sensitivity to T cell-mediated killing, we next evaluated the role of TNF in driving an effective anti-tumor immune response, with transcriptomic analysis and in clinical samples. To define the transcriptional changes in melanoma cells upon T cell challenge, we subjected a panel of melanoma cell lines and cognate MART-1 T cells to RNA sequencing after 0, 4 and 14 hours of co-culturing. Using these data, we specifically characterized cytokine responses in the melanoma cells. By unbiased computational filtering, we revealed that out of 79 human cytokines, 43 were transcriptionally induced in T cells upon engagement with tumor cells (FIG. 7A, B, Table S3). Cognate receptors were expressed for ten of these cytokines in the melanoma cells under T cell attack, and four of those induced an actual response signature by GSEA, namely IFNγ, TGFβ, TNF and TRAIL (FIG. 7C, D, Table S2, S3, S4). We also confirmed the engagement of the TNF signaling pathway at the protein level by a proteomics-based approach (FIG. 7E, Table S5). We derived a set of differentially expressed proteins from two melanoma cell lines treated in vitro with TNF and compared these to differentially expressed proteins upon T cell attack. We found similar proteomic changes in that setting (FIG. 7E). The engagement of these cytokine signaling pathways was further recapitulated in tumors of melanoma patients, showing concordance between the presence of activated CD8 T cells and these cytokine-related gene signatures, including TNF (FIG. 7F). These results indicate that the engagement of TNF signaling pathway upon tumor:T cell encounter is a conserved trait that is also observed in patient tumors.

Important Role for TNF in ICB-Responding Tumors but not in Untreated Tumors

Figure 2A:
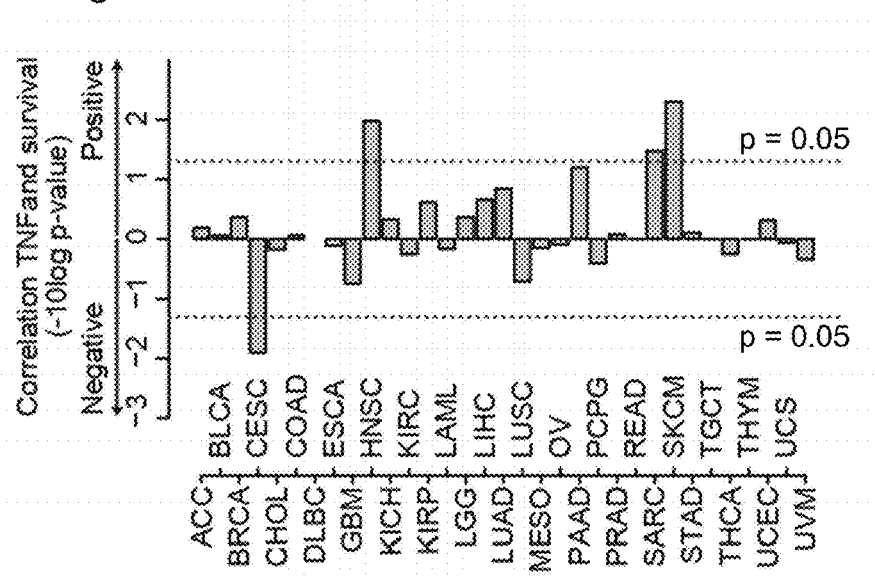
Figure 2B:
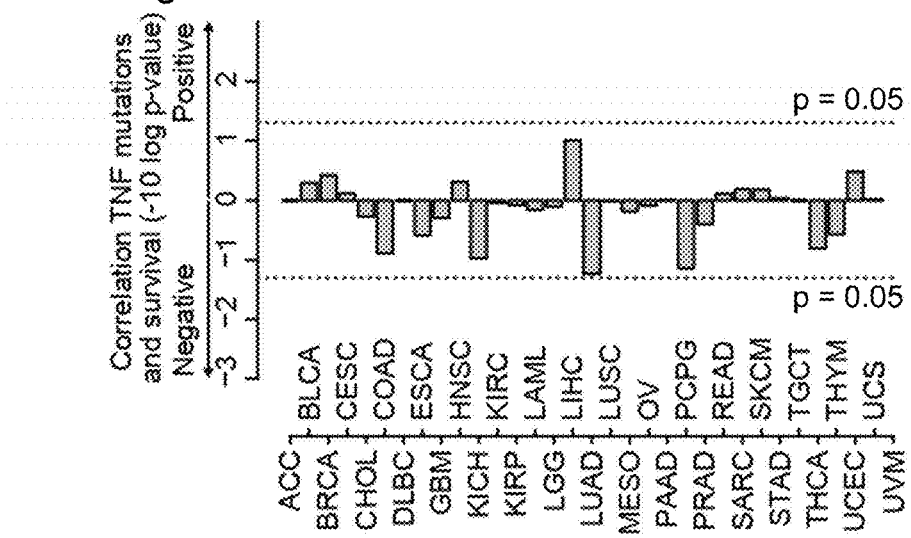
Figure 2C:
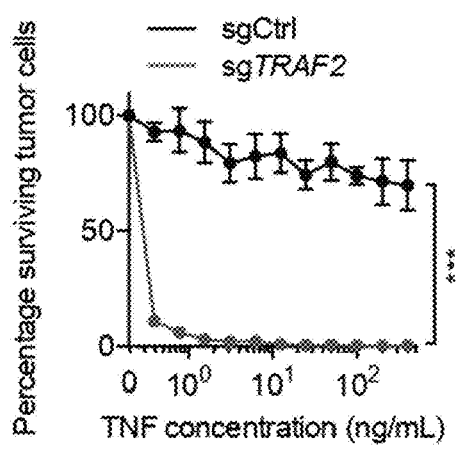

Having demonstrated that CD8 T cells are in principle capable of producing TNF in the tumor microenvironment, we next wished to obtain clinical substantiation of these results and investigated a role for T cell-derived TNF in functionally affecting patient tumors. In an analysis of the TCGA (comprising pre-treatment tumors), we did not detect a correlation between TNF expression and patient survival (FIG. 2A). As a complementary approach, we assessed whether the TNF signaling pathway in tumors is subject to selective mutational pressure by the immune system, similar to what has been described for IFNγ signaling (Gao et al., 2016; Sharma et al., 2017; Shin et al., 2017; Zaretsky et al., 2016). Again, by analyzing TCGA data, we could not find a correlation between non-synonymous TNF pathway mutations and survival in any cancer subtype (FIG. 2B). Together, these data suggest that under baseline conditions, TNF is unlikely to act as a potent tumor cytotoxic factor and that it is necessary but not sufficient for anti-tumor effects. We corroborated this notion in vitro, since, in a dose-titration experiment with TNF, even high concentrations of TNF were unable to cause control tumor cells to die (FIG. 2C; and see below).

Figure 2D:
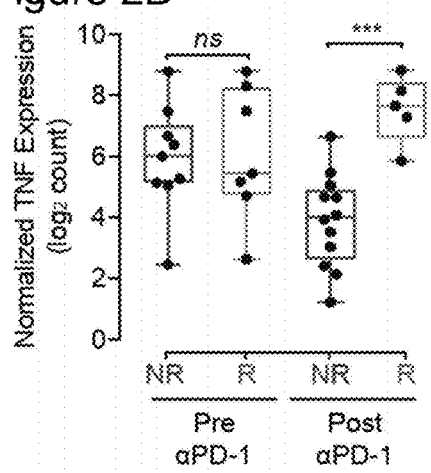
Figure 2E:
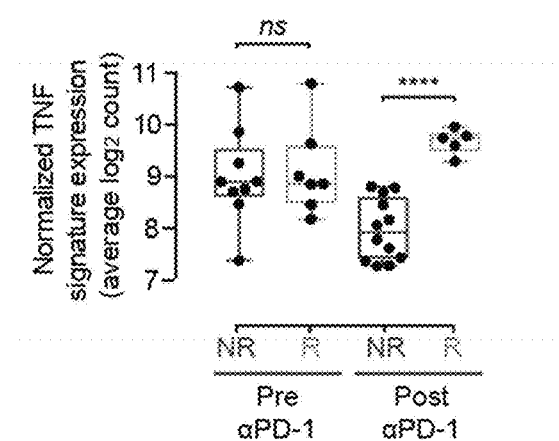
Figure 2F:
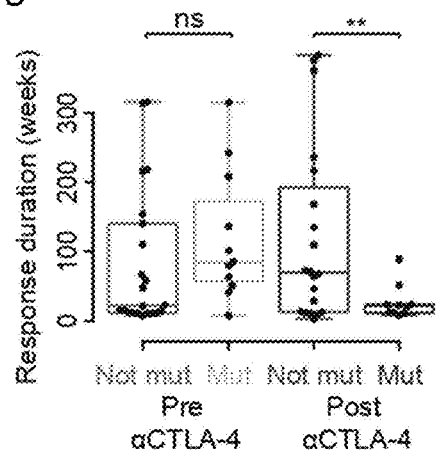
Figure 2G:
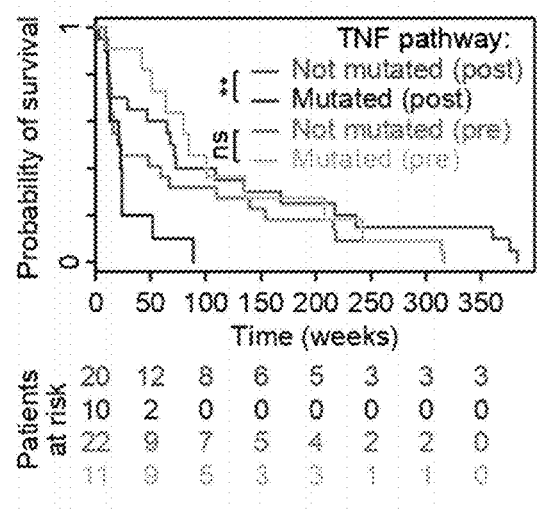
Figure 7G:
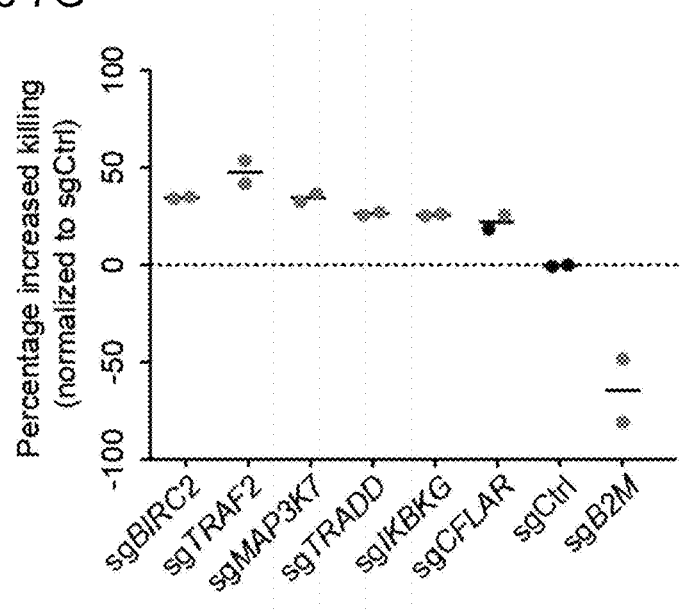
Figure 7H:
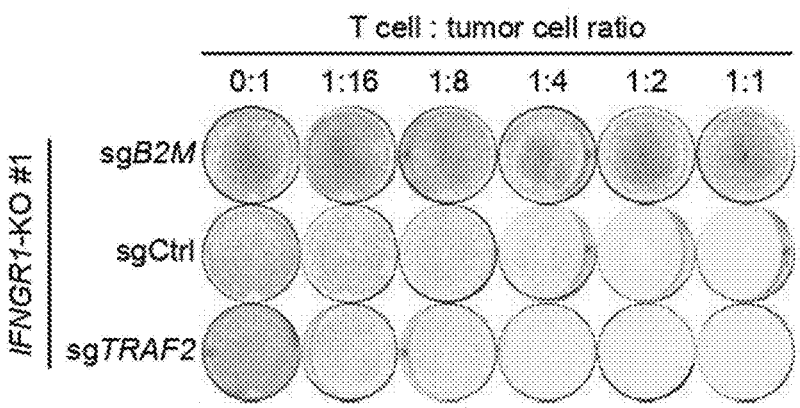
Figure 7I:
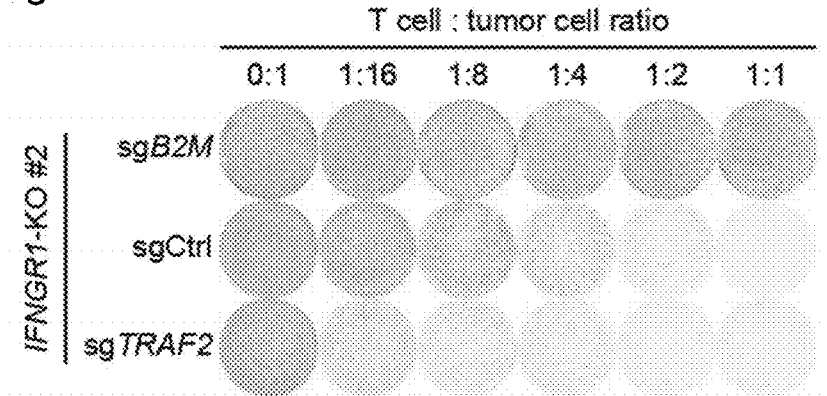
Figure 7J:
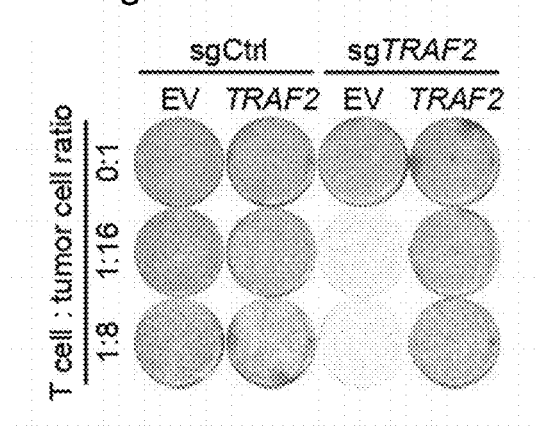

ICB can increase cytokine production in ex vivo settings (Jacquelot et al., 2017). Therefore, we next analyzed tumor gene expression data of two cohorts of patients treated with anti-PD-1 therapy (Riaz et al., 2017; Roh et al., 2017). We hypothesized that any clinical role of TNF in T cell antitumor activity may be unleashed by ICB, particularly in responding patients. Supporting this idea, in both cohorts we detected higher expression of TNF in responding patients (R) than in non-responding ones (NR), but only after therapy onset (FIG. 2D, FIG. 7G). The higher expression levels of TNF were corroborated by a similar increase of a TNF response signature in both datasets (FIG. 2E, FIG. 7H). Such correlations were, to a lesser extent, also observed for an IFNγ signature (Ayers et al., 2017; FIG. 7I, J).

Figure 7K:
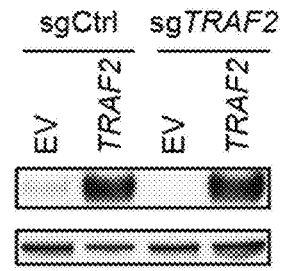
Figure 8A:
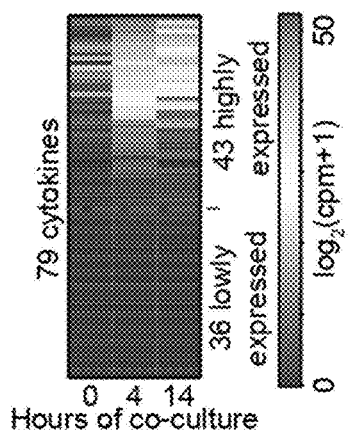
Figure 8B:
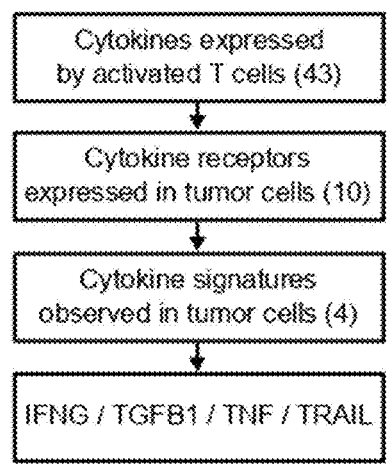
Figure 8C:
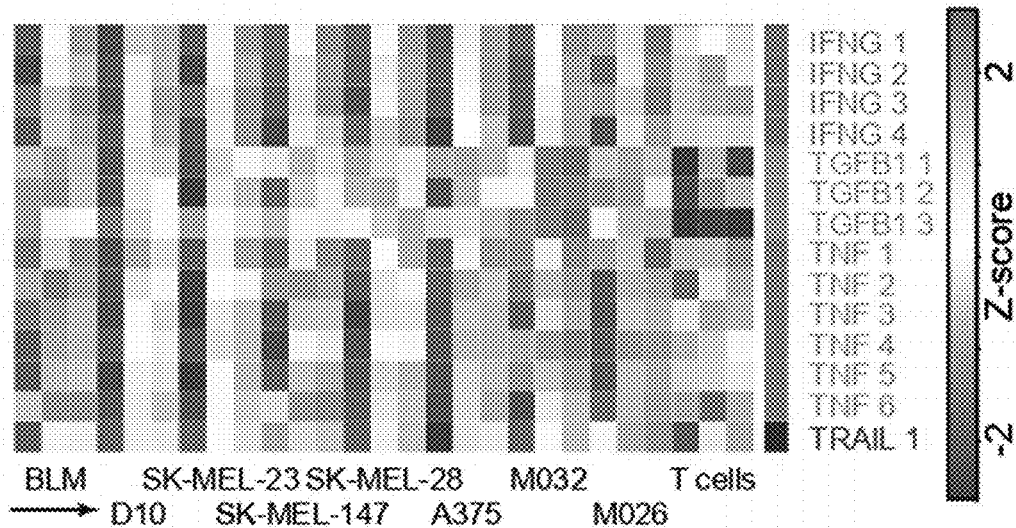
Figure 8D:
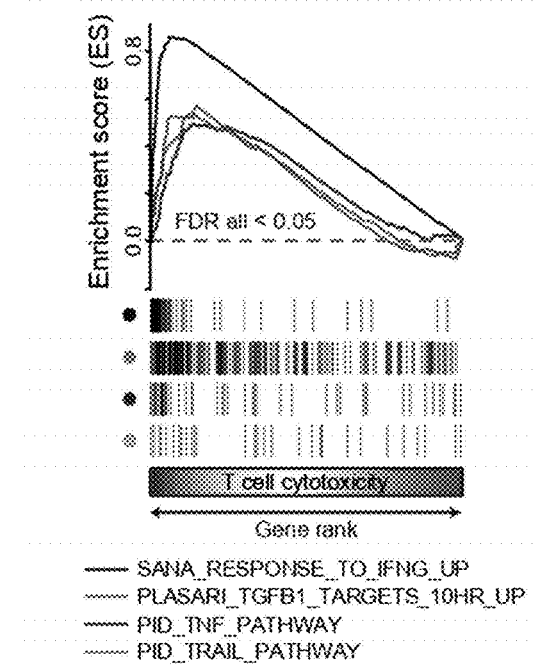
Figure 8E:
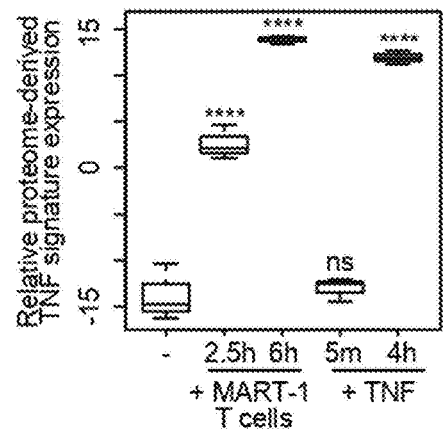
Figure 8F:
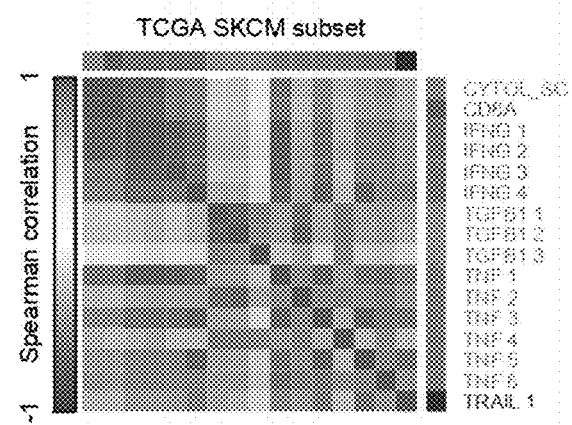
Figure 8G:
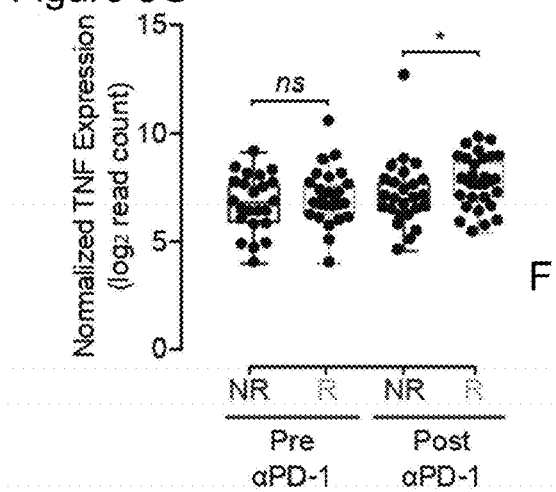
Figure 8H:
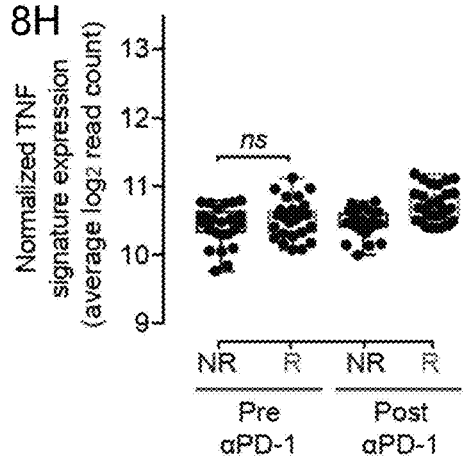
Figure 8I:
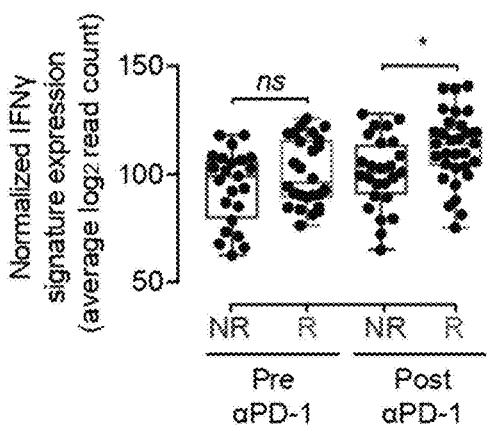
Figure 8J:
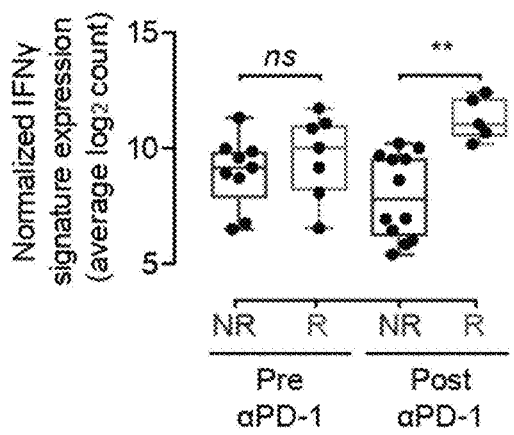
Figure 8K:
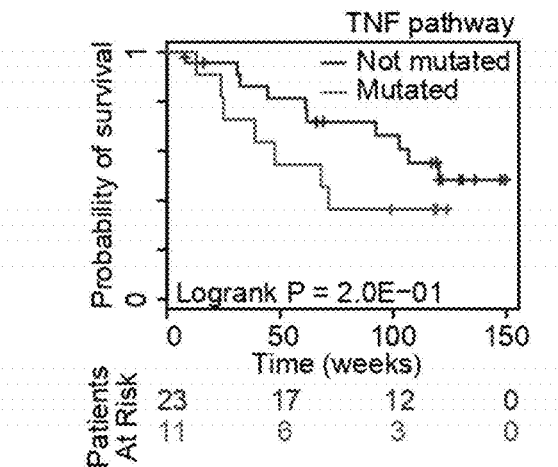
Figure 8L:
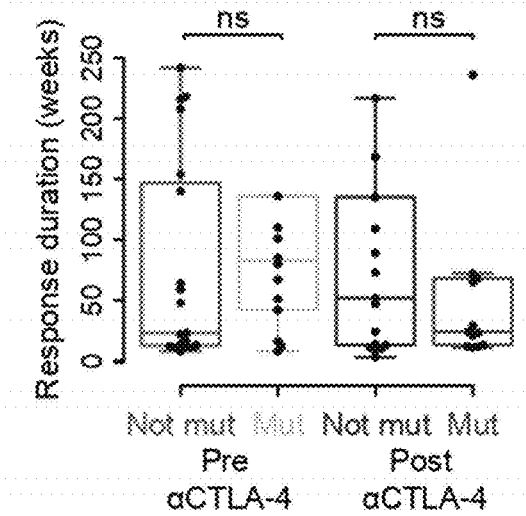
Figure 8M:
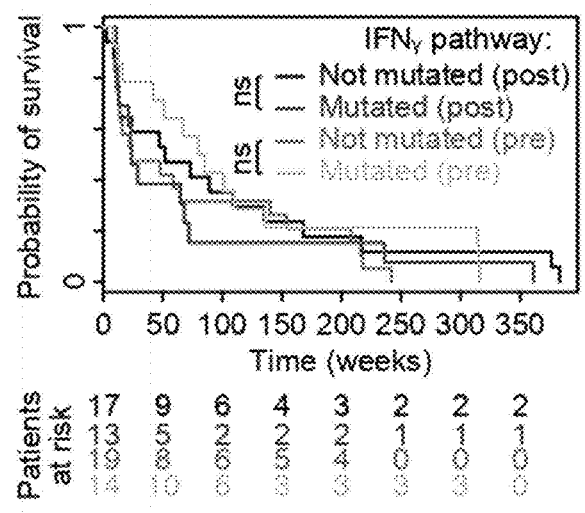

This result motivated us to next assess whether we could find evidence for the hypothesis that the rise in TNF levels upon ICB response is likely to drive tumor cytotoxicity. Therefore, we performed a complementary analysis in which we again assessed selective mutational pressure by TNF on the TNF signaling pathway as a whole, but this time comparing tumor mutations before and after onset of therapy. Although patient cohorts with mutation data before and after onset of therapy are rare, we could study a melanoma patient cohort treated with anti-CTLA-4 therapy (Snyder et al., 2014). This analysis revealed that both response duration and overall survival were profoundly lower for treated patients with tumors harboring non-synonymous TNF pathway mutations than wildtype TNF pathway tumors (FIG. 2F, G; Table S6). This included several dozen mutations in established and essential signaling proteins in the TNF pathway, such as RIPK1, NFKB1, CYLD and MADD protein, a key transducer of TNF-mediated prosurvival signals (Kurada et al., 2009; Schievella et al., 1997). Future functional studies will be required to determine the individual impact of all these mutations on TNF pathway signaling output. In a second patient cohort, with limited follow-up of patient survival, we detected a similar trend (FIG. 7K). These correlations could not be found for IFNγ pathway-mutant tumors (FIG. 7L, M). Collectively, these data imply that in ICB-responding tumors, but not under baseline conditions, TNF plays a crucial role: because its expression rises with ICB response, this sets the stage for immune editing of the TNF pathway, causing reduced ICB responsiveness.

TRAF2 Inactivation Reduces TNF Cytotoxicity Threshold

These clinical data suggest an important role of TNF in driving an antitumor response in the context of ICB. Another implication of these results is that in untreated tumors, and those unresponsive to ICB, there is a low abundance of TNF, which is insufficient to exert meaningful antitumor activity. Therefore, we argued that for tumors at baseline to become susceptible to T cell elimination, the threshold to respond to TNF would need to be lowered. Taking advantage of the CRISPR/Cas9 screen results, we hypothesized that this can be achieved by inactivating the tumor-intrinsic TNF pathway. Specifically, we assessed whether inactivation of TRAF2, the top hit from the screen, could sensitize tumors to low concentrations of TNF. In contrast to wildtype cells, which hardly displayed any sensitivity to TNF, TRAF2 inactivation dramatically reduced the TNF cytotoxicity threshold, to the extent that tumor cells died at picogram TNF concentrations (FIG. 2C). Such concentrations are physiologically relevant, since they were found in both tumor samples and patient serum analyses (Sasi et al., 2012; Yurkovetsky et al., 2007). These results are in line with the clinical data described above and suggest that lowering the TNF cytotoxicity threshold, for example by TRAF2 inhibition, may benefit both untreated patients and patients who are unresponsive to ICB.

Figure 3A:
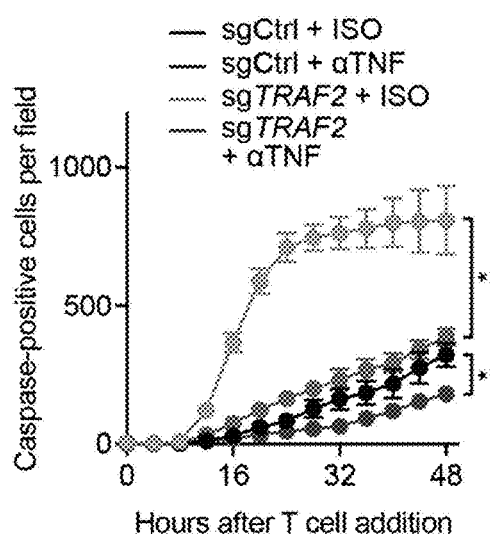
Figure 3B:
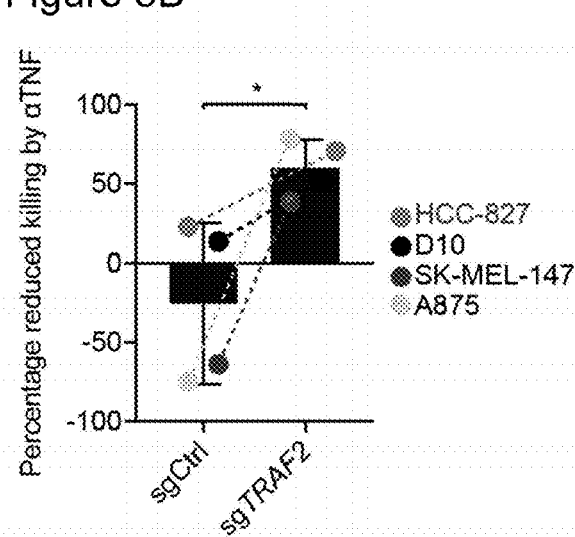
Figure 3C:
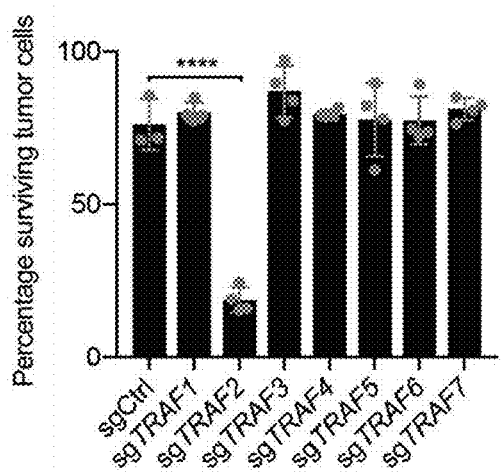

TRAF2 Inactivation Poises Tumors to Undergo RIPK1-Dependent Cell Death in Response to T Cell-Derived TNF Since TRAF2 inactivation appeared a powerful means of sensitizing tumor cells to clinically relevant TNF concentrations, we investigated the mechanistic interplay between T cells, TNF and TRAF2 in more detail. First, in a T cell cytotoxicity assay, a neutralizing antibody to TNF strongly reduced T cell-induced apoptosis in TRAF2-deficient cells, back to the levels seen in VVT melanoma cells (FIG. 3A), demonstrating that TNF is the predominant T cell cytokine accounting for the TRAF2-dependent increase in susceptibility to T cell elimination. Extending this to a panel of melanoma and lung adenocarcinoma cell lines, we observed that T cell-derived TNF showed tumor cytotoxicity only after TRAF2 inactivation (FIG. 3B). Among the seven TRAF family members, TRAF2 was the single one to predispose to T cell killing, suggesting a unique role for this factor (FIG. 3C).

Figure 3D:
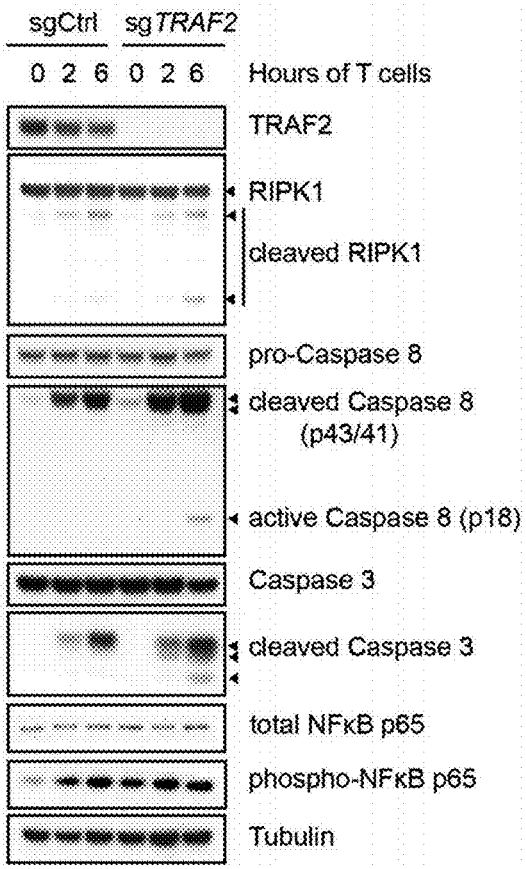
Figure 3E:
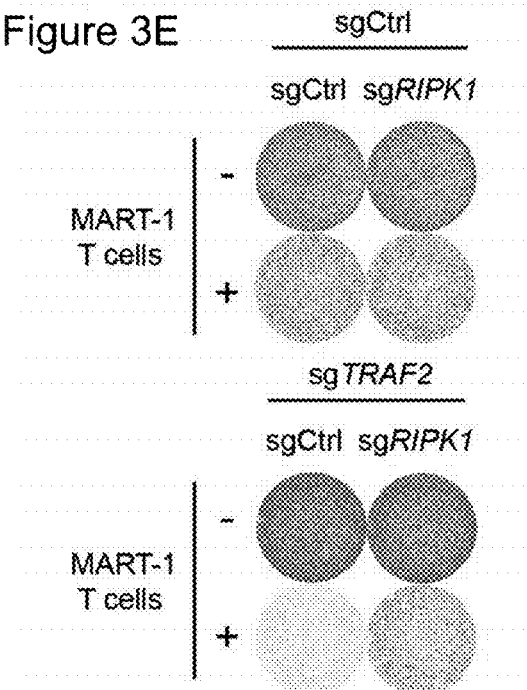
Figure 3F:
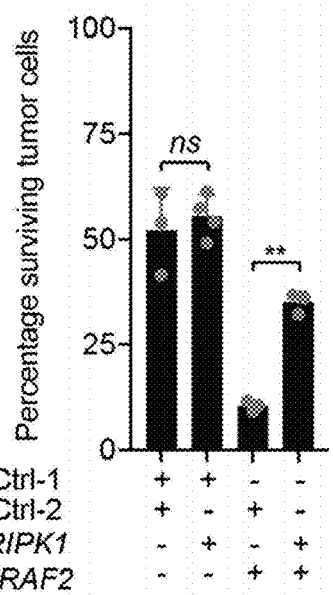

Next, we aimed to dissect how, mechanistically, inactivation of TRAF2 sensitized tumor cells to T cell-derived TNF. Western blot analysis indicated that while baseline phosphorylation of NF-κB p65 was higher in TRAF2-deficient melanoma cells, after challenge by T cells there was no apparent difference between the two genotypes, consistent with earlier observations (Yeh et al., 1997). More strikingly, in TRAF2-deficient melanomas, T cells induced cleavage of Receptor Interacting Protein Kinase 1 (RIPK1) and terminal caspase 8 activation more rapidly and strongly (FIG. 3D). This sequence of events is known to lead to RIPK1-dependent cell death (Lin et al., 1999). The engagement of this mode of cell death was confirmed by the genetic inactivation of RIPK1, which largely prevented increased sensitivity to T cells in TRAF2-deficient melanomas (FIG. 3E, F). This genetic, epistatic rescue of sensitivity was not observed in TRAF2-proficient cells, implying that TRAF2 acts as a critical gatekeeper for the instigation of RIPK1-dependent cell death. We conclude from these results together that inactivation of TRAF2 redirects the TNF signaling pathway to favor RIPK1-dependent cell death, thereby allowing T cells to kill tumor cells more efficiently.

Clustering of Agonistic TWEAK Receptor Antibody Sensitizes Tumors to TNF-Dependent Cell Death by Downregulating TRAF2

Figure 3G:
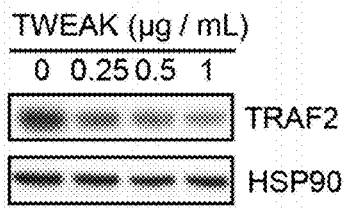
Figure 3H:
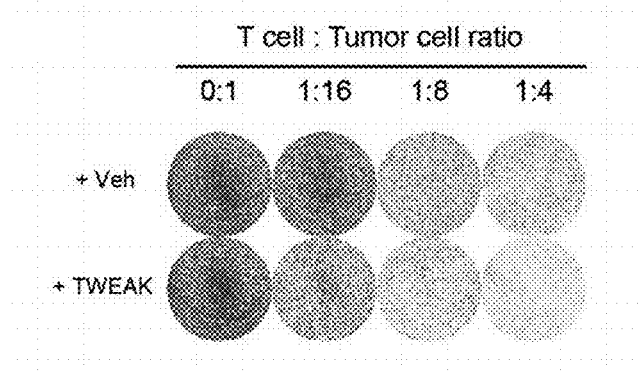
Figure 9A:
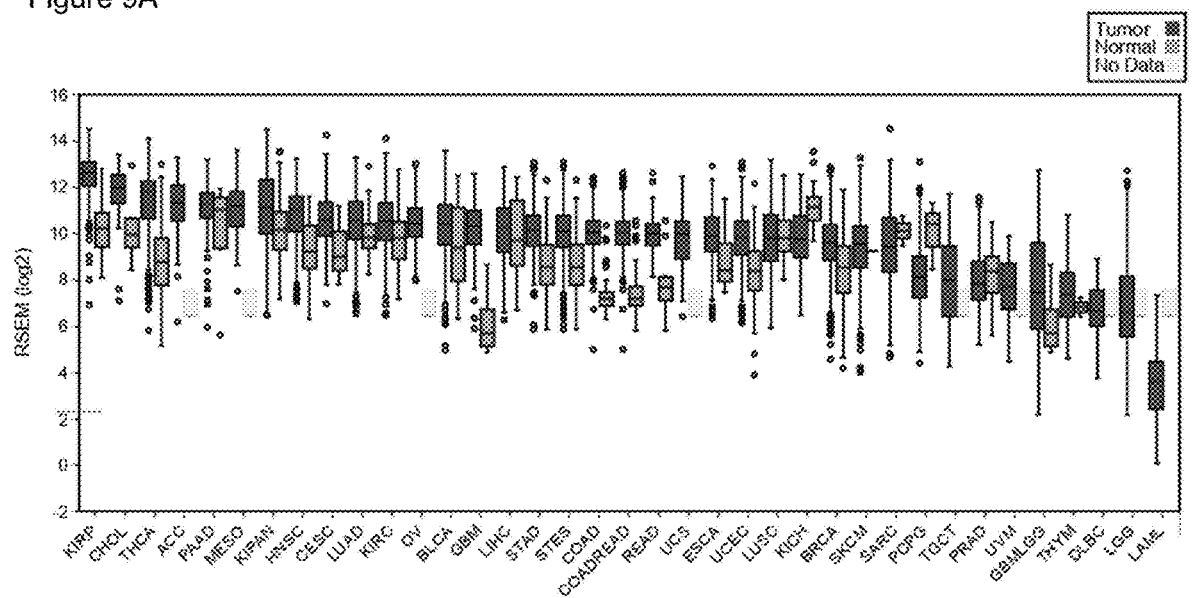
Figure 9B:
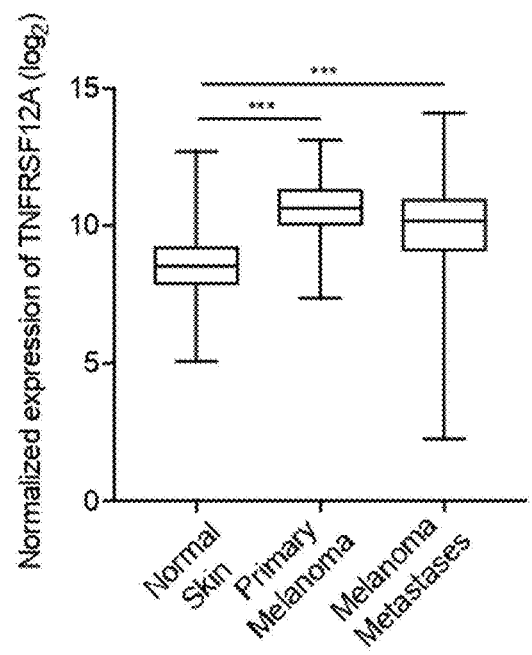

We next set out to begin translating these findings to a more clinical setting. Whereas no small molecule inhibitor of TRAF2 is available, it has been reported that stimulation of Fn14 (encoded by TNFRSF12A) by its ligand TWEAK can lead to the lysosomal degradation of TRAF2 (Vince et al., 2008). To determine the utility of an Fn14-based strategy to degrade TRAF2, we first assessed the expression of TNFRSF12A in tumors and healthy tissue. We found that the expression Fn14 is generally higher in tumors than in corresponding healthy tissues (FIG. 9A) and, in melanoma, this same holds true for metastatic lesions (FIG. 9B). Given this observation, Fn14 may represent an attractive translational target. We next confirmed that the treatment of melanoma cells with TWEAK led to the degradation of TRAF2 (FIG. 3G). More importantly, the addition of TWEAK sensitized tumor cells to T cell killing (FIG. 3H).

Figure 3I:
Figure 3J:
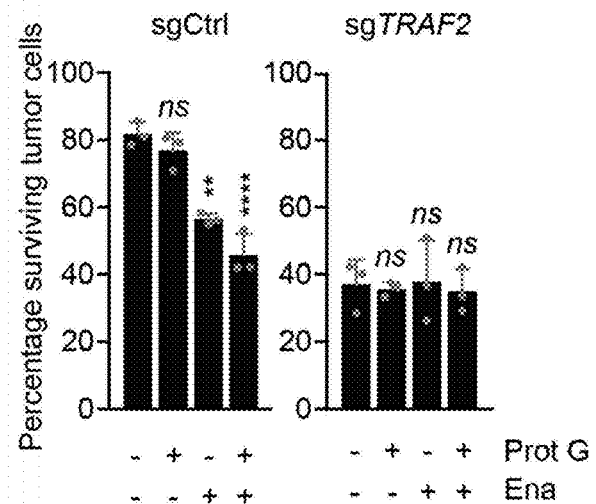
Figure 9C:
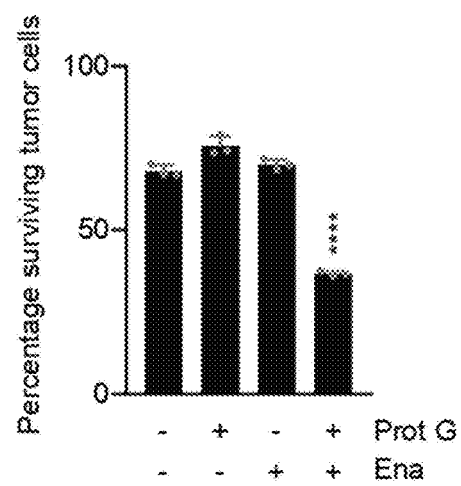

We next asked whether the same could be accomplished by means of an antibody-based targeting approach, for which we used the agonistic anti-Fn14 antibody enavatuzumab (Lam et al., 2018; Salzmann et al., 2013). Treatment with enavatuzumab caused degradation of TRAF2, but only upon receptor clustering by the addition of protein G (FIG. 3I). More importantly, we continued by assessing the effect of enavatuzumab on the sensitivity of tumor cells to T cells. We observed that the clustered agonism of Fn14 induced sensitivity to T cell cytotoxicity in two melanoma cell lines (FIG. 3J, FIG. 9C).

Figure 9D:
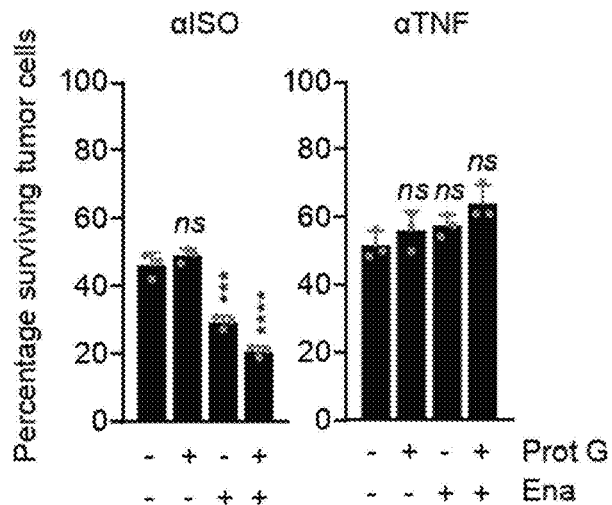

We also determined whether this sensitization was dependent on TRAF2. We exposed either wildtype or TRAF2-deficient tumor cells to T cells in the presence or absence of enavatuzumab. We found that not only the sensitization by enavatuzumab was dependent on TRAF2, but also that the degree of sensitization to T cell killing was similar between tumor cells treated with enavatuzumab and untreated TRAF2-deficient tumor cells (FIG. 3J). Using neutralization with an anti-TNF antibody we were also able to show that enavatuzumab-mediated sensitization was dependent on T cell-derived TNF (FIG. 9D). Thus, clustering of an agonistic Fn14 antibody may be a tangible means to translate our findings to a future clinical setting.

Figure 4A:
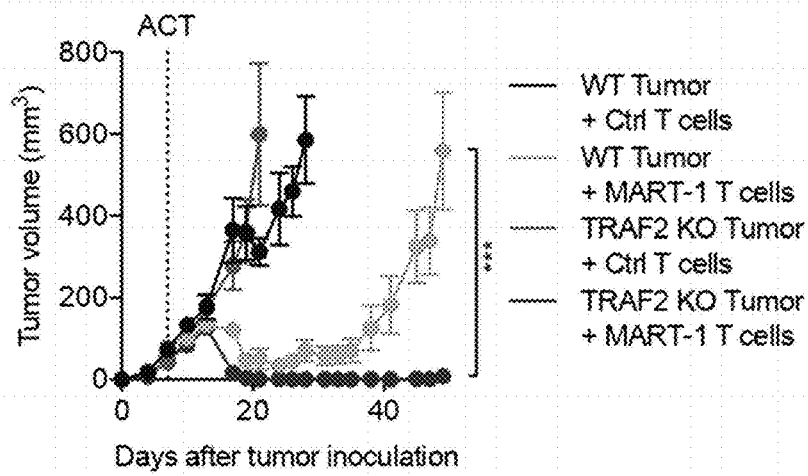
Figure 4B:
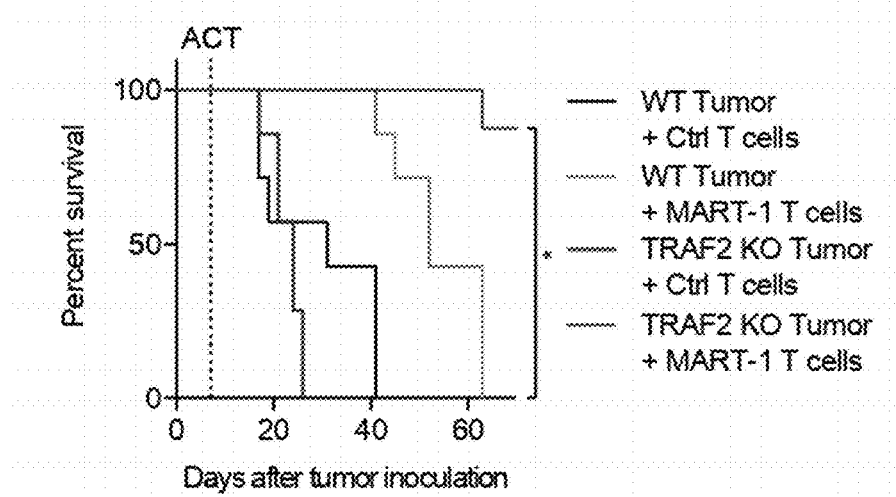
Figure 4C:
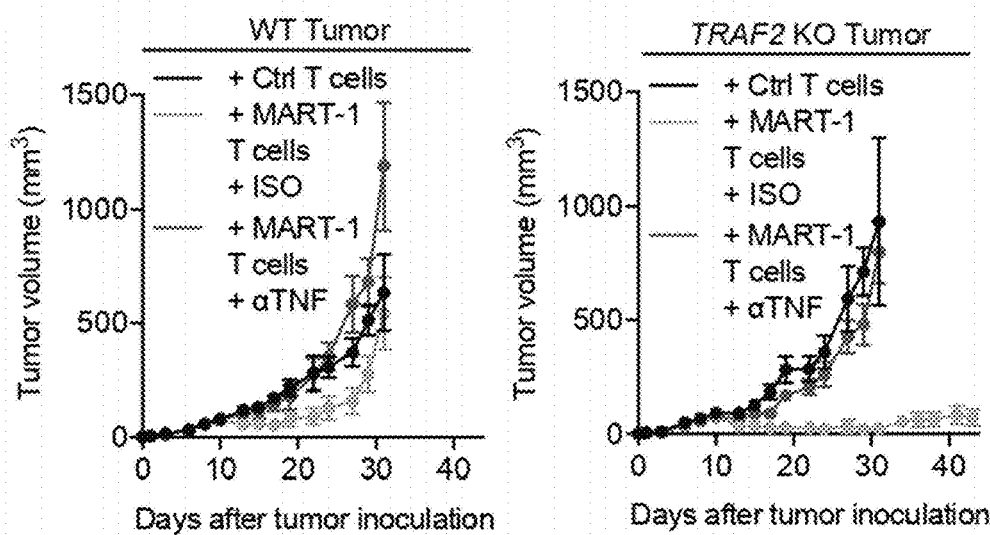
Figure 4D:
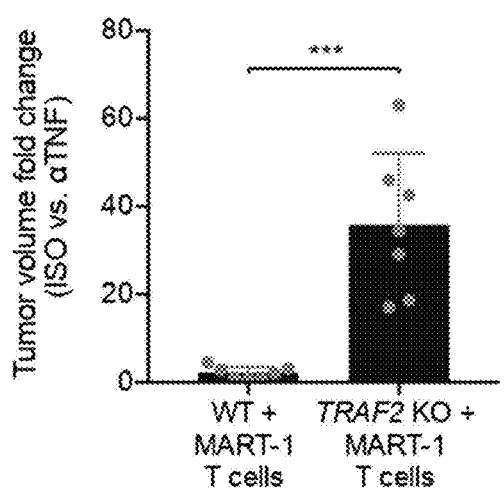
Figure 4E:
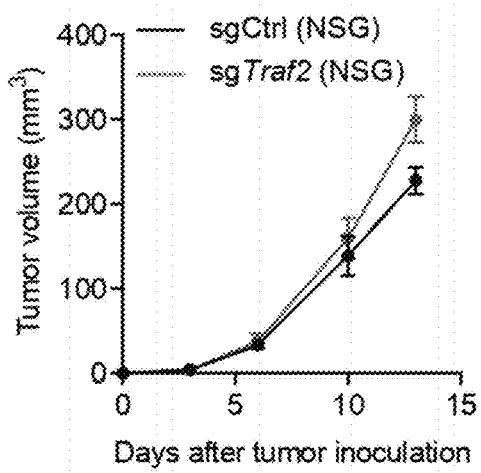

TRAF2 Loss Sensitizes to CD8 T Cell-Derived TNF in Immune-Proficient and ACT Animal Models We next determined whether TRAF2 deficiency provokes tumor sensitization to T cell cytotoxicity also in vivo, in two independent models. In an NSG mouse model, in which either VVT or TRAF2-deficient clonal human melanoma cell lines were grafted, there was no apparent defect in tumor growth in the absence of T cell pressure (ACT with control T cells; FIG. 4A, B). In contrast, inactivation of TRAF2 allowed for superior tumor control compared to VVT tumors in those mice injected with MART-1 T cells, demonstrating the need for immune pressure for the rejection of TRAF2-deficient tumors (ACT with MART-1; FIG. 4A, B). Injection of the anti-TNF antibody infliximab revealed that this tumor control was dependent on TNF, consistent with our in vitro findings (FIG. 4C, D). Also, in keeping with our clinical data, TNF had a relatively minor contribution to T cell-mediated killing of control (TRAF2-proficient) tumors (FIG. 4D).

Figure 4F:
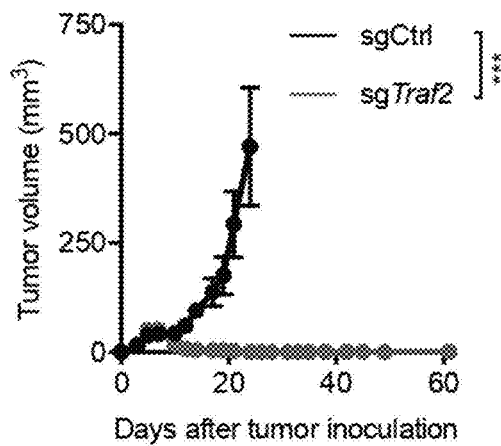
Figure 4G:
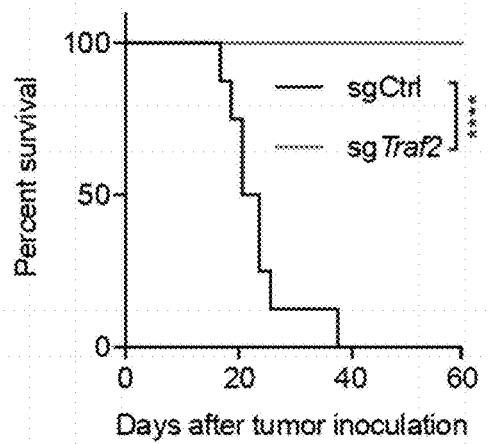

We expanded these in vivo studies by assessing the role of murine Traf2 in an immune-competent model. For this, we injected either parental or Traf2-deficient D4M.3A-OVA murine melanoma cell lines in C57BL/6 or NSG mice. Although all tumors initially established, and grew similarly in NSG mice (FIG. 4E), Traf2-deficient tumors were all rapidly and efficiently cleared in C57BL/6 mice, again highlighting the need for immune pressure for the clearance of Traf2-deficient tumors (FIG. 4F). This resulted in 100% survival rates for as long as 60 days after tumor inoculation, at which time all control tumor-bearing mice had been sacrificed (FIG. 4G). Collectively, these results show that TRAF2 loss strongly sensitizes to CD8 T cell-derived TNF, which allows for tumor eradication in both immunocompromised ACT and immunocompetent mouse models.

TRAF2 Mutations in Patients' Tumors Conferring T Cell Resistance

Figure 10A:
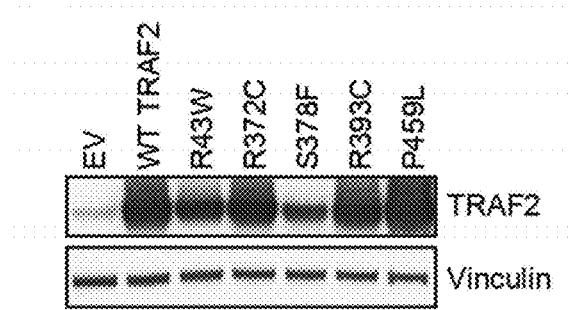

Our mechanistic data above demonstrate that TRAF2 is a critical gatekeeper for (RIPK1-dependent) tumor cell death in response to T cell-derived TNF. Furthermore, our clinical data indicate that TNF expression rises with ICB response and that failure to respond to ICB correlates with mutations in the TNF pathway. Therefore, we investigated whether specifically the TNF pathway factor TRAF2 plays an important role in determining sensitivity to T cells in patient tumors. When analyzing TCGA transcriptomic data, we observed that increased expression of TRAF2 is frequent in cancer, relative to normal tissue (FIG. 5A). To determine whether such high expression levels of TRAF2 alter the susceptibility to T cell killing, we subjected cells that ectopically express TRAF2 to a competitive T cell cytotoxicity assay. Compared to cells with an empty vector control, cells that overexpressed TRAF2 were more resistant to T cell killing (FIG. 5B, FIG. 10A).

By mining TCGA sequencing data, we also found that TRAF2 is recurrently mutated at a number of residues (FIG. 5C). To determine whether these mutations affect T cell sensitivity, we generated tumor cell lines carrying these clinical TRAF2 mutant alleles and subjected them to a T cell cytotoxicity assay (FIG. 10A). Expression of the R43W and the S378F mutants rendered melanomas more resistant to T cell killing, as judged by both a tumor:T cell competition assay and caspase 8 signaling (FIG. 5D, 9C). This observation, together with the overexpression data, suggest that patient tumors can evolve to avoid immune clearance by modulating both TRAF2 expression and function.

Figure 10B:
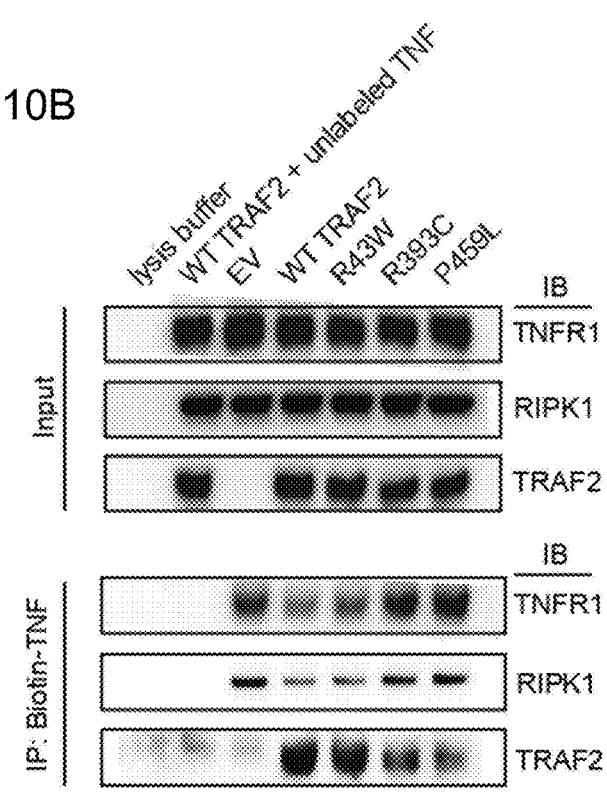
Figure 10C:
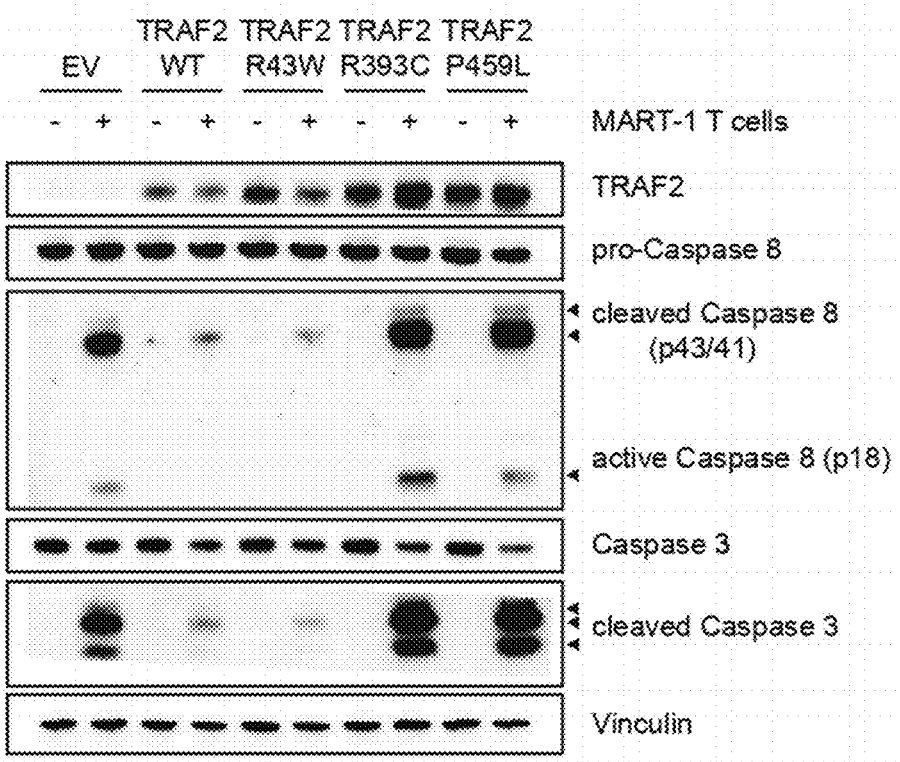
Figure 10D:
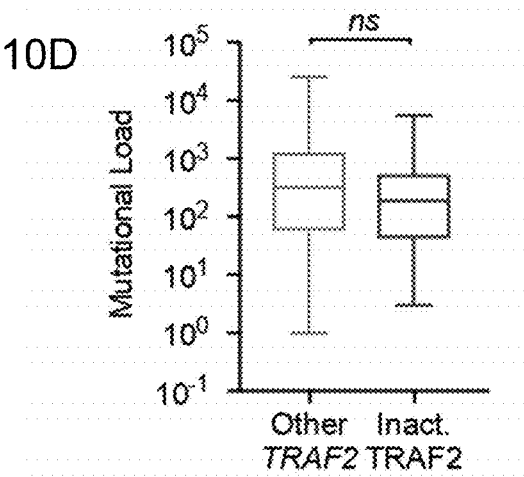

Two other TRAF2 mutants, R393C and P459L, instead sensitized tumor cells to T cell killing (FIG. 5D). Since these mutations lie within the TRAF2 receptor-binding motif (Wu, 2004), we hypothesized that they may reduce TRAF2 incorporation into active TNF receptor (TNFR) complexes, thereby hindering TRAF2 from performing its anti-apoptotic function. Indeed, TRAF2 R393C and P459L were less abundant in active TNFR complexes, resulting in elevated apoptotic signaling after T cell attack of the corresponding cell lines (FIG. 10B, C). As our results predict it unlikely that tumors could evolve while harboring such immune-sensitizing mutations in isolation, we investigated the possible co-occurrence of compensatory genetic events. We found that the mutation rate for both HLA I alleles or B2M was significantly higher in tumors carrying inactivating (R393, P49L or frameshift) TRAF2 mutations than those with other TRAF2 mutations (FIG. 5E). This was seen independently of general mutational load (FIG. 10D). These observations suggest that tumors carrying T cell-sensitizing TRAF2 mutations are under immune-editing pressure to avoid T cell attack by, for example, loss of antigen presentation. Furthermore, this information may be helpful in the future design of a small molecule therapeutic for TRAF2. These clinical mutational data collectively imply that TRAF2 is a pivotal signaling node governing the response to T cell attack in patients' tumors. Our in vivo and clinical data indicate that the immune system exerts a selective pressure on the antigen presentation machinery of tumors to compensate for loss of functional TRAF2.

Figure 1H:
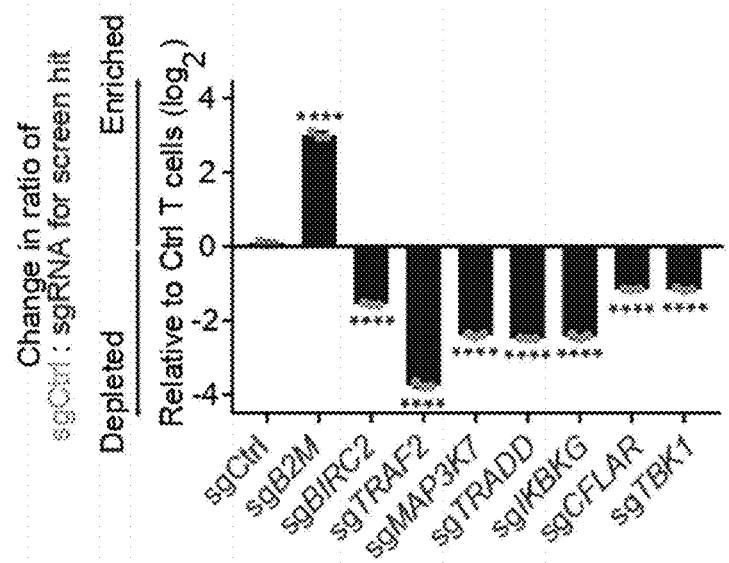
Figure 6A:
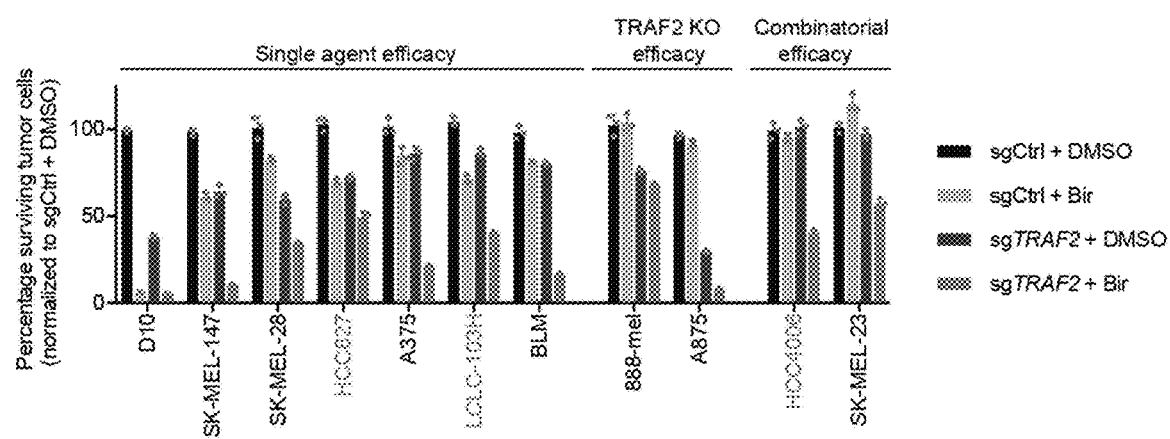
Figure 11A:
Figure 11B:
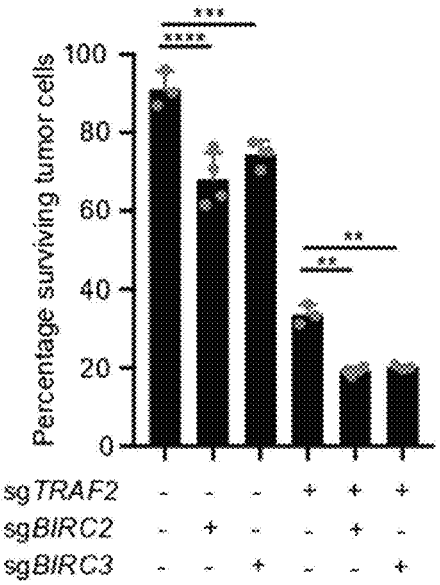

Combined Genetic and Pharmacologic Inhibition of TRAF2/cIAP Complex Sensitizes Panel of Melanoma and Lung Cancer Cell Lines to T Cell Killing To study the applicability of TRAF2 inactivation in a broader context, we inactivated this gene in a panel of 11 human melanoma and lung cancer cell lines and assessed their response to T cell exposure (FIG. 6A). Cas9 targeting efficiency was high in all cell lines (FIG. 11A). For nine of those, TRAF2-deficiency increased sensitivity to T cell killing (FIG. 6A, labeled as "Single agent efficacy" and "TRAF2 KO efficacy"). Two tumor cell lines experienced little to no T cell sensitization, independent of their genetic makeup. We then reasoned that co-targeting another TNF pathway component may break this intrinsic T cell resistance and, reminiscent of the cooperative impact of co-inhibiting mutant BRAF and MEK in melanoma (Long et al., 2014), may result in synergistic killing. In our CRISPR screen, we observed that aside from TRAF2, also loss of BIRC2 (the second top hit, encoding cIAP1) sensitized tumor cells to T cell killing (FIG. 1H). We therefore targeted BIRC2 (or its paralog BIRC3) in either wildtype or TRAF2-deficient melanoma cells. In both contexts, the targeting of either BIRC family member resulted in increased sensitivity to T cells (FIG. 11B).

Figure 6B:
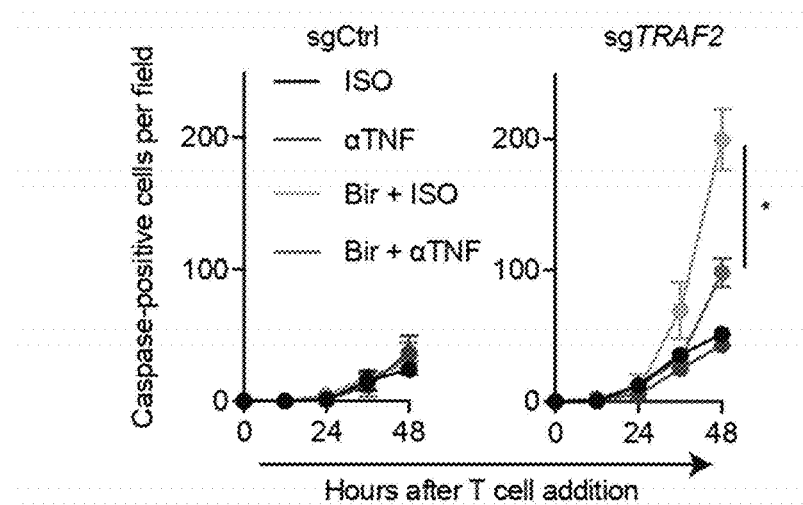
Figure 6C:
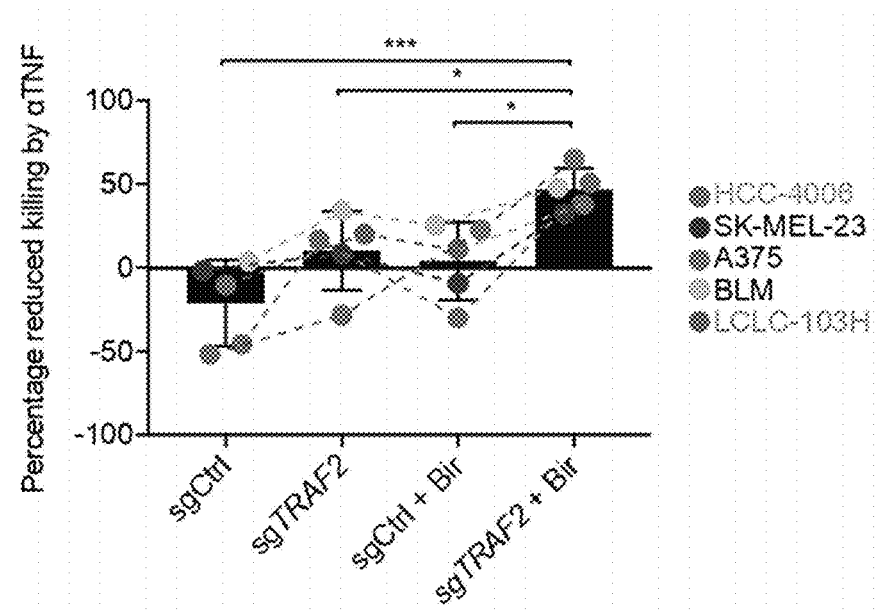
Figure 11C:
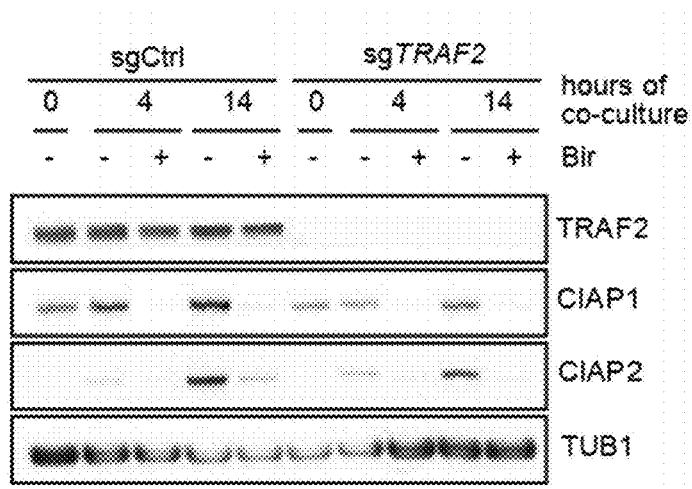
Figure 11D:
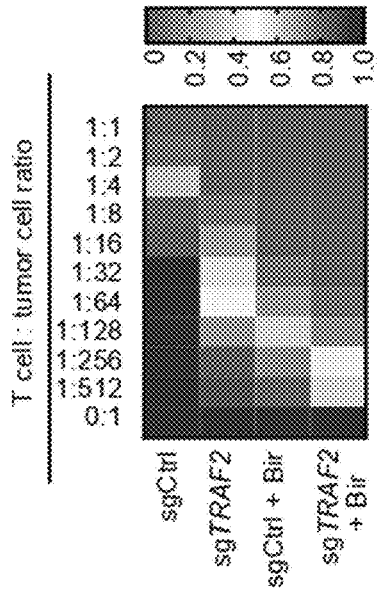
Figure 11E:
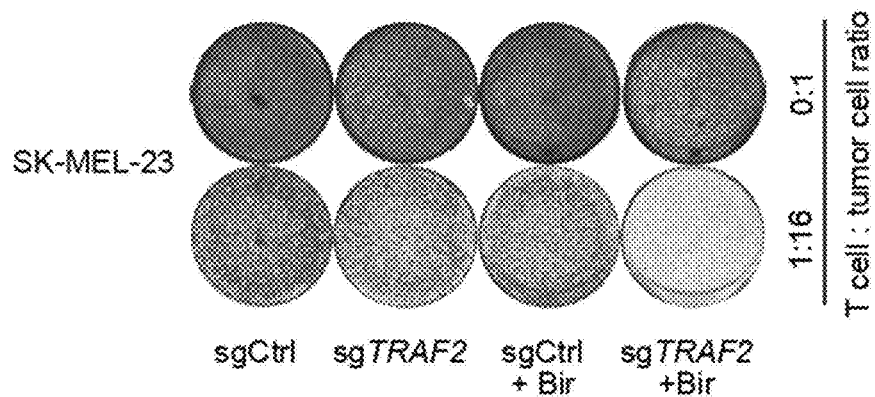

Genetic loss of BIRC2/3 can be mimicked by the pharmacological drug birinapant, which is a bivalent SMAC mimetic known to degrade both BIRC2/3 protein products (Benetatos et al., 2014; cIAP1/2 respectively; FIG. 11C). Birinapant synergized with TRAF2 inactivation in inducing sensitivity to T cell killing (FIG. 11D). We next tested whether co-treatment with birinapant could break T cell resistance of the tumor cell lines failing to undergo sensitization upon TRAF2 depletion. Indeed, we observed a strong synergy between TRAF2 deletion and pharmaceutical targeting of cIAP1/2 in all tested tumor cell lines, with some (e.g., SK-MEL-23) displaying increased sensitivity to T cells only in the combination setting (FIG. 6A, FIG. 11E). This combinatorial approach induced a de novo sensitivity to T cell-derived TNF in SK-MEL-23, corroborating our previous observations in D10 cells (FIG. 6B). Extending this observation, we performed the same experiment in other cell lines that require both TRAF2 inactivation and birinapant treatment to become sensitized to T cell challenge. Again, the combination treatment established de novo sensitivity to T cell-derived TNF (FIG. 6C). These data underscore the lack of efficacy of T cell-derived TNF in unmanipulated tumor cells and its unleashed cytotoxic potential after selective modulation, i.e., co-inhibition of TRAF2/cIAP2, of tumor-intrinsic TNF signaling.

Figure 6D:
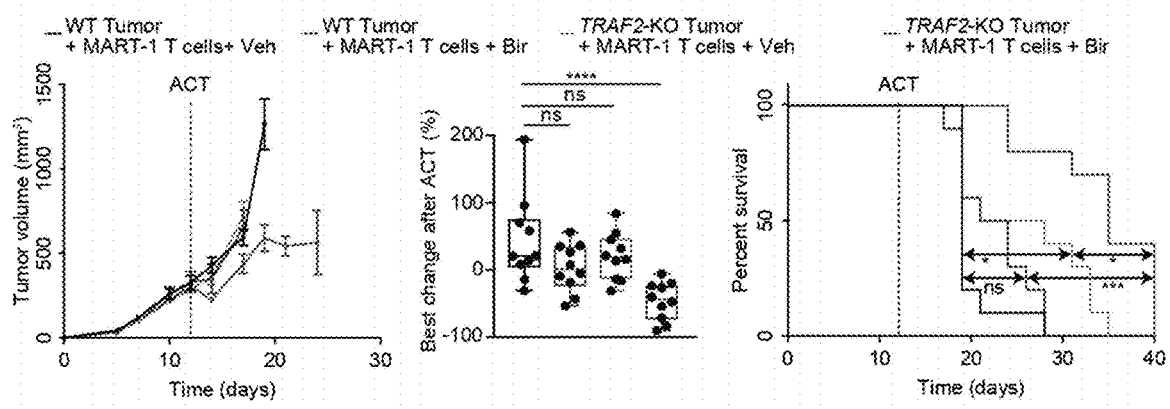
Figure 11F:
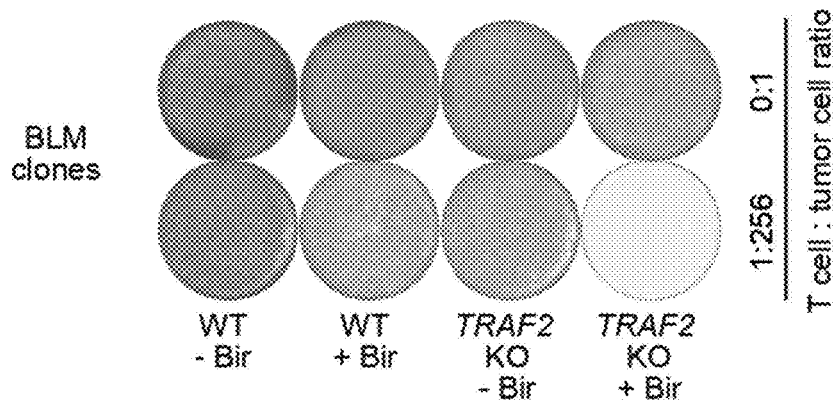
Figure 11G:
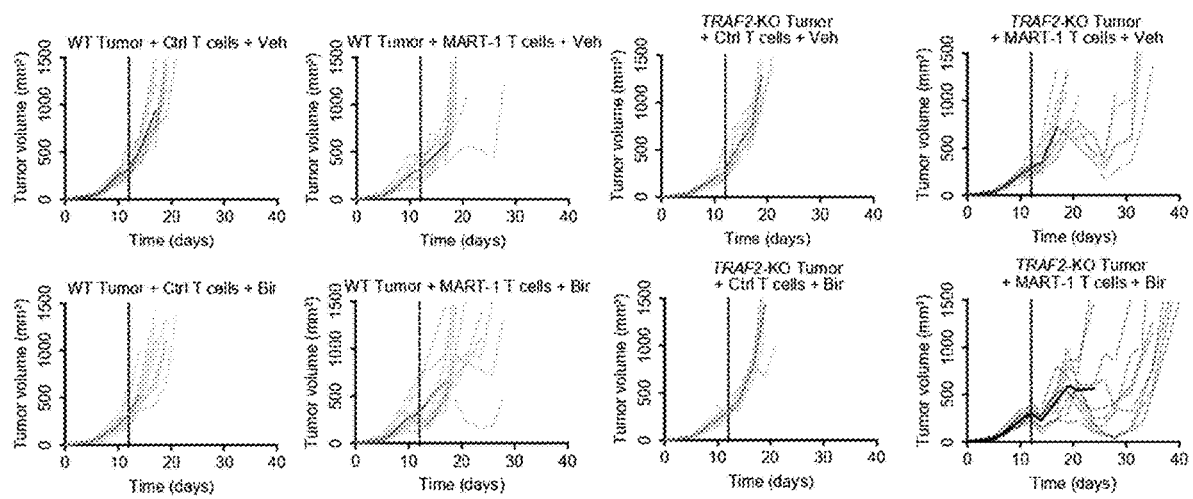
Figure 11H:
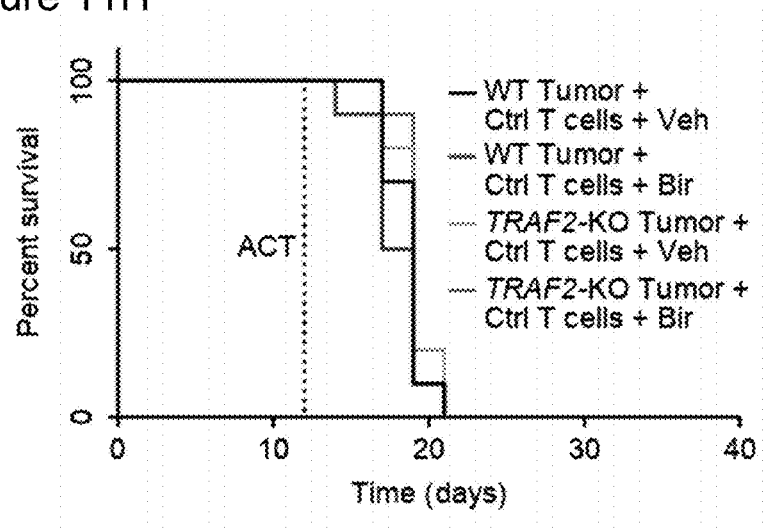

TRAF2/cIAP Complex Inhibition Cooperates with Anti-PD-1 to Eliminate Tumors In Vivo We set out to study any cooperative effect of the combinatorial TRAF2/cIAP targeting approach in vivo. For this, we selected the human melanoma cell line BLM, because of its low susceptibility to T cell killing even upon TRAF2 loss. We established both wildtype and TRAF2-deficient BLM clones and confirmed that they displayed a synergistic response to the combination of TRAF2 deletion and cIAP1/2 inhibition in vitro (FIG. 11F). In vivo, this cell line was highly resistant to ACT in our xenograft mouse model (FIG. 6D, FIG. 11G). However, the combination of TRAF2 genetic inactivation and cIAP1/2 pharmacologic inhibition by birinapant induced both a reduction in tumor volume and extended survival in these mice (FIG. 6D, FIG. 11G, H).

Figure 6E:
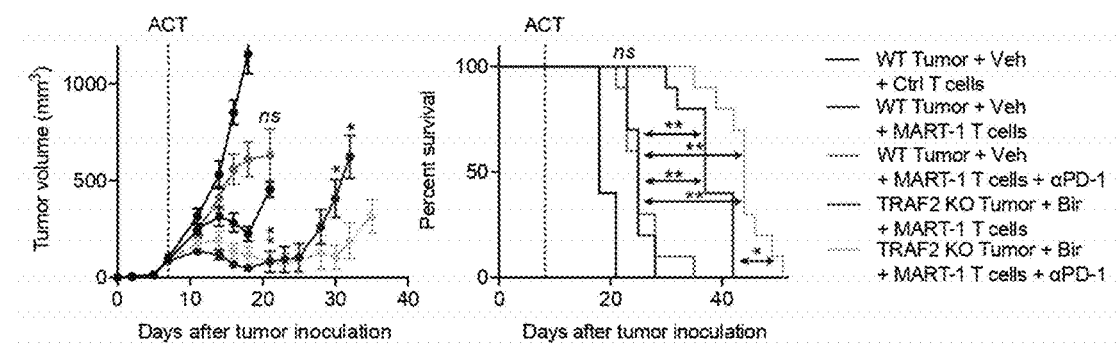
Figure 11I:
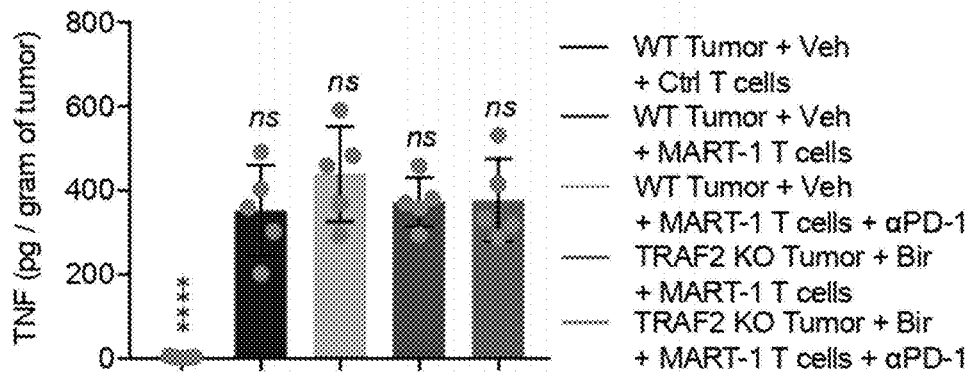

Lastly, we investigated whether this combinatorial targeting approach increases the efficacy of anti-PD-1 therapy. We again employed the BLM melanoma cell line and grafted it in NSG mice. After inoculation of VVT or TRAF2 KO tumors, we injected either control or MART-1 T cells in the presence or absence of anti-PD-1 antibody. Treatment with anti-PD-1 in and of itself therapy failed to affect rejection of VVT tumors, confirming the relative immune resistance of this tumor cell line. In line with our clinical analyses (FIG. 2D), in this non-responding setting, we failed to see an upregulation of TNF after ICB (FIG. 11I). Upon treating TRAF2 KO tumors with birinapant we observed better tumor control when compared to control tumors. Moreover, when anti-PD-1 was included in this combination targeting approach, we observed superior tumor control, improving overall survival (FIG. 6E). These data together imply that selective TNF pathway inhibition can leverage the antitumor activity of anti-PD-1. Furthermore, these results support the hypothesis, based on our clinical observations, that selective targeted inhibition of the TNF pathway can be explored to lower the threshold of tumor elimination by active T cells.

Discussion

ICB has proven to be a transformative therapeutic option in clinical oncology practice (Borghaei et al., 2015; Hodi et al., 2010; Larkin et al., 2015; Motzer et al., 2015; Robert et al., 2011; Rosenberg et al., 2016; Wolchok et al., 2017). Tumor-intrinsic deficiencies in the IFNγ signaling pathway have been correlated with resistance to ICB (Gao et al., 2016; Sharma et al., 2017; Zaretsky et al., 2016). However, it is well established that CD8 T cell-mediated cytotoxicity is mediated also by other cytokines in addition to IFNγ, including TNF and TRAIL (Barber et al., 2006; Barth et al., 1991; Benci et al., 2016; Brincks et al., 2008; Gao et al., 2016; Kakaradov et al., 2017; Kearney et al., 2017, 2018). Here, we explored IFNγ-independent tumor signaling pathways in a systematic and unbiased fashion for new therapeutic targets. We demonstrate that particularly the TNF signaling pathway in tumor cells can be functionally mined to yield critical factors determining the susceptibility of tumors to T cell elimination. We also show the clinical relevance of these results, in that we find that TNF is ineffective at eliminating tumor cells, both at baseline and in patients failing to respond to ICB. While our clinical data suggested that this was likely due to its low functional pressure in tumors, this was corroborated in our in vitro and in vivo studies: upon selective modulation of the TNF pathway, for example by ablating TRAF2, the tumor susceptibility threshold to TNF can be lowered, allowing for tumor eradication. Our results suggest that reducing the TNF cytotoxicity threshold may increase the susceptibility of tumors to immunotherapy.

Our conclusions regarding the role of TNF in driving antitumor immunity are corroborated by three clinical observations. First, we analyzed several patient cohorts before and on ICB therapy. We observed that under baseline conditions, TNF is unlikely to have a strong cytotoxic effect on tumors, as neither TNF expression nor mutations in the TNF pathway have any prognostic power in that setting. Secondly, our data suggest that in patients responding to immunotherapy, TNF has an important role, as evidenced by the higher expression of TNF and TNF response signatures. Thirdly, we find clear evidence of immune editing in the TNF pathway in ICB-treated patients, highlighting the crucial role of TNF alongside IFNγ in T cell cytotoxicity in ICB-responsive patient tumors.

An important inference from these clinical analyses is that whereas TNF in principle has the potential to contribute to T cell-mediated tumor killing, it is hampered by its low functional pressure under baseline conditions. We confirmed this clinically observed inefficacy of TNF in a number of experimental models (FIGS. 2A-G, 3A, B, 4C, D and 6B, C). This raises the question as to why tumors (and derived cell lines) are generally insensitive to TNF. Our results suggest that at least one explanation for this is that TRAF2 is commonly expressed at higher levels in tumors than in normal tissue. We demonstrate that TRAF2 overexpression is sufficient to confer resistance to T cell cytotoxicity. Furthermore, we identified two cancer mutations in TRAF2, R43W and S378F, which, too, render tumor cells resistant to the cytotoxic activity of TNF released by CD8 T cells. Other mechanisms by which tumor cells can escape from T cell-derived TNF, such as loss of CASP8 or TNFRSF1A, have been described in in vitro and animal models (Kearney et al., 2018).

Another important factor to consider in the context of the general inefficacy of TNF is the fact that TNF does not act only cytotoxically. Upon TNF receptor engagement, the bifurcate TNF signaling pathway can either trigger apoptosis or instead, promote cell proliferation and survival (Chen and Goeddel, 2002). Indeed, we show that some tumor cell lines experienced even a beneficial effect of T cell-derived TNF (FIG. 3B, FIG. 6C). Alongside these positive effects on tumor cells, TNF has also been shown to impair mouse melanoma infiltration by CD8 T cells, and therefore TNF antibodies were proposed to be used in combination with PD-1 blockade (Bertrand et al., 2017). As our data demonstrate the beneficial effects of TNF in patients who respond to ICB, we would propose to perturb tumor-intrinsic TNF signaling rather than using a neutralizing TNF antibody.

Our genome-wide CRISPR-Cas9 screen identified a number of signaling factors in the tumor-intrinsic TNF signaling cascade whose inhibition may be useful in this regard, as their inactivation led to increased sensitivity of tumors to T cell killing. As a case in point of such a clinically exploitable TNF pathway modulation, we demonstrate that TRAF2 acts as a critical mediator of both melanoma and lung cancer sensitivity to T cell-derived TNF. Patient data suggest the clinical relevance of this finding: tumors harboring inactivating mutations in TRAF2 are more likely to accumulate mutations in B2M and the HLA class I loci, implying that, also in patient tumors, loss of functional TRAF2 is likely to cause increased sensitivity to T cells. In line with this, we show that loss of TRAF2 can sensitize to clinically relevant, low levels of T cell-derived TNF. Highlighting the clinical relevance of our findings, we also find that inactivating TRAF2, in combination with birinapant, induces responses in tumors that fail to increase TNF levels upon ICB only.

To date, no small molecule inhibitors for TRAF2 are available. However, our finding that clustering of an agonistic Fn14 antibody sensitizes tumor cells to T cell-derived TNF in a TRAF2-dependent manner merits the pre-clinical optimization of such an antibody approach to determine its clinical feasibility in an immunotherapeutic context. Additionally, the interaction partner of TRAF2, cIAP1/2, can be inhibited by the SMAC mimetic birinapant. We demonstrate that TRAF2 inactivation synergizes with pharmacologic inhibition of cIAP1/2 to induce cooperative lethality of tumor cells as well as break their intrinsic T cell resistance. While birinapant has shown some efficacy in preclinical models in combination with immunotherapies (Beug et al., 2017; Kearney et al., 2017), we demonstrate here that its true efficacy can be unleashed by combined targeting of TRAF2. Canonically, TRAF2 and cIAP1/2 are thought to signal in a linear fashion, which would predict that TRAF2 inactivation cannot enhance the effect of cIAP1/2 inactivation or birinapant treatment (Hsu et al., 1996; Mahoney et al., 2008; Shu et al., 1996; Wang et al., 1998; Yeh et al., 1997). What we find, in contrast, is that TRAF2 depletion strongly enhances the degree of tumor killing by T cells upon cIAP1/2 inhibition. This implies that TRAF2 and cIAP1/2 apparently have distinct functions in mediating and transmitting TNF input signals. Utilizing two treatment modalities converging on the same pathway, such as combined BRAF and MEK inhibition in melanoma, has proven its utility in targeted antitumor therapy regimens (Long et al., 2014). To our knowledge, a similar approach has not yet been exploited in the field of immunotherapy, but our work provides the preclinical concept that we feel merits the development of pharmacologic intervention of the TRAF2/cIAP complex.

In conclusion, we show that in in vitro and in vivo models, as well as in patients at baseline and in ICB-unresponsive patients, TNF is present at low levels, displaying little antitumor activity. By selectively modulating the tumor-intrinsic TNF signaling pathway, we can lower the tumor threshold to clinically relevant amounts of TNF, thereby increasing tumor susceptibility to T cell killing. Clinical strategies targeting specific nodes of TNF signaling in tumor cells may thus complement those impacting on T cell functionality to develop novel avenues for immunotherapies and more commonly achieve durable clinical responses to ICB.

TABLE S1

Signature gene sets

| MSigDB gene set | Category | Genes |
| --- | --- | --- |
| SANA_RESPONSE_TO_IFNG_UP | IFNG | APOL2; UBE2L6; UBD; GATA5; RNF213; PPP3CA; C1S; LOC100291917; RABL3; MX1; WARS; sep-04; CASP1; OAS1; GIMAP7; CXCL9; IDO1; CX3CL1; PARP9; LGALS9; ATP6VOA4; HLA-DQB1; CFH; PARP14; RAC3; VAMP5; IFIH1; APOL4; HLA-DRB5; BATF2; GBP1; CXCL10; SSPNDTX3L; MLKL; HLA-DRB1; MMP25; NLRC5; HAUS7; IGKV4-1; SAMHD1; ETV7; SAMD9L; ST8SIA4; CEACAM1; HLA-E; LIPG; TNFSF10; HLA-DRB3; LGALS3BP; GBP3; SERPING1; TRIM22; OAS2; APOL3; HLA-C; HLA-DPA1; IL18BP; IL23A; GOLM1; IFI44L; CXCL11; CD274; HSD17B11; BST2; LAP3; SLC25A28; HLA-A; RARRES3; HLA-B; DDX60; IFI30; APOL1; HLA-DQA1; PLA1A; IFI35; GBP4; HLA-DMA |
| REACTOME_INTERFERON_GAMMA_SIGNALING | IFNG | IRF9; GBP4; GBP5; GBP6; FCGR1A; FCGR1B; GBP1; GBP2; HLA-A; HLA-B; HLA-C; HLA-DPA1; HLA-DPB1; HLA-DQA1; HLA-DQA2; HLA-DRB1; HLA-DRB3; HLA-DRB5; HLA-F; HLA-G; ICAM1; IRF8; IFNG; IFNGR1; IFNGR2; IRF1; IRF2; IRF3; IRF4; IRF5; IRF6; IRF7; JAK1; JAK2; GBP7; CIITA; LOC441019; MT2A; NCAM1; OAS1; OAS2; OAS3; PML; PRKCD; B2M; PTAFR; PTPN1; PTPN2; PTPN6; LOC646981; HLA-K; SP100; STAT1; SUMO1; VCAM1; CAMK2A; CAMK2B; CAMK2D; PIAS1; OASL; SOCS1; SOCS3; CD44 |
| DER_IFN_GAMMA_RESPONSE_UP | IFNG | C1S; PPP5C; SP110; PLSCR1; RBBP4; CASP8; PSMB8; IRF9; MAP3K10; BTG1; SSBP1; BST2; STAT1; BAK1; PSMB9; TRIM26; IFI16; CEBPD; EPS15; RHOC; TAP1; TRIM21; HLA-A; PSME1; SKP1; HADHB; ICAM1; IFITM1; ISG15; HADH; PMAIP1; FOSL1; B2M; VAT1; CYCS; SHFM1; GBP1; IFIT3; PHLDA1; HLA-E; IFI35; IFIT2; ZFP36L2; NMI; PLOD2; FAS; SRP9; SF3A1; TEAD4; SDCBP; ADAR; BBC3; HLA-C; IRF1; XRCC6; IL6; ATP6VOB; COL16A1; PARP1; PML; IFI30; VEGFC; PRAME; CSRP3; PSMB10; PPP3CA; BAG1; ELK4; SRSF2; IL15RA; EIF2B1 |
| PID_IFNG_PATHWAY | IFNG | MTOR; CAMK2D; IFNG; SOCS1; IFNGR1; CRKL; IL1B; SMAD7; MAP3K11; IRF9; PIAS4; STAT1; CREBBP; RAP1A; PIK3CA; PTPN2; JAK2; JAK1; PTPN11; MAPK1; IRF1; STAT3; MAP3K1; DAPK1; RAPGEF1; PTGES2; EP300; MAP2K1; PIK3R1; PIAS1; MAPK3; RAP1B; PRKCD; CAMK2B; CBL; CAMK2A; CAMK2G; CEBPB; AKT1; CASP1 |
| PLASARI_TGFB1_TARGETS_10HR_UP | TGFB | CRISPLD2; HEYL; CA6; TIMP3; PPP1R13L; FBXO32; PLEKHG3; PDGFB; ARNTL; PVR; IER3; ENPP1; GJA3; CSPG4; IER2; MICAL2; ITGB3; TNC; PDGFC; FKBP5; ENDOD1; NUDT6; TFPI2; IL11; KCNK1; KLHDC8A; PI4K2B; OLFM2; SFN; PMAIP1; SLC2A1; KLF13; OLR1; ZNF469; FLT1; STMN4; CTGF; WNT9A; PRKG2; LRP8; TNFRSF11B; FXYD6; GMPPB; BTBD11; GCH1; PRG4; CTH; STK38L; FOXC2; HEY1; KCTD11; ALDH1A2; CD40; NPPB; NUAK1; TMCC3; PLK3; SOCS2; GUCY1B3; MGLL; |

TABLE S1-continued

Signature gene sets

| MSigDB gene set | Category | Genes |
|---|---|---|
| | | UNC5B; RBFOX1; MMP9; ASS1; HSPA2; EREG; JAG1; TNNT2; DUSP14; SIAH2; ITGA5; DUSP4; INHBA; NFATC1; CDH6; FGF2; CHST11; JUNB; ACTA1; OTUD7A; CDYL2; IL6; TSPAN2; SEMA7A; HIVEP3; ENTPD7; HK2; GREM2; NRARP; CX3CL1; HAS2; F2RL1;LRRC8C; CCL17; SPATA13; GPER; ALDH1A3; RUNX1; GJB2; DUSP6; CCL20; GPR84; EGR2; SERP1; RAP1GAP2; GADD45B; LAS1L; SERPINE1; ARC; CNN1; TGFBR1; PLAUR; PKP1; LPIN3; MYO1D; LIF; ALS2CL; FOXS1; SLC41A2; ELN; SGK223; FJX1; HCK; TTC9; CRY1; SNAI1; MAFF; PTGS2; PTK2B; FOSL1; RNF149; NIPAL1; CXCL14; CREB3L2; ARG1; PRKAR2A; HTR2B; ADAM12; MCAM; CMKLR1; UBE2G2; BHLHE40; CSRNP1; RNF19B; NES; CARD10; KHDRBS3; NUAK2; PPP1R15A; VEGFA; NEBL; ABCB1; ANKH; MFSD2A; SLC20A1; TGFB1; PMEPA1; PDGFA; RGS16; MEGF10; LRRFIP1; IL1RL1; PDE4DIP; PTHLH; FSTL3; RASL11B; ELAVL2; NTF4; PAPSS2; GALNT3; GJB3; CXCR6; THBS4; SPHK1; NGF; TNFAIP3; DUSP5; FGF18; WNT11; COL8A2; TNFRSF12A; GATM; HIP1R; ANKRD1; BAIAP2L1; HBEGF; FGF21; FAM59B; GFPT2; NFIL3; GCNT2; FLNB; IVNS1ABP; HECTD2; LMO1; MEOX1; CNNM4; GFOD1; KLHL29 |
| PLASARI_TGFB1_TARGETS_1HR_UP | TGFB | SPATA13; SERPINE1; NR4A1; PTGS2; BHLHE40; SPSB1; SNAH ; RASL11B; KLF10; NUAK2; HES1; SLC20A1; ID2; EGR3; CYR61; GADD45B; CDK5R1; IER5; MAP3K14; FGF18; ID1; ID4; HBEGF; IL6; FBLN2; LIF; JUNB; ZMIZ1; IER3; EGR2; SMAD7; GADD45G; CSRNP1; WNT9A |
| VERRECCHIA_RESPONSE_TO_TGFB1_C2 | TGFB | TGFB; RHOG; TIMP3; CDH6; TIMP1; COL6A1; WNT2B; MMP16; ITGB2; COL3A1; ICAM1; DVL1; SSR1; PCDHGC3; RHOC; ARHGDIA; COL6A3; CD82; FN1; CYTH2; COL1A2; JUP; LRP1; MARCKSL1; MMP14 |
| SANA_TNF_SIGNALING_UP | TNF | UBD; C1S; RABL3; IFI44L; LIPG; IFIT1; ICOSLG; NFKBIA; OXR1; CCL8; KIAA1147; TNIP1; DNAJA1; SOD2; CCL11; SAMD9L; VCAM1; BIRC3; ITGAV; BST2; INHBA; C1QTNF1; LGALS3BP; MX2; OAS3; MMP10; SMAD3; OAS2; FTH1; ATP13A3; TLR2; GBP1; OAS1; CMPK2; CASP1; HLA-C; TAPBP; RIPK2; IL32; SLC15A3; APOL3; RHOB; LGALS9; CXCL10; CCL7; CXCR7; CX3CL1; SAT1; CCL2; PARP14; HSD17B11; TNFAIP2; SLC7A2; CXCL6; APOL1; SAMHD1; NCEH1; ICAM1; SERPINE1; CSF1; IL8; IFI30; SPAG9; DDX60; IFIH1; SSPN; CXCL2; LAMB3; BPGM; RAC3; MX1; PLA1A; ANO9; CCL20; TNFAIP3; CXCL11; CXCL3; HLA-A; HLA-B; IL7R; MMP3; DRAM1; CTHRC1 |
| PHONG_TNF_TARGETS_UP | TNF | ZFP36; GEM; FJX1; DUSP1; BIRC2; EGR1; IL8; BTG3; LAMC2; INHBA; NFKB2; KLF10; FOS; ETS2; DUSP5; PLK2; IL11; REL; ATF3; ICAM1; LDLR; MCL1; BMP2; TNFAIP2; CCNL1; CCL20; ADAMTS9; CD44; IER2; CXCL1; PTX3; CXCL3; KLF6; DUSP8; BHLHE40; BTG1; ZFP36L2; KDM6A; JUNB; SDC4; EREG; NUAK2; IFNGR2; IER5; NKX3-1; CSF2; IER3; CEBPD; PLAU; CXCL2; TNFRSF10B; CD83; DUSP10; TNFAIP3; JUN; NFKBIA; BIRC3; IL6; KLRC1; IRF1; EPHA2; LIF; EGR2 |
| ST_TUMOR_NECROSIS_FACTOR_PATHWAY | TNF | NFKBIA; MAP3K7; TNFRSF1A; MAP3K3; JUN; TNFRSF1B; NFKBIB; CASP3; NR2C2; BAG4; RIPK1; CFLAR; BIRC2; CASP8; NFKB2; TNF; MAP2K4; BIRC3; TRAF2; TRADD; IKBKG; TONSL; FADD; NFKBIE; |

TABLE S1-continued

Signature gene sets

| MSigDB gene set | Category | Genes |
|---|---|---|
| WANG_TNF_TARGETS | TNF | AGFG1; TNFAIP3; NFKB1; RALBP1; NFKBIL1 CSF2; NFKBIA; SELP; KRT35; NOTCH3; TNFAIP3; CD68; VCAM1; TRAF1; GPR56; MMP3; MADCAM1; CD6; IGDCC3; CSF3; IL6; LIMK1; JUN; BCL2L10; MMP13; GDF15; SELE; YY1; GSTT1 |
| PID_TNF_PATHWAY | TNF | TNF; MAP4K5; SMPD1; BAG4; TRAF1; RFFL; GNB2L1; NFKB1; STAT1; NSMAF; MAP3K5; TRADD; TAB2; IKBKB; PRKCZ; TNFAIP3; MAP4K4; TRAF2; RIPK1; CAV1; MAP3K3; PRKCI; BIRC3; IKBKG; CASP8; CHUK; FADD; MAP3K7; TXN; SQSTM1; MAP3K1; MAP4K3; MAP4K2; SMPD2; TAB1; MAP2K3; TNIK; NRK; MADD; MAP2K7; RELA; ADAM17; TNFRSF1B; CYLD; TNFRSF1A; BIRC2 |
| ZHOU_TNF_SIGNALING_4HR | TNF | PCMT1; SF3A3; RPL10; PRDX1; CMPK1; MYL12A; MYL6; TUBA4A; TNFAIP2; FAM50A; KIT; EEF2; CD59; OAZ1; TSPAN3; NFKB1; IL32; CCL2; KEL; PSMB7; CLIC4; ELOVL5; MAN2A1; DROSHA; GINS2; TNIP1; KALRN; SHFM1; PLP2; GDI2; PTGES; CYR61; EBP; CCNC; PSMB8; CDC34; CXCL1; NFKBIA; ITGB2; SMARCE1; NCL; SOD2; RPL27A; RPS23; FBN1; ITGB1; SLMO2; PPP1R10; SNX12; TGFBR3; ACLY; RPS8; TPR; GADD45A |
| PID_TRAIL_PATHWAY | TRAIL | CFLAR; PIK3R3; IKBKG; MAPK1; MAP2K4; PIK3CB; MAPK8; TNFRSF10A; TNFRSF10D; MAPK3; FADD; TNFRSF10C; TNFRSF10B; DAP3; TNFSF10; TRADD; CASP10; IKBKB; RIPK1; CASP8; SMPD1; CHUK; MAP3K1; PIK3R2; PIK3R1; TRAF2; PIK3CD; PIK3CA |
| AYERS | IFNG | IDO1; CXCL10; CXCL9; HLA-DRA; STAT1; IFNG |

TABLE S2

Patient tumors harboring TNF pathway mutations

| Patient | Gene | Chromosome | Start | Reference genotype | Tumor genotype |
|---|---|---|---|---|---|
| NR9521 | BAG4 | 8 | 38050215 | C | T |
| CR6161 | BAG4 | 8 | 38067731 | T | C |
| CR6126 | BIRC3 | 11 | 102201735 | C | T |
| CR04885 | CHUK | 10 | 101969413 | G | A |
| SD2056 | CYLD | 16 | 50813695 | C | T |
| SD2056 | CYLD | 16 | 50813696 | C | T |
| CR04885 | MADD | 11 | 47304508 | C | T |
| CR9306 | MADD | 11 | 47330933 | C | T |
| PR4092 | MADD | 11 | 47298373 | G | A |
| NR2137 | MADD | 11 | 47305781 | G | A |
| NR2137 | MADD | 11 | 47305782 | G | A |
| LSD4744 | MADD | 11 | 47306039 | G | A |
| NR8815 | MADD | 11 | 47310558 | C | T |
| LSD4744 | MAP2K3 | 17 | 21207758 | C | T |
| PR4092 | MAP3K1 | 5 | 56167837 | C | T |
| SD1494 | MAP3K1 | 5 | 56184164 | C | T |
| CR04885 | MAP3K3 | 17 | 61766919 | C | T |
| SD7357 | MAP3K5 | 6 | 136913620 | G | A |
| LSD4744 | MAP3K5 | 6 | 137015438 | G | A |
| NR4631 | MAP3K5 | 6 | 136904808 | C | T |
| CR04885 | MAP3K5 | 6 | 136913596 | C | T |
| NR8815 | MAP3K5 | 6 | 136958506 | C | T |
| CR04885 | MAP3K5 | 6 | 136980443 | A | T |
| PR4092 | MAP3K7 | 6 | 91233480 | G | A |
| LSDNR1120 | MAP4K4 | 2 | 102450880 | T | A |
| NR8815 | MAP4K4 | 2 | 102482958 | C | T |
| NR4949 | MAP4K4 | 2 | 102504394 | C | G |
| NR2137 | MAP4K5 | 14 | 50901138 | G | A |
| NR8815 | NFKB1 | 4 | 103459024 | C | T |
| LSD4744 | NFKB1 | 4 | 103459024 | C | T |
| NR4045 | NFKB1 | 4 | 103528849 | C | T |
| LSD2057 | NRK | X | 105075056 | G | A |
| NR8815 | NRK | X | 105190325 | C | T |
| CRNR2472 | NRK | X | 105179315 | G | A |
| CR9306 | NRK | X | 105189925 | G | A |
| CR9699 | NRK | X | 105156652 | G | A |
| NR4045 | NRK | X | 105159758 | G | A |
| SD7357 | PRKCI | 3 | 169953053 | C | T |
| NR8815 | PRKCZ | 1 | 2106666 | C | T |
| LSD4744 | PRKCZ | 1 | 2106678 | C | T |
| CR04885 | RIPK1 | 6 | 3083358 | A | G |
| SD1494 | RIPK1 | 6 | 3085544 | C | T |
| SD5118 | RIPK1 | 6 | 3105990 | G | T |
| CR9306 | TAB2 | 6 | 149699772 | C | T |
| SD5038 | TNIK | 3 | 170800055 | G | A |
| SD7357 | TNIK | 3 | 170828506 | G | A |

REFERENCES

Ahmadzadeh, M., Johnson, L. A., Heemskerk, B., Wunderlich, J. R., Dudley, M. E., White, D. E., and Rosenberg, S. A. (2009). Tumor antigen-specific CD8 T cells infiltrating the tumor express high levels of PD-1 and are functionally impaired. Blood 114, 1537-1544.

Ayers, M., Lunceford, J., Nebozhyn, M., Murphy, E., Loboda, A., Kaufman, D. R., Albright, A., Cheng, J. D., Kang, S. P., Shankaran, V., et al. (2017). IFN-γ—related mRNA profile predicts clinical response to PD-1 blockade. J. Clin. Invest. 127, 2930-2940.

Barber, D. L., Wherry, E. J., Masopust, D., Zhu, B., Allison, J. P., Sharpe, A. H., Freeman, G. J., and Ahmed, R. (2006). Restoring function in exhausted CD8 T cells during chronic viral infection. Nature 439, 682-687.

Barth, R. J., Mule, J. J., Spiess, P. J., and Rosenberg, S. A. (1991). Interferon gamma and tumor necrosis factor have a role in tumor regressions mediated by murine CD8+ tumor-infiltrating lymphocytes. J. Exp. Med. 173, 647-658.

Benci, J. L., Xu, B., Qiu, Y., Wu, T. J., Dada, H., Twyman-Saint Victor, C., Cucolo, L., Lee, D. S. M., Pauken, K. E., Huang, A. C., et al. (2016). Tumor Interferon Signaling Regulates a Multigenic Resistance Program to Immune Checkpoint Blockade. Cell 167, 1540-1554.e12.

Benetatos, C. A., Mitsuuchi, Y., Burns, J. M., Neiman, E. M., Condon, S. M., Yu, G., Seipel, M. E., Kapoor, G. S., Laporte, M. G., Rippin, S. R., et al. (2014). Birinapant (TL32711), a bivalent SMAC mimetic, targets TRAF2-associated cIAPs, abrogates TNF-induced NF-κB activation, and is active in patient-derived xenograft models. Mol. Cancer Ther. 13, 867-879.

Bertrand, F., Montfort, A., Marcheteau, E., Imbert, C., Gilhodes, J., Filleron, T., Rochaix, P., Andrieu-Abadie, N., Levade, T., Meyer, N., et al. (2017). TNFα blockade overcomes resistance to anti-PD-1 in experimental melanoma. Nat. Commun. 8, 2256.

Beug, S. T., Beauregard, C. E., Healy, C., Sanda, T., St-Jean, M., Chabot, J., Walker, D. E., Mohan, A., Earl, N., Lun, X., et al. (2017). Smac mimetics synergize with immune checkpoint inhibitors to promote tumour immunity against glioblastoma. Nat. Commun. 8.

Blomen, V. A., Majek, P., Jae, L. T., Bigenzahn, J. W., Nieuwenhuis, J., Staring, J., Sacco, R., Van Diemen, F. R., Olk, N., Stukalov, A., et al. (2015). Gene essentiality and synthetic lethality in haploid human cells. Science (80-.). 350, 1092-1096.

Borghaei, H., Paz-Ares, L., Horn, L., Spigel, D. R., Steins, M., Ready, N. E., Chow, L. Q., Vokes, E. E., Felip, E., Holgado, E., et al. (2015). Nivolumab versus Docetaxel in Advanced Nonsquamous Non-Small-Cell Lung Cancer. N. Engl. J. Med. 373, 1627-1639.

Boshuizen, J., Koopman, L. A., Krijgsman, O., Shahrabi, A., van den Heuvel, E. G., Ligtenberg, M. A., Vredevoogd, D. W., Kemper, K., Kuilman, T., Song, J.-Y., et al. (2018). Cooperative targeting of melanoma heterogeneity with an AXL antibody-drug conjugate and BRAF/MEK inhibitors. Nat. Med. 24, 203-212.

Brincks, E. L., Katewa, A., Kucaba, T. A., Griffith, T. S., and Legge, K. L. (2008). CD8 T cells utilize TRAIL to control influenza virus infection. J. Immunol. 181, 4918-4925.

Cao, X., Pobezinskaya, Y. L., Morgan, M. J., and Liu, Z. (2011). The role of TRADD in TRAIL-induced apoptosis and signaling. FASEB J. 25, 1353-1358.

Chen, D. S., and Mellman, I. (2017). Elements of cancer immunity and the cancer-immune set point. Nature 541, 321-330.

Chen, G., and Goeddel, D. V (2002). TNF-R1 signaling: a beautiful pathway. Science 296, 1634-1635.

Curiel, T. J., Coukos, G., Zou, L., Alvarez, X., Cheng, P., Mottram, P., Evdemon-Hogan, M., Conejo-Garcia, J. R., Zhang, L., Burow, M., et al. (2004). Specific recruitment of regulatory T cells in ovarian carcinoma fosters immune privilege and predicts reduced survival. Nat. Med. 10, 942-949.

Dong, H., Strome, S. E., Salomao, D. R., Tamura, H., Hirano, F., Flies, D. B., Roche, P. C., Lu, J., Zhu, G., Tamada, K., et al. (2002). Tumor-associated B7-H1 promotes T-cell apoptosis: A potential mechanism of immune evasion. Nat. Med. 8, 793-800.

Freeman, G. J., Long, A. J., Iwai, Y., Bourque, K., Chernova, T., Nishimura, H., Fitz, L. J., Malenkovich, N., Okazaki, T., Byrne, M. C., et al. (2000). Engagement of the Pd-1 Immunoinhibitory Receptor by a Novel B7 Family Member Leads to Negative Regulation of Lymphocyte Activation. J. Exp. Med. 192, 1027-1034.

Gao, J., Shi, L. Z., Zhao, H., Chen, J., Xiong, L., He, Q., Chen, T., Roszik, J., Bernatchez, C., Woodman, S. E., et al. (2016). Loss of IFN-γ Pathway Genes in Tumor Cells as a Mechanism of Resistance to Anti-CTLA-4 Therapy. Cell 167, 397-404.e9.

Gomez-Eerland, R., Nuijen, B., Heemskerk, B., Van Rooij, N., Van Den Berg, J. H., Beijnen, J. H., Uckert, W., Kvistborg, P., Schumacher, T. N., Haanen, J. B. A. G., et al. (2014). Manufacture of Gene-Modified Human T-Cells with a Memory Stem/Central Memory Phenotype. Hum. Gene Ther. Methods 25, 277-287.

Hart, T., Chandrashekhar, M., Aregger, M., Steinhart, Z., Brown, K. R., MacLeod, G., Mis, M., Zimmermann, M., Fradet-Turcotte, A., Sun, S., et al. (2015). High-Resolution CRISPR Screens Reveal Fitness Genes and Genotype-Specific Cancer Liabilities. Cell 163, 1515-1526.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved Survival with Ipilimumab in Patients with Metastatic Melanoma. N. Engl. J. Med. 363, 711-723.

Hsu, H., Shu, H.-B., Pan, M.-G., and Goeddel, D. V (1996). TRADD-TRAF2 and TRADD-FADD Interactions Define Two Distinct TNF Receptor 1 Signal Transduction Pathways. Cell 84, 299-308.

Jacquelot, N., *Roberti*, M. P., Enot, D. P., Rusakiewicz, S., Ternès, N., Jegou, S., Woods, D. M., Sodré, A. L., Hansen, M., Meirow, Y., et al. (2017). Predictors of responses to immune checkpoint blockade in advanced melanoma. Nat. Commun. 8, 592.

Jenkins, M. H., Steinberg, S. M., Alexander, M. P., Fisher, J. L., Ernstoff, M. S., Turk, M. J., Mullins, D. W., and Brinckerhoff, C. E. (2014). Multiple murine BRaf (V600E) melanoma cell lines with sensitivity to PLX4032. Pigment Cell Melanoma Res. 27, 495-501.

Ji, R.-R., Chasalow, S. D., Wang, L., Hamid, O., Schmidt, H., Cogswell, J., Alaparthy, S., Berman, D., Jure-Kunkel, M., Siemers, N. O., et al. (2012). An immune-active tumor microenvironment favors clinical response to ipilimumab. Cancer Immunol. Immunother. 61, 1019-1031.

Kakaradov, B., Arsenio, J., Widjaja, C. E., He, Z., Aigner, S., Metz, P. J., Yu, B., Wehrens, E. J., Lopez, J., Kim, S. H., et al. (2017). Early transcriptional and epigenetic regulation of CD8+ T cell differentiation revealed by single-cell RNA sequencing. Nat. Immunol. 18, 422-432.

Kearney, C. J., Lalaoui, N., Freeman, A. J., Ramsbottom, K. M., Silke, J., and Oliaro, J. (2017). PD-L1 and IAPs co-operate to protect tumors from cytotoxic lymphocyte-derived TNF. Cell Death Differ. 24, 1705-1716.

Kearney, C. J., Vervoort, S. J., Hogg, S. J., Ramsbottom, K. M., Freeman, A. J., Lalaoui, N., Pijpers, L., Michie, J., Brown, K. K., Knight, D. A., et al. (2018). Tumor immune evasion arises through loss of TNF sensitivity. Sci. Immunol. 3, eaar3451.

Kim, J.-Y., Lee, J.-Y., Kim, D.-G., Koo, G.-B., Yu, J.-W., and Kim, Y.-S. (2011). TRADD is critical for resistance to TRAIL-induced cell death through NF-κB activation. FEBS Lett. 585, 2144-2150.

Kurada, B. R. V. V. S. N., Li, L. C., Mulherkar, N., Subramanian, M., Prasad, K. V, and Prabhakar, B. S. (2009). MADD, a splice variant of IG20, is indispensable for MAPK activation and protection against apoptosis upon tumor necrosis factor-alpha treatment. J. Biol. Chem. 284, 13533-13541.

Lam, E. T., Eckhardt, S. G., Messersmith, W., Jimeno, A., O'Bryant, C. L., Ramanathan, R. K., Weiss, G. J., Chadha, M., Oey, A., Ding, H. T., et al. (2018). Phase I Study of Enavatuzumab, a First-in-Class Humanized Monoclonal Antibody Targeting the TWEAK Receptor, in Patients with Advanced Solid Tumors. Mol. Cancer Ther. 17, 215-221.

Larkin, J., Chiarion-Sileni, V., Gonzalez, R., Grob, J. J., Cowey, C. L., Lao, C. D., Schadendorf, D., Dummer, R., Smylie, M., Rutkowski, P., et al. (2015). Combined Nivolumab and Ipilimumab or Monotherapy in Untreated Melanoma. N. Engl. J. Med. 373, 23-34.

Leach, D. R., Krummel, M. F., and Allison, J. P. (1996). Enhancement of Antitumor Immunity by CTLA-4 Blockade. Science (80-.). 271, 1734-1736.

Li, W., Xu, H., Xiao, T., Cong, L., Love, M. I., Zhang, F., Irizarry, R. A., Liu, J. S., Brown, M., and Liu, X. S. (2014). MAGeCK enables robust identification of essential genes from genome-scale CRISPR/Cas9 knockout screens. Genome Biol. 15, 554.

Lin, Y., Devin, A., Rodriguez, Y., and Liu, Z. G. (1999). Cleavage of the death domain kinase RIP by caspase-8 prompts TNF-induced apoptosis. Genes Dev. 13, 2514-2526.

Long, G. V., Stroyakovskiy, D., Gogas, H., Levchenko, E., de Braud, F., Larkin, J., Garbe, C., Jouary, T., Hauschild, A., Grob, J. J., et al. (2014). Combined BRAF and MEK Inhibition versus BRAF Inhibition Alone in Melanoma. N. Engl. J. Med. 371, 1877-1888.

Love, M. I., Huber, W., and Anders, S. (2014). Moderated estimation of fold change and dispersion for RNA-seq data with DESeq2. Genome Biol. 15, 550.

Mahoney, D. J., Cheung, H. H., Mrad, R. L., Plenchette, S., Simard, C., Enwere, E., Arora, V., Mak, T. W., Lacasse, E. C., Waring, J., et al. (2008). Both cIAP1 and cIAP2 regulate TNFα lpha-mediated NF-kappaB activation. Proc. Natl. Acad. Sci. U.S.A 105, 11778-11783.

Manguso, R. T., Pope, H. W., Zimmer, M. D., Brown, F. D., Yates, K. B., Miller, B. C., Collins, N. B., Bi, K., LaFleur, M. W., Juneja, V. R., et al. (2017). In vivo CRISPR screening identifies Ptpn2 as a cancer immunotherapy target. Nature 547, 413-418.

Motzer, R. J., Escudier, B., McDermott, D. F., George, S., Hammers, H. J., Srinivas, S., Tykodi, S. S., Sosman, J. A., Procopio, G., Plimack, E. R., et al. (2015). Nivolumab versus Everolimus in Advanced Renal-Cell Carcinoma. N. Engl. J. Med. 373, 1803-1813.

Pan, D., Kobayashi, A., Jiang, P., Ferrari de Andrade, L., Tay, R. E., Luoma, A., Tsoucas, D., Qiu, X., Lim, K., Rao, P., et al. (2018). A major chromatin regulator determines resistance of tumor cells to T cell-mediated killing. Science (80-.). 359, 770-775.

Patel, S. J., Sanjana, N. E., Kishton, R. J., Eidizadeh, A., Vodnala, S. K., Cam, M., Gartner, J. J., Jia, L., Steinberg, S. M., Yamamoto, T. N., et al. (2017). Identification of essential genes for cancer immunotherapy. Nature 548, 537-542.

Peng, D., Kryczek, I., Nagarsheth, N., Zhao, L., Wei, S., Wang, W., Sun, Y., Zhao, E., Vatan, L., Szeliga, W., et al. (2015). Epigenetic silencing of TH1-type chemokines shapes tumour immunity and immunotherapy. Nature 527, 249-253.

Post, H., Penning, R., Fitzpatrick, M. A., Garrigues, L. B., Wu, W., MacGillavry, H. D., Hoogenraad, C. C., Heck, A. J. R., and Altelaar, A. F. M. (2017). Robust, Sensitive, and Automated Phosphopeptide Enrichment Optimized for Low Sample Amounts Applied to Primary Hippocampal Neurons. J. Proteome Res. 16, 728-737.

Riaz, N., Havel, J. J., Makarov, V., Desrichard, A., Urba, W. J., Sims, J. S., Hodi, F. S., Martin-Algarra, S., Mandal, R., Sharfman, W. H., et al. (2017). Tumor and Microenvironment Evolution during Immunotherapy with Nivolumab. Cell 171, 934-949.e16.

Ritchie, M. E., Phipson, B., Wu, D., Hu, Y., Law, C. W., Shi, W., and Smyth, G. K. (2015). limma powers differential expression analyses for RNA-sequencing and microarray studies. Nucleic Acids Res. 43, e47-e47.

Robert, C., Thomas, L., Bondarenko, I., O'Day, S., Weber, J., Garbe, C., Lebbe, C., Baurain, J.-F., Testori, A., Grob, J.-J., et al. (2011). Ipilimumab plus Dacarbazine for Previously Untreated Metastatic Melanoma. N. Engl. J. Med. 364, 2517-2526.

Roh, W., Chen, P.-L., Reuben, A., Spencer, C. N., Prieto, P. A., Miller, J. P., Gopalakrishnan, V., Wang, F., Cooper, Z. A., Reddy, S. M., et al. (2017). Integrated molecular analysis of tumor biopsies on sequential CTLA-4 and PD-1 blockade reveals markers of response and resistance. Sci. Transl. Med. 9, eaah3560.

Rosenberg, J. E., Hoffman-Censits, J., Powles, T., van der Heijden, M. S., Balar, A. V, Necchi, A., Dawson, N., O'Donnell, P. H., Balmanoukian, A., Loriot, Y., et al. (2016). Atezolizumab in patients with locally advanced and metastatic urothelial carcinoma who have progressed following treatment with platinum-based chemotherapy: a single-arm, multicentre, phase 2 trial. Lancet 387, 1909-1920.

Salzmann, S., Seher, A., Trebing, J., Weisenberger, D., Rosenthal, A., Siegmund, D., and Wajant, H. (2013). Fibroblast Growth Factor Inducible (Fn14)-specific Antibodies Concomitantly Display Signaling Pathway-specific Agonistic and Antagonistic Activity. J. Biol. Chem. 288, 13455-13466.

Sasi, S. P., Yan, X., Enderling, H., Park, D., Gilbert, H.-Y., Curry, C., Coleman, C., Hlatky, L., Qin, G., Kishore, R., et al. (2012). Breaking the "harmony" of TNF-α signaling for cancer treatment. Oncogene 31, 4117-4127.

Schievella, A. R., Chen, J. H., Graham, J. R., and Lin, L. L. (1997). MADD, a novel death domain protein that interacts with the type 1 tumor necrosis factor receptor and activates mitogen-activated protein kinase. J. Biol. Chem. 272, 12069-12075.

Schulze-Osthoff, K., Ferrari, D., Los, M., Wesselborg, S., and Peter, M. E. (1998). Apoptosis signaling by death receptors. Eur. J. Biochem. 254, 439-459.

Shalem, O., Sanjana, N. E., Hartenian, E., Shi, X., Scott, D. A., Mikkelson, T., Heckl, D., Ebert, B. L., Root, D. E., Doench, J. G., et al. (2014). Genome-scale CRISPR-Cas9 knockout screening in human cells. Science 343, 84-87.

Sharma, P., Hu-Lieskovan, S., Wargo, J. A., and Ribas, A. (2017). Primary, Adaptive, and Acquired Resistance to Cancer Immunotherapy. Cell 168, 707-723.

Shin, D. S., Zaretsky, J. M., Escuin-Ordinas, H., Garcia-Diaz, A., Hu-Lieskovan, S., Kalbasi, A., Grasso, C. S., Hugo, W., Sandoval, S., Torrejon, D. Y., et al. (2017). Primary Resistance to PD-1 Blockade Mediated by JAK1/2 Mutations. Cancer Discov. 7, 188-201.

Shu, H.-B., Takeuchi, M., Goeddel, D. V., Plenchette, S., Simard, C., Enwere, E., Arora, V., Mak, T. W., Lacasse, E. C., Waring, J., et al. (1996). The tumor necrosis factor receptor 2 signal transducers TRAF2 and c-IAP1 are components of the tumor necrosis factor receptor 1 signaling complex. Proc. Natl. Acad. Sci. 93, 13973-13978.

Snyder, A., Makarov, V., Merghoub, T., Yuan, J., Zaretsky, J. M., Desrichard, A., Walsh, L. A., Postow, M. A., Wong, P., Ho, T. S., et al. (2014). Genetic Basis for Clinical Response to CTLA-4 Blockade in Melanoma. N. Engl. J. Med. 371, 2189-2199.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc. Natl. Acad. Sci. U.S.A 102, 15545-15550.

Vince, J. E., Chau, D., Callus, B., Wong, W. W.-L., Hawkins, C. J., Schneider, P., McKinlay, M., Benetatos, C. A., Condon, S. M., Chunduru, S. K., et al. (2008). TWEAK-FN14 signaling induces lysosomal degradation of a cIAP1-TRAF2 complex to sensitize tumor cells to TNFα. J. Cell Biol. 182, 171-184.

Wang, C. Y., Mayo, M. W., Korneluk, R. G., Goeddel, D. V, and Baldwin, A. S. (1998). NF-kappaB antiapoptosis: induction of TRAF1 and TRAF2 and c-IAP1 and c-IAP2 to suppress caspase-8 activation. Science 281, 1680-1683.

Wang, T., Birsoy, K., Hughes, N. W., Krupczak, K. M., Post, Y., Wei, J. J., Lander, E. S., and Sabatini, D. M. (2015). Identification and characterization of essential genes in the human genome. Science (80-.). 350, 1096-1101.

Wolchok, J. D., Chiarion-Sileni, V., Gonzalez, R., Rutkowski, P., Grob, J.-J., Cowey, C. L., Lao, C. D., Wagstaff, J., Schadendorf, D., Ferrucci, P. F., et al. (2017). Overall Survival with Combined Nivolumab and Ipilimumab in Advanced Melanoma. N. Engl. J. Med. 377, 1345-1356.

Wu, H. (2004). Assembly of Post-Receptor Signaling Complexes for the Tumor Necrosis Factor Receptor Superfamily. In Advances in Protein Chemistry, pp. 225-279.

Yeh, W.-C., Shahinian, A., Speiser, D., Kraunus, J., Billia, F., Wakeham, A., de la Pompa, J. L., Ferrick, D., Hum, B., Iscove, N., et al. (1997). Early Lethality, Functional NF-κB Activation, and Increased Sensitivity to TNF-Induced Cell Death in TRAF2-Deficient Mice. Immunity 7, 715-725.

Young, L., Sung, J., Stacey, G., and Masters, J. R. (2010). Detection of *Mycoplasma* in cell cultures. Nat. Protoc. 5, 929-934.

Yurkovetsky, Z. R., Kirkwood, J. M., Edington, H. D., Marrangoni, A. M., Velikokhatnaya, L., Winans, M. T., Gorelik, E., and Lokshin, A. E. (2007). Multiplex Analysis of Serum Cytokines in Melanoma Patients Treated with Interferon-2b. Clin. Cancer Res. 13, 2422-2428.

Zaretsky, J. M., Garcia-Diaz, A., Shin, D. S., Escuin-Ordinas, H., Hugo, W., Hu-Lieskovan, S., Torrejon, D. Y., Abril-Rodriguez, G., Sandoval, S., Barthly, L., et al. (2016). Mutations Associated with Acquired Resistance to PD-1 Blockade in Melanoma. N. Engl. J. Med. 375, 819-829.

Zhang, S., Ke, X., Zeng, S., Wu, M., Lou, J., Wu, L., Huang, P., Huang, L., Wang, F., and Pan, S. (2015). Analysis of CD8+Treg cells in patients with ovarian cancer: a possible mechanism for immune impairment. Cell. Mol. Immunol. 12, 580-591.

The invention claimed is:

1. A method for the treatment of a tumor in a subject in need thereof, wherein the method comprises administering a TWEAK-receptor agonist combined with an immunotherapy of the tumor and wherein the tumor has at least one of: a low IFNγ response signature, a defect in the IFNγ pathway, a low IFNγ expression level, a low TNF expression level and a low TNF response signature.

2. The method according to claim 1, wherein the TWEAK-receptor agonist is an agonistic ligand of a TNFR-family member.

3. The method according to claim 1, wherein the TWEAK-receptor agonist is an agonistic ligand of Fn14.

4. The method according to claim 3, wherein the agonistic ligand of Fn14 is selected from: i) TWEAK or an agonistic fragment thereof; and, ii) a TWEAK mimetic that acts as an agonistic ligand of Fn14.

5. The method according to claim 4, wherein the agonistic ligand of Fn14 is a multivalent ligand of Fn14.

6. The method according to claim 3, wherein the TWEAK mimetic is one or more of a peptide, a peptidomimetic, an aptamer, a small molecule and agonistic anti-Fn14 antibody.

7. The method according to claim 1, wherein the immunotherapy of the cancer comprises at least one of adoptive cell transfer (ACT) and immune checkpoint therapy.

8. The method according to claim 7, wherein the ACT comprises T cell adoptive transfer.

9. The method according to claim 7, wherein the immune checkpoint therapy comprises the use of an immune checkpoint blocking agent that blocks at least one of PD-1, PD-L1 and CTLA-4.

10. The method according to claim 1, wherein the method further comprises the administration of a SMAC mimetic.

11. The method according to claim 1, wherein the cancer comprises tumor cells with a mutation in a TNF pathway component.

12. The method according to claim 1, wherein the TWEAK-receptor agonist is used, optionally in combination with a SMAC mimetic, to prevent resistance to immune checkpoint therapy or to treat a cancer comprising tumor cells that are resistant to immune checkpoint therapy.

13. The method according to claim 1, wherein the TWEAK-receptor agonist is administered simultaneously, separately or sequentially with the immunotherapy of the cancer.

14. The method according to claim 13, wherein the TWEAK-receptor agonist is administered as a pretreatment of the immunotherapy of the cancer.

15. A method for identifying a TWEAK-receptor agonist, the method comprising the steps:
   a) providing tumor cells presenting an antigen-MHC class I complex and lacking functional IFNγ signaling;
   b) contacting the tumor cells of step a) with at least one candidate agonist of interest;
   c) co-incubating the tumor cells obtained from step b) with CD8 T cells expressing a T cell receptor that recognizes the antigen-MHC class I complex presented by the tumor cells of step a);
   d) determining whether the tumor cells in step c) undergo programmed cell death;
   e) identifying a candidate agonist as a TWEAK-receptor agonist if in step d) the tumor cells are determined to undergo programmed cell death at a greater rate than:
      i) corresponding tumor cells contacted with the candidate agonist and co-incubated with CD8 T cells that do express the T cell receptor that recognizes the antigen-MHC class I complex presented by the tumor cells of step a); and/or,
      ii) corresponding tumor cells not contacted with the candidate agonist and co-incubated with CD8 T cells expressing the T cell receptor that recognizes the antigen-MHC class I complex presented by the tumor cells of step a).

16. The method according to claim 3, wherein the TWEAK mimetic the anti-Fn14 antibody enavatuzumab.

17. The method according to claim 7, wherein the immune checkpoint therapy comprises the use of an immune checkpoint blocking agent that blocks at least one of ipilimumab, nivolumab, pembrolizumab, antibody BGB-A31 and atezolizumab.

18. The method according to claim 1, wherein the method further comprises the administration of the SMAC mimetic birinapant.

19. The method according to claim 1, wherein the TWEAK-receptor agonist is administered simultaneously, separately or sequentially with the immunotherapy of the cancer with the SMAC mimetic.

20. The method according to claim 15 for identifying a TWEAK-receptor agonist, wherein step d) comprises:
   d) determining whether the tumor cells in step c) undergo programmed cell death as indicated by an induction of Caspase-3/7 activity over time.

* * * * *